US010980730B2

(12) United States Patent
Belinky et al.

(10) Patent No.: US 10,980,730 B2
(45) Date of Patent: Apr. 20, 2021

(54) ENZYMATIC SYSTEM-CONTAINING COSMETIC COMPOSITIONS

(71) Applicant: Rakuto Bio Technologies Ltd., Yokneam Ilit (IL)

(72) Inventors: Paula Belinky, Metulla (IL); Yoram Karmon, Petah Tikva (IL); Bella Krinfeld, Kiryat-Shmona (IL); Haim Lasser, Kfar Saba (IL)

(73) Assignee: Rakuto Bio Technologies Ltd., Yokneam Ilit (IL)

( * ) Notice: Subject to any disclaimer, the term of this patent is extended or adjusted under 35 U.S.C. 154(b) by 257 days.

(21) Appl. No.: 14/894,355

(22) PCT Filed: May 27, 2014

(86) PCT No.: PCT/IL2014/050477
§ 371 (c)(1),
(2) Date: Nov. 26, 2015

(87) PCT Pub. No.: WO2014/191995
PCT Pub. Date: Dec. 4, 2014

(65) Prior Publication Data
US 2016/0101034 A1   Apr. 14, 2016

Related U.S. Application Data

(60) Provisional application No. 61/827,685, filed on May 27, 2013.

(51) Int. Cl.
| A61K 8/66 | (2006.01) |
| A61Q 19/02 | (2006.01) |
| A61Q 5/08 | (2006.01) |
| A61K 8/34 | (2006.01) |
| A61K 8/33 | (2006.01) |
| A61Q 3/00 | (2006.01) |
| A61K 8/9728 | (2017.01) |
| A61K 8/9789 | (2017.01) |
| A61K 8/60 | (2006.01) |

(52) U.S. Cl.
CPC .......... *A61K 8/66* (2013.01); *A61K 8/33* (2013.01); *A61K 8/34* (2013.01); *A61K 8/60* (2013.01); *A61K 8/9728* (2017.08); *A61K 8/9789* (2017.08); *A61Q 3/00* (2013.01); *A61Q 5/08* (2013.01); *A61Q 19/02* (2013.01); *A61K 2800/5922* (2013.01); *A61K 2800/805* (2013.01); *A61K 2800/88* (2013.01)

(58) Field of Classification Search
CPC ............ A61K 8/66; A61Q 19/02; A61Q 5/08
USPC ..................................................... 424/94.4
See application file for complete search history.

(56) References Cited

U.S. PATENT DOCUMENTS

| 5,607,681 | A | 3/1997 | Galley et al. | |
|---|---|---|---|---|
| 6,214,339 | B1 | 4/2001 | Pellico | |
| 6,312,477 | B1 | 11/2001 | De La Mettrie et al. | |
| 6,379,653 | B1* | 4/2002 | Aaslyng ................... | A61K 8/66 424/49 |
| 7,799,096 | B2* | 9/2010 | Gross ........................... | 424/94.4 |
| 7,833,290 | B2 | 11/2010 | Guerin et al. | |
| 7,981,166 | B2 | 7/2011 | Gross et al. | |
| 8,426,158 | B2 | 4/2013 | Xu et al. | |
| 8,691,194 | B2* | 4/2014 | Belinky .................... | A61K 8/66 424/62 |
| 2004/0040098 | A1 | 3/2004 | Lang et al. | |
| 2004/0161435 | A1 | 8/2004 | Gupta | |
| 2005/0013784 | A1 | 1/2005 | Trigg et al. | |
| 2007/0128129 | A1 | 6/2007 | Stehr et al. | |
| 2009/0041692 | A1* | 2/2009 | Belinky .................... | A61K 8/66 424/62 |
| 2009/0130040 | A1 | 5/2009 | Jonchiere | |
| 2009/0241242 | A1 | 10/2009 | Beatty et al. | |
| 2010/0037909 | A1 | 2/2010 | Gross et al. | |

FOREIGN PATENT DOCUMENTS

| CA | 2626414 | 4/2007 |
|---|---|---|
| CN | 1196674 | 10/1998 |
| DE | 102005041443 | 3/2007 |
| DE | 102009045798 | 8/2010 |
| FR | 2794022 | 12/2000 |
| JP | 2001-010939 | 1/2001 |
| JP | 2006-514943 | 5/2006 |
| JP | 2009-511078 | 3/2009 |

(Continued)

OTHER PUBLICATIONS

Noble et al. 1970. The Reaction of Ferrous Horseradish Peroxidase with Hydrogen Peroxide. The Journal of Biological Chemis'i'ry vol. 245, No. 9pp. 2409-2413.*
Butler et al., 1998.Destruction of Fungal Melanins by Ligninases of Phanerochaete Chrysosporium and Other White Rot Fungi. International Journal of Plant Science, vol. 159, pp. 989-995.*
Federal Register /vol. 79, No. 241 /Tuesday, Dec. 16, 2014.*
Federal Register, vol. 80, No. 146/Thursday, Jul. 30, 2015/ Rules and Regulations. p. 45429, col. 1, Lines 9-43.*
2016 Subject Matter Eligibility Update (Federal Register, vol. 81, No. 88, May 6, 2016 pp. 27381-27382).*

(Continued)

*Primary Examiner* — Louise W Humphrey
*Assistant Examiner* — Anjali Ajit Hirani

(57) ABSTRACT

Cosmetic or pharmaceutical compositions are described herein for application to skin, hair and/or a nail of a subject, as well as methods utilizing same for administering hydrogen peroxide to skin, hair and/or a nail, and kits for applying same. The compositions comprise a hydrogen peroxide-producing enzyme, and a substrate of the hydrogen peroxide-producing enzyme. Further described herein are cosmetic compositions and kits for lightening skin and/or hair, which further comprise a lignin peroxidase, as well as cosmetic methods utilizing same.

11 Claims, 13 Drawing Sheets
(2 of 13 Drawing Sheet(s) Filed in Color)

Specification includes a Sequence Listing.

(56) References Cited

FOREIGN PATENT DOCUMENTS

| JP | 2010-505817 | 2/2010 |
|---|---|---|
| KR | 10-2005-0088381 | 9/2005 |
| WO | WO 88/02600 | 4/1988 |
| WO | WO 2004/052275 | 6/2004 |
| WO | WO 2007/045252 | 4/2007 |
| WO | WO 2008/041218 | 4/2008 |
| WO | WO 2012/153336 | 11/2012 |
| WO | WO 2014/191995 | 12/2014 |

OTHER PUBLICATIONS

Bankar et al., Available on Line 2009. Glucose oxidase—An Overview. Biotechnology Advances, vol. 27, pp. 489-501.*
Kawai et al., 1986.De Novo Synthesis of Veratryl Alcohol by Coriolus versicolor. Wood research: bulletin of the Wood Research Institute Kyoto University, vol. 73 pp. 18-21.*
Corspack 2008. Airless Containers and Stock Cosmetics Packaging. Downloaded Jun. 25, 2017 from www.cospackamerica.com/instock_instyle/instock_instyle.html.*
Matityahu et al. "Involvement of protein kinase C in lignin peroxidase expression in oxygenated cultures of the white rot fungus Phanerochaete chrysosporium" Enzyme and Microbial Technology 47 (2010) 59-63.*
Tao et al. "Kinetic Studies on Enzyme-Catalyzed Reactions: Oxidation of Glucose, Decomposition of Hydrogen Peroxide and Their Combination" Biophysical Journal vol. 96 Apr. 2009 2977-2988.*
Search Report and Written Opinion dated Aug. 15, 2016 From the Intellectual Property Office of Singapore Re. Application No. 11201509636X.
Wong et al. "Glucose Oxidase: Natural Occurrence, Function, Properties and Industrial Applications", Applied Microbiology and Biotechnology, 78(6): 927-938, Published Online Mar. 11, 2008.
International Preliminary Report on Patentability dated Dec. 10, 2015 From the International Bureau of WIPO Re. Application No. PCT/IL2014/050477.
International Preliminary Report on Patentability dated Nov. 21, 2013 From the International Bureau of WIPO Re. Application No. PCT/IL2012/050166.
International Search Report and the Written Opinion dated Jan. 23, 2015 From the International Searching Authority Re. Application No. PCT/IL2014/050477.
International Search Report and the Written Opinion dated Sep. 30, 2013 From the International Searching Authority Re. Application No. PCT/IL2012/050166.
British Dental Association "Product News", British Dental Journal, 205(12): 681, Dec. 20, 2008.
Jansen et al. Para [0001], [0006] - [0007], [0005] -[0011], [0022], [0025], [0040] [0042], [0066], [0101], [0158], [0161], [0165], [0178] - [0183], Claims 1-10, Esp. Claims 6, 8.
Midda et al. "Clinical Uses of an Enzyme-Containing Dentifrice", Journal of Clinical Periodontology, 13(10): 950-956, Nov. 1986.
Mintel "Intens Brightening and Correcting Night Cream", Database GNPD [Online], XP002732580, Syneron Beauty, Database Accession No. 1889052, Oct. 2012. Ingredients.
Translation of Notification of Office Action dated Mar. 14, 2017 From the State Intellectual Property Office of the People's Republic of China Re. Application No. 201480037484.5. (8 Pages).
Decision on Rejection dated Apr. 9, 2018 From the State Intellectual Property Office of the People's Republic of China Re. Application No. 201480037484.5. (6 Pages).
Request for Examination and Search Report dated Apr. 24, 2018 From the ROSPATENT, Federal Government Institution, Federal Institute of Industrial Property of the Federal Service for Intellectual Property, Patents and Trademarks Re. Application No. 2015151047 and Its Summary in English. (10 Pages).
Search Report and Written Opinion dated May 24, 2018 From the Intellectual Property Office of Singapore, IPOS Re. Application No. 10201707029Y. (8 Pages).
Translation dated May 30, 2018 of Decision on Rejection dated Apr. 9, 2018 From the State Intellectual Property Office of the People's Republic of China Re. Application No. 201480037484.5. (9 Pages).
Communication Pursuant to Article 94(3) EPC dated Jul. 12, 2017 From the European Patent Office Re. Application No. 14732644.1. (7 Pages).
Examination Report dated Jun. 29, 2017 From the Intellectual Property Office of Singapore Re. Application No. 11201509636X. (6 Pages).
Notification of Office Action dated Aug. 2, 2017 From the State Intellectual Property Office of the People's Republic of China Re. Application No. 201480037484.5 and Its Summary in English. (9 Pages).
Translation of Notification of Office Action dated Aug. 2, 2017 From the State Intellectual Property Office of the People's Republic of China Re. Application No. 201480037484.5. (10 Pages).
Communication Pursuant to Article 94(3) EPC dated Aug. 3, 2018 From the European Patent Office Re. Application No. 14732644.1. (3 Pages).
Office Action dated Aug. 20, 2018 From the Israel Patent Office Re. Application No. 242806 and Its Translation Into English. (6 Pages).
Notice of Reasons for Rejection dated Jul. 6, 2018 From the Japanese Patent Office Re. Application No. 2016-516305. (6 Pages).
Translation dated Jul. 24, 2018 of Notice of Reasons for Rejection dated Jul. 6, 2018 From the Japanese Patent Office Re. Application No. 2016-516305. (7 Pages).
Translation dated May 13, 2019 of Notice of Reasons for Rejection dated Apr. 9, 2019 From the Japan Patent Office Re. Application No. 2016-516305. (8 Pages).
Notice of Reasons for Rejection dated Apr. 9, 2019 From the Japan Patent Office Re. Application No. 2016-516305. (6 Pages).
Search Report and Explanations dated Jul. 24, 2019 From the Serviço Publico Federal, Ministerio da Economia, Instituto Nacional da Propriedade Industrial do Brasil Re. Application No. BR112015029815-0 and Its Summary in English. (5 Pages).
Examination Report dated Mar. 28, 2019 From the Instituto Mexicano de la Propiedad Industrial, IMPI, Direccion Divisional de Patentes Re. Application No. MX/a/2015/016262. (3 Pages).
Translation dated May 1, 2019 of Examination Report dated Mar. 28, 2019 From the Instituto Mexicano de la Propiedad Industrial, IMPI, Direccion Divisional de Patentes Re. Application No. MX/a/2015/016262. (3 Pages).
European Search Report and the European Search Opinion dated Dec. 20, 2019 From the European Patent Office Re. Application No. 19199329.4. (10 Pages).
Notice of Eligibility for Grant and Examination Report dated Jan. 9, 2020 From the Intellectual Property Office of Singapore, IPOS Re. Application No. 10201707029Y. (5 Pages).
Requisition by the Examiner dated Jun. 29, 2020 From the Innovation, Science and Economic Development Canada, Canadian Intellectual Property Office Re. Application No. 2,912,997. (10 Pages).
Examination Report Under Sections 12 & 13 of the Patents Act, 1970 and the Patents Rules, 2003 dated Jul. 16, 2020 From the Government of India, Intellectual Property India, Patents, Designs, Trade Marks, Geographical Indications, The Patent Office Re. Application No. 3386/MUMNP/2015. (5 Pages).
Notification of Office Action and Search Report dated Sep. 16, 2020 From the State Intellectual Property Office of the People's Republic of China Re. Application No. 201810767537.9. (11 Pages).
Translation dated Sep. 9, 2020 of Grounds of Reasons for Rejection dated Aug. 21, 2020 From the Korean Intellectual Property Office Re. Application No. 10-2015-7036644. (9 Pages).
Grounds of Reasons for Rejection dated Aug. 21, 2020 From the Korean Intellectual Property Office Re. Application No. 10-2015-7036644. (10 Pages).

* cited by examiner

SEQUENCE LISTING

<160> NUMBER OF SEQ ID NOS: 27

<210> SEQ ID NO 1
<211> LENGTH: 371
<212> TYPE: PRT
<213> ORGANISM: Phanerochaete chrysosporium

<400> SEQUENCE: 1

```
Met Ala Phe Lys Gln Leu Phe Ala Ala Ile Thr Val Ala Leu Ser Leu
1               5                   10                  15

Thr Ala Ala Asn Ala Ala Val Val Lys Glu Lys Arg Ala Thr Cys Ala
            20                  25                  30
```

```
Asn Gly Lys Thr Val Gly Asp Ala Ser Cys Cys Ala Trp Phe Asp Val
         35                  40                  45

Leu Asp Asp Ile Gln Ala Asn Met Phe His Gly Gly Gln Cys Gly Ala
 50                  55                  60

Glu Ala His Glu Ser Ile Arg Leu Val Phe His Asp Ser Ile Ala Ile
 65                  70                  75                  80

Ser Pro Ala Met Glu Ala Lys Gly Lys Phe Gly Gly Gly Ala Asp
                 85                  90                  95

Gly Ser Ile Met Ile Phe Asp Thr Ile Glu Thr Ala Phe His Pro Asn
                100                 105                 110

Ile Gly Leu Asp Glu Val Val Ala Met Gln Lys Pro Phe Val Gln Lys
             115                 120                 125

His Gly Val Thr Pro Gly Asp Phe Ile Ala Phe Ala Gly Ala Val Ala
         130                 135                 140

Leu Ser Asn Cys Pro Gly Ala Pro Gln Met Asn Phe Phe Thr Gly Arg
145                 150                 155                 160

Lys Pro Ala Thr Gln Pro Ala Pro Asp Gly Leu Val Pro Glu Pro Phe
                165                 170                 175

His Thr Val Asp Gln Ile Ile Ala Arg Val Asn Asp Ala Gly Glu Phe
            180                 185                 190

Asp Glu Leu Glu Leu Val Trp Met Leu Ser Ala His Ser Val Ala Ala
            195                 200                 205

Val Asn Asp Val Asp Pro Thr Val Gln Gly Leu Pro Phe Asp Ser Thr
        210                 215                 220

Pro Gly Ile Phe Asp Ser Gln Phe Phe Val Glu Thr Gln Phe Arg Gly
225                 230                 235                 240

Thr Leu Phe Pro Gly Ser Gly Asn Gln Gly Glu Val Glu Ser Gly
                245                 250                 255

Met Ala Gly Glu Ile Arg Ile Gln Thr Asp His Thr Leu Ala Arg Asp
                260                 265                 270

Ser Arg Thr Ala Cys Glu Trp Gln Ser Phe Val Asn Asn Gln Ser Lys
        275                 280                 285

Leu Val Asp Asp Phe Gln Phe Ile Phe Leu Ala Leu Thr Gln Leu Gly
        290                 295                 300

Gln Asp Pro Asn Ala Met Thr Asp Cys Ser Asp Val Ile Pro Leu Ser
305                 310                 315                 320

Lys Pro Ile Pro Gly Asn Gly Pro Phe Ser Phe Pro Pro Gly Lys
                325                 330                 335

Ser His Ser Asp Ile Glu Gln Ala Cys Ala Glu Thr Pro Phe Pro Ser
            340                 345                 350

Leu Val Thr Leu Pro Gly Pro Ala Thr Ser Val Ala Arg Ile Pro Pro
            355                 360                 365

His Lys Ala
    370

<210> SEQ ID NO 2
<211> LENGTH: 462
<212> TYPE: PRT
<213> ORGANISM: Mycobacterium tuberculosis H37Rv

<400> SEQUENCE: 2

Met Ala Gln Ala Pro His Ile His Arg Thr Arg Tyr Ala Lys Cys Gly
1               5                  10                  15

Asp Met Asp Ile Ala Tyr Gln Val Leu Gly Asp Gly Pro Thr Asp Leu
```

```
            20                  25                  30
Leu Val Leu Pro Gly Pro Phe Val Pro Ile Asp Ser Ile Asp Asp Glu
            35                  40                  45
Pro Ser Leu Tyr Arg Phe His Arg Arg Leu Ala Ser Phe Ser Arg Val
            50                  55                  60
Ile Arg Leu Asp His Arg Gly Val Gly Leu Ser Ser Arg Leu Ala Ala
 65                  70                  75                  80
Ile Thr Thr Leu Gly Pro Lys Phe Trp Ala Gln Asp Ala Ile Ala Val
                    85                  90                  95
Met Asp Ala Val Gly Cys Glu Gln Ala Thr Ile Phe Ala Pro Ser Phe
                    100                 105                 110
His Ala Met Asn Gly Leu Val Leu Ala Ala Asp Tyr Pro Glu Arg Val
                    115                 120                 125
Arg Ser Leu Ile Val Val Asn Gly Ser Ala Arg Pro Leu Trp Ala Pro
                    130                 135                 140
Asp Tyr Pro Val Gly Ala Gln Val Arg Arg Ala Asp Pro Phe Leu Thr
145                 150                 155                 160
Val Ala Leu Glu Pro Asp Ala Val Glu Arg Gly Phe Asp Val Leu Ser
                    165                 170                 175
Ile Val Ala Pro Thr Val Ala Gly Asp Asp Val Phe Arg Ala Trp Trp
                    180                 185                 190
Asp Leu Ala Gly Asn Arg Ala Gly Pro Pro Ser Ile Ala Arg Ala Val
                    195                 200                 205
Ser Lys Val Ile Ala Glu Ala Asp Val Arg Asp Val Leu Gly His Ile
                    210                 215                 220
Glu Ala Pro Thr Leu Ile Leu His Arg Val Gly Ser Thr Tyr Ile Pro
225                 230                 235                 240
Val Gly His Gly Arg Tyr Leu Ala Glu His Ile Ala Gly Ser Arg Leu
                    245                 250                 255
Val Glu Leu Pro Gly Thr Asp Thr Leu Tyr Trp Val Gly Asp Thr Gly
                    260                 265                 270
Pro Met Leu Asp Glu Ile Glu Glu Phe Ile Thr Gly Val Arg Gly Gly
                    275                 280                 285
Ala Asp Ala Glu Arg Met Leu Ala Thr Ile Met Phe Thr Asp Ile Val
                    290                 295                 300
Gly Ser Thr Gln His Ala Ala Ala Leu Gly Asp Asp Arg Trp Arg Asp
305                 310                 315                 320
Leu Leu Asp Asn His Asp Thr Ile Val Cys His Glu Ile Gln Arg Phe
                    325                 330                 335
Gly Gly Arg Glu Val Asn Thr Ala Gly Asp Gly Phe Val Ala Thr Phe
                    340                 345                 350
Thr Ser Pro Ser Ala Ala Ile Ala Cys Ala Asp Asp Ile Val Asp Ala
                    355                 360                 365
Val Ala Ala Leu Gly Ile Glu Val Arg Ile Gly Ile His Ala Gly Glu
                    370                 375                 380
Val Glu Val Arg Asp Ala Ser His Gly Thr Asp Val Ala Gly Val Ala
385                 390                 395                 400
Val His Ile Gly Ala Arg Val Cys Ala Leu Ala Gly Pro Ser Glu Val
                    405                 410                 415
Leu Val Ser Ser Thr Val Arg Asp Ile Val Ala Gly Ser Arg His Arg
                    420                 425                 430
Phe Ala Glu Arg Gly Glu Gln Glu Leu Lys Gly Val Pro Gly Arg Trp
                    435                 440                 445
```

```
Arg Leu Cys Val Leu Met Arg Asp Asp Ala Thr Arg Thr Arg
    450                 455                 460
```

```
<210> SEQ ID NO 3
<211> LENGTH: 1389
<212> TYPE: DNA
<213> ORGANISM: Mycobacterium tuberculosis H37Rv

<400> SEQUENCE: 3
gtggcgcagg ctccccacat tcacaggacc cgctacgcaa atgcggcga catggatatc      60
gcctaccagg tgctgggtga cggtccgacg gatctgctgg tgttgccggg gccgttcgtg    120
ccgatcgact cgatcgacga cgagccatcg ctgtaccgtt tccatcgccg tcttgcgtca    180
ttcagcaggg tgatccgcct cgaccatcgt ggggtcggcc tgtcgtcacg gctcgccgcg    240
ataaccacgc tggggccgaa gttctgggcc aggacgcga tcgcggtgat ggacgcggtc    300
ggatgcgagc aggcgacaat tttcgcgccc agtttccacg ccatgaacgg acttgttctc    360
gccgccgact accccgagcg ggtgcgcagc ctgatcgtcg tcaacggctc ggcgcgccca    420
ctatgggcgc ccgactaccc ggtaggcgcc caggttcgtc gagctgaccc gttcctgacg    480
gtggcgctgg aaccgatgc cgtcgagcgg ggcttcgacg tgctgagcat cgtggctcct    540
accgtggccg agatgacgt gtttcgagcc tggtgggatc tcgccggcaa ccgtgccgga    600
ccgccgagca ttgcccgtgc cgtttcaaag gtcatagccg aggccgacgt acgagatgtc    660
ttgggacaca tcgaggctcc aacactgatc ttgcaccgtg tcggatcgac gtacatcccg    720
gtgggacatg gtcgctacct cgccgagcac atcgctggat cccgcttggt cgaactaccc    780
ggcaccgata ccctgtactg ggttggcgac accgggccga tgctcgatga aatcgaggaa    840
ttcatcaccg gcgtgcgcgg cggcgctgac gccgagcgca tgcttgccac catcatgttt    900
accgacatcg tcggctcgac ccagcacgcc gccgcgctcg gcgacgaccg atggcgcgac    960
ctgttggaca ccacgacac catcgtgtgc cacgaaatcc agcggttcgg cggtcgcgaa   1020
gtgaacacgg ccggtgacgg tttcgtcgcg acgttcacca gtccgagtgc cgcgatcgcg   1080
tgcgcggaca catcgtcga cgcggtcgcc gcgctgggta ttgaggtccg gatcggtatt   1140
catgcgggcg aggtcgaggt gcgcgatgcc tcgcacggta ccgacgtcgc cggcgtggcc   1200
gtgcatatcg gtgcgcgcgt ctgcgcgctg gccggaccca gtgaggtgct ggtgtcctcg   1260
accgtgcgag acatcgtcgc cggatcacgg caccggttcg ccgagcgtgg tgagcaggaa   1320
ctcaagggcg taccgggcag atggcggcta tgcgtgctca tgcgcgacga cgccacccgc   1380
acgcgctaa                                                           1389
```

```
<210> SEQ ID NO 4
<211> LENGTH: 462
<212> TYPE: PRT
<213> ORGANISM: Mycobacterium bovis AF2122/97

<400> SEQUENCE: 4

Met Ala Gln Ala Pro His Ile His Arg Thr Arg Tyr Ala Lys Cys Gly
1               5                   10                  15

Asp Met Asp Ile Ala Tyr Gln Val Leu Gly Asp Gly Pro Thr Asp Leu
            20                  25                  30

Leu Val Leu Pro Gly Pro Phe Val Pro Ile Asp Ser Ile Asp Asp Glu
        35                  40                  45

Pro Ser Leu Tyr Arg Phe His Arg Arg Leu Ala Ser Phe Ser Arg Val
    50                  55                  60
```

Ile Arg Leu Asp His Arg Gly Val Gly Leu Ser Ser Arg Leu Ala Ala
65                  70                  75                  80

Ile Thr Thr Leu Gly Pro Lys Phe Trp Ala Gln Asp Ala Ile Ala Val
                85                  90                  95

Met Asp Ala Val Gly Cys Glu Gln Ala Thr Ile Phe Ala Pro Ser Phe
            100                 105                 110

His Ala Met Asn Gly Leu Val Leu Ala Ala Asp Tyr Pro Glu Arg Val
            115                 120                 125

Arg Ser Leu Ile Val Val Asn Gly Ser Ala Arg Pro Leu Trp Ala Pro
130                 135                 140

Asp Tyr Pro Val Gly Ala Gln Val Arg Arg Ala Asp Pro Phe Leu Thr
145                 150                 155                 160

Val Ala Leu Glu Pro Asp Ala Val Glu Gln Gly Phe Asp Val Leu Ser
                165                 170                 175

Ile Val Ala Pro Thr Val Ala Gly Asp Asp Val Phe Arg Ala Trp Trp
            180                 185                 190

Asp Leu Ala Gly Asn Arg Ala Gly Pro Pro Ser Met Ala Arg Ala Val
            195                 200                 205

Ser Lys Val Ile Ala Glu Ala Asp Val Arg Asp Val Leu Gly His Ile
210                 215                 220

Glu Ala Pro Thr Leu Ile Leu His Arg Val Gly Ser Thr Tyr Ile Pro
225                 230                 235                 240

Val Gly His Gly Arg Tyr Leu Ala Glu His Ile Ala Gly Ser Arg Leu
                245                 250                 255

Val Glu Leu Pro Gly Thr Asp Thr Leu Tyr Trp Val Gly Asp Thr Gly
            260                 265                 270

Pro Met Leu Asp Glu Ile Glu Glu Phe Ile Thr Gly Val Arg Gly Gly
            275                 280                 285

Ala Asp Ala Glu Arg Met Leu Ala Thr Ile Met Phe Thr Asp Ile Val
290                 295                 300

Gly Ser Thr Gln His Ala Ala Leu Gly Asp Asp Arg Trp Arg Asp
305                 310                 315                 320

Leu Leu Asp Asn His Asp Thr Ile Val Cys His Glu Ile Gln Arg Phe
                325                 330                 335

Gly Gly Arg Glu Val Asn Thr Ala Gly Asp Gly Phe Val Ala Thr Phe
            340                 345                 350

Thr Ser Pro Ser Ala Ala Ile Ala Cys Ala Asp Asp Ile Val Asp Ala
            355                 360                 365

Val Ala Ala Leu Gly Ile Glu Val Arg Ile Gly Ile His Ala Gly Glu
370                 375                 380

Val Glu Val Arg Asp Ala Ser His Gly Thr Asp Val Ala Gly Val Ala
385                 390                 395                 400

Val His Ile Gly Ala Arg Val Cys Ala Leu Ala Gly Pro Ser Glu Val
                405                 410                 415

Leu Val Ser Ser Thr Val Arg Asp Ile Val Ala Gly Ser Arg His Arg
            420                 425                 430

Phe Ala Glu Arg Gly Glu Gln Glu Leu Lys Gly Val Pro Gly Arg Trp
            435                 440                 445

Arg Leu Cys Val Leu Met Arg Asp Asp Ala Thr Arg Thr Arg
450                 455                 460

<210> SEQ ID NO 5
<211> LENGTH: 1389

```
<212> TYPE: DNA
<213> ORGANISM: Mycobacterium bovis AF2122/97

<400> SE

-continued

```
Met Asp Ala Val Gly Cys Glu Gln Ala Thr Ile Phe Ala Pro Ser Phe
            100                 105                 110

His Ala Met Asn Gly Leu Val Leu Ala Ala Asp Tyr Pro Glu Arg Val
        115                 120                 125

Arg Ser Leu Ile Val Val Asn Gly Ser Ala Arg Pro Leu Trp Ala Pro
    130                 135                 140

Asp Tyr Pro Val Gly Ala Gln Val Arg Arg Ala Asp Pro Phe Leu Thr
145                 150                 155                 160

Val Ala Leu Glu Pro Asp Ala Val Glu Arg Gly Phe Asp Val Leu Ser
                165                 170                 175

Ile Val Ala Pro Thr Val Ala Gly Asp Val Phe Arg Ala Trp Trp
            180                 185                 190

Asp Leu Ala Gly Asn Arg Ala Gly Pro Pro Ser Met Ala Arg Ala Val
        195                 200                 205

Ser Lys Val Ile Ala Glu Ala Asp Val Arg Asp Val Leu Gly His Ile
    210                 215                 220

Glu Ala Pro Thr Leu Ile Leu His Arg Val Gly Ser Thr Tyr Ile Pro
225                 230                 235                 240

Val Gly His Gly Arg Tyr Leu Ala Glu His Ile Ala Gly Ser Arg Leu
                245                 250                 255

Val Glu Leu Pro Gly Thr Asp Thr Leu Tyr Trp Val Gly Asp Thr Gly
            260                 265                 270

Pro Met Leu Asp Glu Ile Glu Phe Ile Thr Gly Val Arg Gly Gly
        275                 280                 285

Ala Asp Ala Glu Arg Met Leu Ala Thr Ile Met Phe Thr Asp Ile Val
    290                 295                 300

Gly Ser Thr Gln His Ala Ala Ala Leu Gly Asp Asp Arg Trp Arg Asp
305                 310                 315                 320

Leu Leu Asp Asn His Asp Thr Ile Val Cys His Glu Ile Gln Arg Phe
                325                 330                 335

Gly Gly Arg Glu Val Asn Thr Ala Gly Asp Gly Phe Val Ala Thr Phe
            340                 345                 350

Thr Ser Pro Ser Ala Ala Ile Ala Cys Ala Asp Asp Ile Val Asp Ala
        355                 360                 365

Val Ala Ala Leu Gly Ile Glu Val Arg Ile Gly Ile His Ala Gly Glu
    370                 375                 380

Val Glu Val Arg Asp Ala Ser His Gly Thr Asp Val Ala Gly Val Ala
385                 390                 395                 400

Val His Ile Gly Ala Arg Val Cys Ala Leu Ala Gly Pro Ser Glu Val
                405                 410                 415

Leu Val Ser Ser Thr Val Arg Asp Ile Val Ala Gly Ser Arg His Arg
            420                 425                 430

Phe Ala Glu Arg Gly Glu Gln Glu Leu Lys Gly Val Pro Gly Arg Trp
        435                 440                 445

Arg Leu Cys Val Leu Met Arg Asp Asp Ala Thr Arg Thr Arg
    450                 455                 460
```

<210> SEQ ID NO 7
<211> LENGTH: 1389
<212> TYPE: DNA
<213> ORGANISM: Mycobacterium bovis BCG str. Pasteur 1173P2

<400> SEQUENCE: 7
gtggcgcagg ctccccacat tcacaggacc cgctacgcaa aatgcggcga catggatatc 60

```
gcctaccagg tgctgggtga cggtccgacg gatctgctgg tgttgccggg gccgttcgtg    120
ccgatcgact cgatcgacga cgagccatcg ctgtaccgtt ccatcgccg tcttgcgtca    180 ttcagcaggg tgatccgcct cgaccatcgt ggggtcggcc tgtcgtcacg gctcgccgcg    240
ataaccacgc tggggccgaa gttctgggcc caggacgcga tcgcggtgat ggacgcggtc    300
ggatgcgagc aggcgacaat tttcgcgccc agtttccacg ccatgaacgg acttgttctc    360
gccgccgact accccgagcg ggtgcgcagc ctgatcgtcg tcaacggctc ggcgcgccca    420
ctatgggcgc ccgactaccc ggtaggcgcc caggttcgtc gagctgaccc gttcctgacg    480
gtggcgctgg aaccggatgc cgtcgagcgg gcttcgacg tgctgagcat cgtggctcct    540
accgtggccg gagatgacgt gtttcgagcc tggtgggatc tcgccggcaa ccgtgccgga    600
ccgccgagca tggcccgtgc cgtttcaaag gtcatagccg aggccgacgt acgagatgtc    660
ttgggacaca tcgaggctcc aacactgatc ttgcaccgtg tcggatcgac gtacatcccg    720
gtgggacatg gtcgctacct cgccgagcac atcgctggat cccgcttggt cgaactaccc    780
ggcaccgata ccctgtactg ggttggcgac accgggccga tgctcgatga aatcgaggaa    840
ttcatcaccg gcgtgcgcgg cggcgctgac gccgagcgca tgcttgccac catcatgttt    900
accgacatcg tcggctcgac ccagcacgcc gccgcgctcg cgacgaccg atggcgcgac    960 ctgttggaca accacgacac catcgtgtgc cacgaaatcc agcggttcgg cggtcgcgaa    1020
gtgaacacgg ccggtgacgg tttcgtcgcg acgttcacca gtccgagtgc cgcgatcgcg    1080
tgcgcggacg acatcgtcga cgcggtcgcc gcgctgggta ttgaggtccg gatcggtatt    1140
catgcgggcg aggtcgaggt gcgcgatgcc tcgcacggta ccgacgtcgc cggcgtggcc    1200
gtgcatatcg gtgcgcgcgt ctgcgcgctg gccggaccca gtgaggtgct ggtgtcctcg    1260
accgtgcgag acatcgtcgc cggatcacgg caccggttcg ccgagcgtgg tgagcaggaa    1320
ctcaagggcg taccgggcag atggcggcta tgcgtgctca tgcgcgacga cgccacccgc    1380
acgcgctaa                                                            1389
```

<210> SEQ ID NO 8
<211> LENGTH: 462
<212> TYPE: PRT
<213> ORGANISM: Mycobacterium bovis BCG str. Tokyo 172

<400> SEQUENCE: 8

Met Ala Gln Ala Pro His Ile His Arg Thr Arg Tyr Ala Lys Cys Gly
1               5                   10                  15

Asp Met Asp Ile Ala Tyr Gln Val Leu Gly Asp Gly Pro Thr Asp Leu
            20                  25                  30

Leu Val Leu Pro Gly Pro Phe Val P

|     |     |     |     | 130 |     |     |     | 135 |     |     |     | 140 |     |
| --- | --- | --- | --- | --- | --- | --- | --- | --- | --- | --- | --- | --- | --- |

Asp Tyr Pro Val Gly Ala Gln Val Arg Arg Ala Asp Pro Phe Leu Thr
145                 150                 155                 160

Val Ala Leu Glu Pro Asp Ala Val Glu Arg Gly Phe Asp Val Leu Ser
                165                 170                 175

Ile Val Ala Pro Thr Val Ala Gly Asp Asp Val Phe Arg Ala Trp Trp
            180                 185                 190

Asp Leu Ala Gly Asn Arg Ala Gly Pro Pro Ser Met Ala Arg Ala Val
        195                 200                 205

Ser Lys Val Ile Ala Glu Ala Asp Val Arg Asp Val Leu Gly His Ile
    210                 215                 220

Glu Ala Pro Thr Leu Ile Leu His Arg Val Gly Ser Thr Tyr Ile Pro
225                 230                 235                 240

Val Gly His Gly Arg Tyr Leu Ala Glu His Ile Ala Gly Ser Arg Leu
                245                 250                 255

Val Glu Leu Pro Gly Thr Asp Thr Leu Tyr Trp Val Gly Asp Thr Gly
            260                 265                 270

Pro Met Leu Asp Glu Ile Glu Glu Phe Ile Thr Gly Val Arg Gly Gly
        275                 280                 285

Ala Asp Ala Glu Arg Met Leu Ala Thr Ile Met Phe Thr Asp Ile Val
290                 295                 300

Gly Ser Thr Gln His Ala Ala Ala Leu Gly Asp Asp Arg Trp Arg Asp
305                 310                 315                 320

Leu Leu Asp Asn His Asp Thr Ile Val Cys His Glu Ile Gln Arg Phe
                325                 330                 335

Gly Gly Arg Glu Val Asn Thr Ala Gly Asp Gly Phe Val Ala Thr Phe
            340                 345                 350

Thr Ser Pro Ser Ala Ala Ile Ala Cys Ala Asp Asp Ile Val Asp Ala
        355                 360                 365

Val Ala Ala Leu Gly Ile Glu Val Arg Ile Gly Ile His Ala Gly Glu
    370                 375                 380

Val Glu Val Arg Asp Ala Ser His Gly Thr Asp Val Ala Gly Val Ala
385                 390                 395                 400

Val His Ile Gly Ala Arg Val Cys Ala Leu Ala Gly Pro Ser Glu Val
                405                 410                 415

Leu Val Ser Ser Thr Val Arg Asp Ile Val Ala Gly Ser Arg His Arg
            420                 425                 430

Phe Ala Glu Arg Gly Glu Gln Glu Leu Lys Gly Val Pro Gly Arg Trp
        435                 440                 445

Arg Leu Cys Val Leu Met Arg Asp Asp Ala Thr Arg Thr Arg
450                 455                 460

<210> SEQ ID NO 9
<211> LENGTH: 1389
<212> TYPE: DNA
<213> ORGANISM: Mycobacterium bovis BCG str. Tokyo 172

<400> SEQUENCE: 9

```
gtggcgcagg ctccccacat tcacaggacc cgctacgcaa aatgcggcga catggatatc     60
gcctaccagg tgctgggtga cggtccgacg gatctgctgg tgttgccggg gccgttcgtg    120
ccgatcgact cgatcgacga cgagccatcg ctgtaccgtt tccatcgccg tcttgcgtca    180
ttcagcaggg tgatccgcct cgaccatcgt ggggtcggcc tgtcgtcacg gctcgccgcg    240
ataaccacgc tggggccgaa gttctgggcc caggacgcga tcgcggtgat ggacgcggtc    300
```

-continued

```
ggatgcgagc aggcgacaat tttcgcgccc agtttccacg ccatgaacgg acttgttctc    360
gccgccgact accccgagcg ggtgcgcagc ctgatcgtcg tcaacggctc ggcgcgccca    420
ctatgggcgc ccgactaccc ggtaggcgcc caggttcgtc gagctgaccc gttcctgacg    480
gtggcgctgg aaccggatgc cgtcgagcgg ggcttcgacg tgctgagcat cgtggctcct    540
accgtggccg gagatgacgt gtttcgagcc tggtgggatc tcgccggcaa ccgtgccgga    600
ccgccgagca tggcccgtgc cgtttcaaag gtcatagccg aggccgacgt acgagatgtc    660
ttgggacaca tcgaggctcc aacactgatc ttgcaccgtg tcggatcgac gtacatcccg    720
gtgggacatg gtcgctacct cgccgagcac atcgctggat cccgcttggt cgaactaccc    780
ggcaccgata ccctgtactg ggttggcgac accgggccga tgctcgatga aatcgaggaa    840
ttcatcaccg gcgtgcgcgg cggcgctgac gccgagcgca tgcttgccac catcatgttt    900
accgacatcg tcggctcgac ccagcacgcc gccgcgctcg gcgacgaccg atggcgcgac    960
ctgttggaca accacgacac catcgtgtgc cacgaaatcc agcggttcgg cggtcgcgaa    1020
gtgaacacgg ccggtgacgg tttcgtcgcg acgttcacca gtccgagtgc cgcgatcgcg    1080
tgcgcggaca catcgtcga cgcggtcgcc cgctgggta ttgaggtccg gatcggtatt    1140
catgcgggcg aggtcgaggt gcgcgatgcc tcgcacggta ccgacgtcgc cggcgtggcc    1200
gtgcatatcg gtgcgcgcgt ctgcgcgctg gccggaccca gtgaggtgct ggtgtcctcg    1260
accgtgcgag acatcgtcgc cggatcacgg caccggttcg ccgagcgtgg tgagcaggaa    1320
ctcaagggcg taccgggcag atggcggcta tgcgtgctca tgcgcgacga cgccacccgc    1380
acgcgctaa                                                             1389
```

<210> SEQ ID NO 10
<211> LENGTH: 462
<212> TYPE: PRT
<213> ORGANISM: Mycobacterium tuberculosis H37Ra

<400> SEQUENCE: 10

```
Met Ala Gln Ala Pro His Ile His Arg Thr Arg Tyr Ala Lys Cys Gly
1               5                   10                  15

Asp Met Asp Ile Ala Tyr Gln Val Leu Gly Asp Gly Pro Thr Asp Leu
            20                  25                  30

Leu Val Leu Pro Gly Pro Phe Val Pro Ile Asp Ser Ile Asp Asp Glu
        35                  40                  45

Pro Ser Leu Tyr Arg Phe His Arg Arg Leu Ala Ser Phe Ser Arg Val
    50                  55                  60

Ile Arg Leu Asp His Arg Gly Val Gly Leu Ser Ser Arg Leu Ala Ala
65                  70                  75                  80

Ile Thr Thr Leu Gly Pro Lys Phe Trp Ala Gln Asp Ala Ile Ala Val
                85                  90                  95

Met Asp Ala Val Gly Cys Glu Gln Ala Thr Ile Phe Ala Pro Ser Phe
            100                 105                 110

His Ala Met Asn Gly Leu Val Leu Ala Ala Asp Tyr Pro Glu Arg Val
        115                 120                 125

Arg Ser Leu Ile Val Val Asn Gly Ser Ala Arg Pro Leu Trp Ala Pro
    130                 135                 140

Asp Tyr Pro Val Gly Ala Gln Val Arg Arg Ala Asp Pro Phe Leu Thr
145                 150                 155                 160

Val Ala Leu Glu Pro Asp Ala Val Glu Arg Gly Phe Asp Val Leu Ser
                165                 170                 175
```

```
Ile Val Ala Pro Thr Val Ala Gly Asp Asp Val Phe Arg Ala Trp Trp
            180                 185                 190

Asp Leu Ala Gly Asn Arg Ala Gly Pro Pro Ser Ile Ala Arg Ala Val
        195                 200                 205

Ser Lys Val Ile Ala Glu Ala Asp Val Arg Asp Val Leu Gly His Ile
210                 215                 220

Glu Ala Pro Thr Leu Ile Leu His Arg Val Gly Ser Thr Tyr Ile Pro
225                 230                 235                 240

Val Gly His Gly Arg Tyr Leu Ala Glu His Ile Ala Gly Ser Arg Leu
                245                 250                 255

Val Glu Leu Pro Gly Thr Asp Thr Leu Tyr Trp Val Gly Asp Thr Gly
            260                 265                 270

Pro Met Leu Asp Glu Ile Glu Glu Phe Ile Thr Gly Val Arg Gly Gly
        275                 280                 285

Ala Asp Ala Glu Arg Met Leu Ala Thr Ile Met Phe Thr Asp Ile Val
290                 295                 300

Gly Ser Thr Gln His Ala Ala Leu Gly Asp Asp Arg Trp Arg Asp
305                 310                 315                 320

Leu Leu Asp Asn His Asp Thr Ile Val Cys His Glu Ile Gln Arg Phe
                325                 330                 335

Gly Gly Arg Glu Val Asn Thr Ala Gly Asp Gly Phe Val Ala Thr Phe
            340                 345                 350

Thr Ser Pro Ser Ala Ala Ile Ala Cys Ala Asp Asp Ile Val Asp Ala
        355                 360                 365

Val Ala Leu Gly Ile Glu Val Arg Ile Gly Ile His Ala Gly Glu
370                 375                 380

Val Glu Val Arg Asp Ala Ser His Gly Thr Asp Val Ala Gly Val Ala
385                 390                 395                 400

Val His Ile Gly Ala Arg Val Cys Ala Leu Ala Gly Pro Ser Glu Val
                405                 410                 415

Leu Val Ser Ser Thr Val Arg Asp Ile Val Ala Gly Ser Arg His Arg
            420                 425                 430

Phe Ala Glu Arg Gly Glu Gln Glu Leu Lys Gly Val Pro Gly Arg Trp
        435                 440                 445

Arg Leu Cys Val Leu Met Arg Asp Asp Ala Thr Arg Thr Arg
450                 455                 460

<210> SEQ ID NO 11
<211> LENGTH: 1389
<212> TYPE: DNA
<213> ORGANISM: Mycobacterium tuberculosis H37Ra

<400> SEQUENCE: 11
gtggcgcagg ctccccacat tcacaggacc cgctacgcaa aatgcggcga catggatatc      60
gcctaccagg tgctgggtga cggtccgacg gatctgctgg tgttgccggg gccgttcgtg     120
ccgatcgact cgatcgacga cgagccatcg ctgtaccgtt ccatcgccg tcttgcgtca     180 ttcagcaggg tgatccgcct cgaccatcgt ggggtcggcc tgtcgtcacg gctcgccgcg     240 ataaccacg tggggccgaa gttctgggcc caggacgcga tcgcggtgat ggacgcggtc     300
ggatgcgagc aggcgacaat tttcgcgccc agtttccacg ccatgaacgg acttgttctc     360
gccgccgact accccgagcg ggtgcgcagc ctgatcgtcg tcaacggctc ggcgcgccca     420
ctatgggcgc ccgactaccc ggtaggcgcc caggttcgtc gagctgaccc gttcctgacg     480
```

```
gtggcgctgg aaccggatgc cgtcgagcgg ggcttcgacg tgctgagcat cgtggctcct    540
accgtggccg gagatgacgt gtttcgagcc tggtgggatc tcgccggcaa ccgtgccgga    600
ccgccgagca ttgcccgtgc cgtttcaaag gtcatagccg aggccgacgt acgagatgtc    660
ttgggacaca tcgaggctcc aacactgatc ttgcaccgtg tcggatcgac gtacatcccg    720
gtgggacatg gtcgctacct cgccgagcac atcgctggat cccgcttggt cgaactaccc    780
ggcaccgata ccctgtactg ggttggcgac accgggccga tgctcgatga aatcgaggaa    840
ttcatcaccg gcgtgcgcgg cggcgctgac gccgagcgca tgcttgccac catcatgttt    900
accgacatcg tcggctcgac ccagcacgcc gccgcgctcg gcgacgaccg atggcgcgac    960
ctgttggaca accacgacac catcgtgtgc cacgaaatcc agcggttcgg cggtcgcgaa   1020
gtgaacacgg ccggtgacgg tttcgtcgcg acgttcacca gtccgagtgc cgcgatcgcg   1080
tgcgcggacg acatcgtcga cgcggtcgcc cgcctgggta ttgaggtccg gatcggtatt   1140
catgcgggcg aggtcgaggt gcgcgatgcc tcgcacggta ccgacgtcgc cggcgtggcc   1200
gtgcatatcg gtgcgcgcgt ctgcgcgctg gccggaccca gtgaggtgct ggtgtcctcg   1260
accgtgcgag acatcgtcgc cggatcacgg caccggttcg ccgagcgtgg tgagcaggaa   1320
ctcaagggcg taccgggcag atggcggcta tgcgtgctca tgcgcgacga cgccacccgc   1380
acgcgctaa                                                           1389
```

<210> SEQ ID NO 12
<211> LENGTH: 458
<212> TYPE: PRT
<213> ORGANISM: Mycobacterium ulcerans Agy99

<400> SEQUENCE: 12

Met Ser Gln Ala Pro Arg Thr Pro Arg Thr Arg Tyr Ala Arg Cys Gly
1               5                   10                  15

Asp Leu Asp Ile Ala Tyr Gln Val Ile Gly Asp His Pro Ile Asp Leu
                20                  25                  30

Leu Val Ile Pro Gly Ala Ser Ile Pro Val Asp Thr Ile Asp Ser Glu
            35                  40                  45

Pro Ser Met Tyr Arg Phe His Arg Arg Leu Ala Ser Phe Ser Arg Leu
        50                  55                  60

Ile Arg Phe Asp His Arg Gly Val Gly Leu Ser Ser Arg Val Ser Ser
65                  70                  75                  80

Pro Asp Ala Leu Gly Pro Arg Phe Trp Ala Glu Asp Ala Ile Ala Val
                85                  90                  95

Met Asp Ala Ala Gly Cys Gln Gln Ala Thr Ile Leu Ala Ser Gly Phe
            100                 105                 110

Thr Ala Thr Thr Ala Leu Val Leu Ala Ala Asp Tyr Pro Glu Arg Val
        115                 120                 125

Arg Ser Leu Val Leu Ile Asn Ala Ser Ala Arg Thr Leu His Ala Pro
    130                 135                 140

Asp Tyr Glu Leu Gly Ile Arg Ser Asn Thr Ala Glu Pro Phe Leu Thr
145                 150                 155                 160

Leu Gly Thr Asp Pro Asp Ala Val Glu Gln Gly Phe Asp Val Leu Arg
                165                 170                 175

Ile Met Ala Pro Ser Val Ala His Asp Ala Phe Arg His Trp Trp
            180                 185                 190

Asp Leu Ala Gly Asn Arg Ala Ala Ser Pro Ser Thr Ala Arg Ala Phe
        195                 200                 205

Ile Asn Ala Val Gln Ala Ser Asp Ala Arg Asp Ser Leu Pro His Ile
210                 215                 220

Thr Ala Pro Thr Leu Ile Leu His Arg Val Gly Thr Lys Phe Val Pro
225                 230                 235                 240

Val Glu His Gly Arg Tyr Leu Ala Glu His Ile Ala Gly Ser Arg Leu
            245                 250                 255

Val Glu Leu Pro Gly Ser Asp Ser Leu Tyr Trp Val Gly Asp Thr Ala
            260                 265                 270

Ala Leu Leu Asp Glu Val Glu Glu Phe Ile Thr Gly Val Arg Gly Gly
        275                 280                 285

Phe Val Thr Glu Arg Val Leu Thr Ala Val Met Phe Thr Gly Ile Val
290                 295                 300

Gly Ser Thr Gln Arg Ala Ala Thr Val Gly Asp Leu Arg Trp Arg Asp
305                 310                 315                 320

Leu Leu Asp Asn His Asp Asn Leu Val Arg His Glu Ile Gln Arg Phe
                325                 330                 335

Gly Gly Arg Glu Val Asn Thr Ala Gly Asp Gly Phe Val Ala Thr Phe
            340                 345                 350

Ser Ser Pro Ser Ala Ala Ile Asn Cys Ala Asp Ala Val Val Asp Ala
        355                 360                 365

Val Ala Val Leu Gly Ile Glu Val Arg Val Gly Ile His Ala Gly Glu
370                 375                 380

Val Glu Val Arg Gly Ala Asp Val Ala Asp Leu Ala Val His Ile Gly
385                 390                 395                 400

Ala Arg Val Cys Ala Leu Ala Gly Ser Ser Glu Val Leu Val Ser Ser
                405                 410                 415

Thr Val Arg Asp Ile Val Thr Gly Ser Ser His Arg Phe Ala Glu Arg
            420                 425                 430

Gly Glu His Glu Leu Lys Gly Val Pro Gly Arg Trp Arg Leu Cys Ala
        435                 440                 445

Leu Val Arg Glu His Leu Thr Gly Gln Arg
    450                 455

<210> SEQ ID NO 13
<211> LENGTH: 1377
<212> TYPE: DNA
<213> ORGANISM: Mycobacterium ulcerans Agy99

<400> SEQUENCE: 13
gtgtcgcagg cgccccgaac tccccggact cgctacgcca ggtgcggcga cctggacatc      60
gcctaccagg tgatcgggga tcatccgatc gacctgctcg tcataccggg ggcctcgatt     120
ccggtcgaca ccatcgattc cgaaccgtcg atgtaccgct tcaccgccg tctggcgtcg      180 ttttcccgcc tgatccggtt cgaccatcgc ggcgtcggcc tgtcatcgcg ggtttcgtcg     240
ccggatgcgc tcggcccgag gttctgggcc gaggatgcga ttgcggtgat ggacgcggcc     300
ggatgccagc aagccacgat tcttgcctcc gggttcaccg cgacgaccgc cctggtgctg     360
gccgccgact atcccgagcg ggtgcgcagc ctggtgctca tcaacgcctc cgcgcggaca     420
ctgcatgcgc ccgactacga actgggcatc aggtccaaca ccgccgaacc attcctcacc     480
ctcggaaccg atcccgacgc ggtcgagcag gggttcgacg tgctgcgcat catggcgccc     540
agtgtggccc atgacgacgc gttccgccac tggtgggatc tggccggaaa ccgggcggcc     600
tcgcccagca cggcgcgcgc cttcatcaac gcggttcaag cctcggatgc gcgcgactcg     660
ctgccccaca tcaccgcgcc gacgctgatc ctgcatcggg tgggcaccaa gttcgttccg     720

-continued

```
gtcgagcacg gccgctatct ggccgagcac attgccgggt cgcgcttggt cgagcttccc    780
ggttccgatt ccttgtattg ggtcggcgac accgccgcgt tgctcgacga ggtcgaggag    840
ttcatcaccg gcgtccgggg cggcttcgtc accgagcggg tactgaccgc ggtcatgttc    900
accggcatcg tcggctcgac ccagcgcgcg gccaccgtgg gtgacctgcg ctggcgcgac    960
ctgctcgata accacgacaa cctggtccgc cacgagatcc agcggttcgg tgggcgcgag   1020
gtcaataccg cggggcgacgg gttcgtcgcg acgttcagca gcccgagtgc ggcaatcaac   1080
tgcgcggacg ccgtcgtcga cgccgtcgcg gtgctcggca tcgaggtccg ggtggggatt   1140
catgccggcg aggtcgaggt gcgggggggcc gacgtcgccg acctggccgt acacatcggt   1200
gcccgggtct gtgcgctggc cggctccagt gaggtgctgg tgtcctcgac ggtgcgtgac   1260
atcgtcaccg gctcgagcca cagattcgcc gagcgcggcg aacacgaact caagggcgtg   1320
ccgggccgat ggcgactttg tgcgctggtc cgggagcacc tcacgggcca gcggtag      1377
```

<210> SEQ ID NO 14
<211> LENGTH: 458
<212> TYPE: PRT
<213> ORGANISM: Mycobacterium marinum M

<400> SEQUENCE: 14

```
Met Ser Gln Ala Pro Arg Thr Pro Arg Thr Arg Tyr Ala Arg Cys Gly
1               5                   10                  15

Asp Leu Asp Ile Ala Tyr Gln Val Ile Gly Asp His Pro Ile Asp Leu
                20                  25                  30

Leu Val Ile Pro Gly Ala Ser Ile Pro Val Asp Thr Ile Asp Ser Glu
            35                  40                  45

Pro Ser Met Tyr Arg Phe His Arg Arg Leu Ala Ser Phe Ser Arg Leu
        50                  55                  60

Ile Arg Phe Asp His Arg Gly Val Gly Leu Ser Ser Arg Val Ser Ser
65                  70                  75                  80

Pro Asp Ala Leu Gly Pro Arg Phe Trp Ala Glu Asp Ala Ile Ala Val
                85                  90                  95

Met Asp Ala Ala Gly Cys Gln Glu Ala Thr Ile Leu Ala Ser Gly Phe
            100                 105                 110

Thr Ala Thr Thr Ala Leu Val Leu Ala Ala Asp Tyr Pro Glu Arg Val
        115                 120                 125

Arg Ser Leu Val Leu Ile Asn Ala Ser Ala Arg Thr Leu His Ala Pro
    130                 135                 140

Asp Tyr Glu Leu Gly Ile Arg Ser Asn Thr Ala Glu Pro Phe Leu Thr
145                 150                 155                 160

Leu Gly Thr Asp Pro Asp Ala Val Glu Gln Gly Phe Asp Val Leu Arg
                165                 170                 175

Ile Met Ala Pro Ser Val Ala His Asp Asp Ala Phe Arg Asp Trp Trp
            180                 185                 190

Asp Leu Ala Gly Asn Arg Ala Ala Ser Pro Ser Thr Ala Arg Ala Phe
        195                 200                 205

Ile Asn Ala Val Gln Ala Ser Asp Ala Arg Asp Ser Leu Pro His Ile
    210                 215                 220

Thr Ala Pro Thr Leu Ile Leu His Arg Val Gly Thr Lys Phe Val Pro
225                 230                 235                 240

Val Glu His Gly Arg Tyr Leu Ala Glu His Ile Ala Gly Ser Arg Leu
                245                 250                 255
```

Val Glu Leu Pro Gly Ser Asp Ser Leu Tyr Trp Val Gly Asp Thr Ala
            260                 265                 270

Ala Leu Leu Asp Glu Val Glu Glu Phe Ile Thr Gly Val Arg Gly Gly
        275                 280                 285

Phe Val Thr Glu Arg Val Leu Thr Thr Val Met Phe Thr Asp Ile Val
    290                 295                 300

Gly Ser Thr Gln Arg Ala Ala Thr Val Gly Asp Leu Arg Trp Arg Asp
305                 310                 315                 320

Leu Leu Asp Asn His Asp Asn Leu Val Arg His Glu Ile Gln Arg Phe
                325                 330                 335

Gly Gly Arg Glu Val Asn Thr Ala Gly Asp Gly Phe Val Ala Thr Phe
            340                 345                 350

Ser Ser Pro Ser Ala Ala Ile Asn Cys Ala Asp Ala Val Val Asp Ala
        355                 360                 365

Val Ala Val Leu Gly Ile Glu Val Arg Val Gly Ile His Ala Gly Glu
    370                 375                 380

Val Glu Val Arg Gly Ala Asp Val Ala Gly Leu Ala Val His Ile Gly
385                 390                 395                 400

Ala Arg Val Cys Ala Leu Ala Gly Ser Ser Glu Val Leu Val Ser Ser
                405                 410                 415

Thr Val Arg Asp Ile Val Thr Gly Ser Ser His Arg Phe Ala Glu Arg
            420                 425                 430

Gly Glu His Glu Leu Lys Gly Val Pro Gly Arg Trp Arg Leu Cys Ala
        435                 440                 445

Leu Val Arg Glu His Leu Thr Gly Gln Arg
    450                 455

<210> SEQ ID NO 15
<211> LENGTH: 1377
<212> TYPE: DNA
<213> ORGANISM: Mycobacterium marinum M

<400> SEQUENCE: 15
gtgtcgcagg cgccccgaac tcccccggact cgctacgcca ggtgcggcga cctggacatc      60
gcctaccagg tgatcgggga tcatccgatc gacctgctcg tcataccggg ggcctcgatt     120
ccggtcgaca ccatcgattc cgaaccgtcg atgtaccgct tcaccgccg tctggcgtcg      180 ttttcccgcc tgatccggtt cgaccatcgc ggcgtcggcc tgtcatcgcg ggtttcgtcg     240
ccggatgcgc tcggcccgag gttctgggcc gaggatgcga ttgcggtgat ggacgcggcc     300
ggatgccagg aagccacgat tcttgcctcc gggttcaccg cgacgaccgc cctggtgctg     360
gccgccgact atcccgagcg ggtgcgcagc ctggtgctca tcaacgcctc cgcgcggaca     420
ctgcatgcgc ccgactacga actgggcatc aggtccaaca ccgccgaacc attcctcacc     480
ctcggaaccg atcccgacgc ggtcgagcag gggttcgacg tgctgcgcat catggcgccc     540
agcgtggccc atgacgacgc gttccgcgac tggtgggatc tggccggaaa ccgggcggcc     600
tcgcccagca cggcgcgcgc cttcatcaac gcggttcaag cctcggatgc gcgcgactcg     660
ctgccccaca tcaccgcgcc gacgctgatc ctgcatcggg tgggcaccaa gttcgttccg     720
gtcgagcacg gccgctatct ggccgagcac attgccgggt cgcgcttggt cgagcttccc     780
ggttccgatt ccttgtattg gtcggcgac accgccgcgt tgctcgacga ggtcgaggag     840
ttcatcaccg gcgtccgggg cggcttcgtc accgagcggg tactgaccac ggtcatgttc     900
accgacatcg tcggctcgac ccagcgcgca gccaccgtgg gtgacctgcg ctggcgcgac     960

```
ctgctcgata accacgacaa cctggtccgc cacgagatcc agcggttcgg t

```
Gly Ser Thr Gln His Ala Ala Leu Gly Asp Asp Arg Trp Arg Asp
305                 310                 315                 320

Leu Leu Asp Asn His Asp Thr Ile Val Cys His Glu Ile Gln Arg Phe
                325                 330                 335

Gly Gly Arg Glu Val Asn Thr Ala Gly Asp Gly Phe Val Ala Thr Phe
            340                 345                 350

Thr Ser Pro Ser Ala Ala Ile Ala Cys Ala Asp Ile Val Asp Ala
        355                 360                 365

Val Ala Ala Leu Gly Ile Glu Val Arg Ile Gly Ile His Ala Gly Glu
    370                 375                 380

Val Glu Val Arg Asp Ala Ser His Gly Thr Asp Val Ala Gly Val Ala
385                 390                 395                 400

Val His Ile Gly Ala Arg Val Cys Ala Leu Ala Gly Pro Ser Glu Val
                405                 410                 415

Leu Val Ser Ser Thr Val Arg Asp Ile Val Ala Gly Ser Arg His Arg
            420                 425                 430

Phe Ala Glu Arg Gly Glu Gln Glu Leu Lys Gly Val Pro Gly Arg Trp
        435                 440                 445

Arg Leu Cys Val Leu Met Arg Asp Asp Ala Thr Arg Thr Arg
    450                 455                 460

<210> SEQ ID NO 17
<211> LENGTH: 1389
<212> TYPE: DNA
<213> ORGANISM: Mycobacterium tuberculosis KZN 1435

<400> SEQUENCE: 17
gtggcgcagg ctcccccacat tcacaggacc cgctacgcaa aatgcggcga catggatatc      60
gcctaccagg tgctgggtga cggtccgacg gatctgctgg tgttgccggg gccgttcgtg     120
ccgatcgact cgatcgacga cgagccatcg ctgtaccgtt ccatcgccg tcttgcgtca     180 ttcagcaggg tgatccgcct cgaccatcgt ggggtcggcc tgtcgtcacg gctcgccgcg     240
ataaccacgc tggggccgaa gttctgggcc caggacgcga tcgcggtgat ggacgcggtc     300
ggatgcgagc aggcgacaat tttcgcgccc agtttccacg ccatgaacgg acttgttctc     360
gccgccgact accccgagcg ggtgcgcagc ctgatcgtcg tcaacggctc ggcgcgccca     420
ctatgggcgc ccgactaccc ggtaggcgcc caggttcgtc gagctgaccc gttcctgacg     480
gtggcgctgg aaccggatgc cgtcgagcgg ggcttcgacg tgctgagcat cgtggctcct     540
accgtggccg gagatgacgt gtttcgagcc tggtgggatc tcgccggcaa ccgtgccgga     600
ccgccgagca tggcccgtgc cgtttcaaag gtcatagccg aggccgacgt acgagatgtc     660
ttgggacaca tcgaggctcc aacactgatc ttgcaccgtg tcggatcgac gtacatcccg     720
gtgggacatg gtcgctacct cgccgagcac atcgctggat cccgcttggt cgaactaccc     780
ggcaccgata ccctgtactg ggttggcgac accgggccga tgctcgatga aatcgaggaa     840
ttcatcaccg gcgtgcgcgg cggcgctgac gccgagcgca tgcttgccac catcatgttt     900
accgacatcg tcggctcgac ccagcacgcc gccgcgctcg gcgacgaccg atggcgcgac     960
ctgttggaca ccacgacac catcgtgtgc cacgaaatcc agcggttcgg cggtcgcgaa    1020
gtgaacacgg ccggtgacgg tttcgtcgcg acgttcacca gtccgagtgc cgcgatcgcg    1080
tgcgcggacg acatcgtcga cgcggtcgcc gcgctgggta ttgaggtccg gatcggtatt    1140
catgcgggcg aggtcgaggt gcgcgatgcc tcgcacggta ccgacgtcgc cggcgtggcc    1200
gtgcatatcg gtgcgcgcgt ctgcgcgctg gccggaccca gtgaggtgct ggtgtcctcg    1260
```

```
accgtgcgag acatcgtcgc cggatcacgg caccggttcg ccgagcgtgg tgagcaggaa    1320
ctcaagggcg taccgggcag atggcggcta tgcgtgctca tgcgcgacga cgccacccgc    1380
acgcgctaa                                                            1389
```

```
<210> SEQ ID NO 18
<211> LENGTH: 462
<212> TYPE: PRT
<213> ORGANISM: Mycobacterium tuberculosis F11

<400> SEQUENCE: 18
```

| | | | | | | | | | | | | | | | |
|---|---|---|---|---|---|---|---|---|---|---|---|---|---|---|---|
| Met | Ala | Gln | Ala | Pro | His | Ile | His | Arg | Thr | Arg | Tyr | Ala | Lys | Cys | Gly |
| 1 | | | | 5 | | | | | 10 | | | | | 15 | |
| Asp | Met | Asp | Ile | Ala | Tyr | Gln | Val | Leu | Gly | Asp | Gly | Pro | Thr | Asp | Leu |
| | | | 20 | | | | | 25 | | | | | 30 | | |
| Leu | Val | Leu | Pro | Gly | Pro | Phe | Val | Pro | Ile | Asp | Ser | Ile | Asp | Asp | Glu |
| | | 35 | | | | | 40 | | | | | 45 | | | |
| Pro | Ser | Leu | Tyr | Arg | Phe | His | Arg | Arg | Leu | Ala | Ser | Phe | Ser | Arg | Val |
| | 50 | | | | | 55 | | | | | 60 | | | | |
| Ile | Arg | Leu | Asp | His | Arg | Gly | Val | Gly | Leu | Ser | Ser | Arg | Leu | Ala | Ala |
| 65 | | | | | 70 | | | | | 75 | | | | | 80 |
| Ile | Thr | Thr | Leu | Gly | Pro | Lys | Phe | Trp | Ala | Gln | Asp | Ala | Ile | Ala | Val |
| | | | | 85 | | | | | 90 | | | | | 95 | |
| Met | Asp | Ala | Val | Gly | Cys | Glu | Gln | Ala | Thr | Ile | Phe | Ala | Pro | Ser | Phe |
| | | | 100 | | | | | 105 | | | | | 110 | | |
| His | Ala | Met | Asn | Gly | Leu | Val | Leu | Ala | Ala | Asp | Tyr | Pro | Glu | Arg | Val |
| | | 115 | | | | | 120 | | | | | 125 | | | |
| Arg | Ser | Leu | Ile | Val | Val | Asn | Gly | Ser | Ala | Arg | Pro | Leu | Trp | Ala | Pro |
| | 130 | | | | | 135 | | | | | 140 | | | | |
| Asp | Tyr | Pro | Val | Gly | Ala | Gln | Val | Arg | Arg | Ala | Asp | Pro | Phe | Leu | Thr |
| 145 | | | | | 150 | | | | | 155 | | | | | 160 |
| Val | Ala | Leu | Glu | Pro | Asp | Ala | Val | Glu | Arg | Gly | Phe | Asp | Val | Leu | Ser |
| | | | | 165 | | | | | 170 | | | | | 175 | |
| Ile | Val | Ala | Pro | Thr | Val | Ala | Gly | Asp | Asp | Val | Phe | Arg | Ala | Trp | Trp |
| | | | 180 | | | | | 185 | | | | | 190 | | |
| Asp | Leu | Ala | Gly | Asn | Arg | Ala | Gly | Pro | Pro | Ser | Met | Ala | Arg | Ala | Val |
| | | 195 | | | | | 200 | | | | | 205 | | | |
| Ser | Lys | Val | Ile | Ala | Glu | Ala | Asp | Val | Arg | Asp | Val | Leu | Gly | His | Ile |
| | 210 | | | | | 215 | | | | | 220 | | | | |
| Glu | Ala | Pro | Thr | Leu | Ile | Leu | His | Arg | Val | Gly | Ser | Thr | Tyr | Ile | Pro |
| 225 | | | | | 230 | | | | | 235 | | | | | 240 |
| Val | Gly | His | Gly | Arg | Tyr | Leu | Ala | Glu | His | Ile | Ala | Gly | Ser | Arg | Leu |
| | | | | 245 | | | | | 250 | | | | | 255 | |
| Val | Glu | Leu | Pro | Gly | Thr | Asp | Thr | Leu | Tyr | Trp | Val | Gly | Asp | Thr | Gly |
| | | | 260 | | | | | 265 | | | | | 270 | | |
| Pro | Met | Leu | Asp | Glu | Ile | Glu | Glu | Phe | Ile | Thr | Gly | Val | Arg | Gly | Gly |
| | | 275 | | | | | 280 | | | | | 285 | | | |
| Ala | Asp | Ala | Glu | Arg | Met | Leu | Ala | Thr | Ile | Met | Phe | Thr | Asp | Ile | Val |
| | 290 | | | | | 295 | | | | | 300 | | | | |
| Gly | Ser | Thr | Gln | His | Ala | Ala | Leu | Gly | Asp | Asp | Arg | Trp | Arg | Asp |
| 305 | | | | | 310 | | | | | 315 | | | | | 320 |
| Leu | Leu | Asp | Asn | His | Asp | Thr | Ile | Val | Cys | His | Glu | Ile | Gln | Arg | Phe |
| | | | | 325 | | | | | 330 | | | | | 335 | |
| Gly | Gly | Arg | Glu | Val | Asn | Thr | Ala | Gly | Asp | Gly | Phe | Val | Ala | Thr | Phe |

```
            340             345             350
Thr Ser Pro Ser Ala Ala Ile Ala Cys Ala Asp Asp Ile Val Asp Ala
        355                 360                 365

Val Ala Ala Leu Gly Ile Glu Val Arg Ile Gly Ile His Ala Gly Glu
    370                 375                 380

Val Glu Val Arg Asp Ala Ser His Gly Thr Asp Val Ala Gly Val Ala
385                 390                 395                 400

Val His Ile Gly Ala Arg Val Cys Ala Leu Ala Gly Pro Ser Glu Val
                405                 410                 415

Leu Val Ser Ser Thr Val Arg Asp Ile Val Ala Gly Ser Arg His Arg
            420                 425                 430

Phe Ala Glu Arg Gly Glu Gln Glu Leu Lys Gly Val Pro Gly Arg Trp
        435                 440                 445

Arg Leu Cys Val Leu Met Arg Asp Asp Ala Thr Arg Thr Arg
        450                 455                 460

<210> SEQ ID NO 19
<211> LENGTH: 1389
<212> TYPE: DNA
<213> ORGANISM: Mycobacterium tuberculosis F11

<400> SEQUENCE: 19
gtggcgcagg ctccccacat tcacaggacc cgctacgcaa aatgcggcga catggatatc      60
gcctaccagg tgctgggtga cggtccgacg gatctgctgg tgttgccggg gccgttcgtg     120
ccgatcgact cgatcgacga cgagccatcg ctgtaccgtt ccatcgccg tcttgcgtca     180 ttcagcaggg tgatccgcct cgaccatcgt ggggtcggcc tgtcgtcacg gctcgccgcg     240
ataaccacgc tggggccgaa gttctgggcc caggacgcga tcgcggtgat ggacgcggtc     300
ggatgcgagc aggcgacaat tttcgcgccc agtttccacg ccatgaacgg acttgttctc     360
gccgccgact accccgagcg ggtgcgcagc ctgatcgtcg tcaacggctc ggcgcgccca     420
ctatgggcgc ccgactaccc ggtaggcgcc caggttcgtc gagctgaccc gttcctgacg     480
gtggcgctgg aaccggatgc cgtcgagcgg ggcttcgacg tgctgagcat cgtggctcct     540
accgtggccg gagatgacgt gtttcgagcc tggtgggatc tcgccggcaa ccgtgccgga     600
ccgccgagca tggcccgtgc cgtttcaaag gtcatagccg aggccgacgt acgagatgtc     660
ttgggacaca tcgaggctcc aacactgatc ttgcaccgtg tcggatcgac gtacatcccg     720
gtgggacatg gtcgctacct cgccgagcac atcgctggat cccgcttggt cgaactaccc     780
ggcaccgata ccctgtactg ggttggcgac accgggccga tgctcgatga aatcgaggaa     840
ttcatcaccg gcgtgcgcgg cggcgctgac gccgagcgca tgcttgccac catcatgttt     900
accgacatcg tcggctcgac ccagcacgcc gccgcgctcg cgacgaccg atggcgcgac     960 ctgttggaca accacgacac catcgtgtgc cacgaaatcc agcggttcgg cggtcgcgaa    1020
gtgaacacgg ccggtgacgg tttcgtcgcg acgttcacca gtccgagtgc cgcgatcgcg    1080
tgcgcggacg acatcgtcga cgcggtcgcc gcgctgggta ttgaggtccg gatcggtatt    1140
catgcgggcg aggtcgaggt gcgcgatgcc tcgcacggta ccgacgtcgc cggcgtggcc    1200
gtgcatatcg gtgcgcgcgt ctgcgcgctg gccggaccca gtgaggtgct ggtgtcctcg    1260
accgtgcgag acatcgtcgc cggatcacgg caccggttcg ccgagcgtgg tgagcaggaa    1320
ctcaagggcg taccgggcag atggcggcta tgcgtgctca tgcgcgacga cgccacccgc    1380
acgcgctaa                                                           1389
```

```
<210> SEQ ID NO 20
<211> LENGTH: 372
<212> TYPE: PRT
<213> ORGANISM: Phanerochaete chrysosporium

<400> SEQUENCE: 20

Met Ala Phe Lys Gln Leu Leu Ala Ala Leu Ser Val Ala Leu Thr Leu
1               5                   10                  15

Gln Val Thr Gln Ala Ala Pro Asn Leu Asp Lys Arg Val Ala Cys Pro
            20                  25                  30

Asp Gly Val His Thr Ala Ser Asn Ala Ala Cys Cys Ala Trp Phe Pro
        35                  40                  45

Val Leu Asp Asp Ile Gln Gln Asn Leu Phe His Gly Gly Gln Cys Gly
    50                  55                  60

Ala Glu Ala His Glu Ala Leu Arg Met Val Phe His Asp Ser Ile Ala
65                  70                  75                  80

Ile Ser Pro Lys Leu Gln Ser Gln Gly Lys Phe Gly Gly Gly Ala
                85                  90                  95

Asp Gly Ser Ile Ile Thr Phe Ser Ser Ile Glu Thr Thr Tyr His Pro
            100                 105                 110

Asn Ile Gly Leu Asp Glu Val Val Ala Ile Gln Lys Pro Phe Ile Ala
        115                 120                 125

Lys His Gly Val Thr Arg Gly Asp Phe Ile Ala Phe Ala Gly Ala Val
    130                 135                 140

Gly Val Ser Asn Cys Pro Gly Ala Pro Gln Met Gln Phe Phe Leu Gly
145                 150                 155                 160

Arg Pro Glu Ala Thr Gln Ala Ala Pro Asp Gly Leu Val Pro Glu Pro
                165                 170                 175

Phe His Thr Ile Asp Gln Val Leu Ala Arg Met Leu Asp Ala Gly Gly
            180                 185                 190

Phe Asp Glu Ile Glu Thr Val Trp Leu Leu Ser Ala His Ser Ile Ala
        195                 200                 205

Ala Ala Asn Asp Val Asp Pro Thr Ile Ser Gly Leu Pro Phe Asp Ser
    210                 215                 220

Thr Pro Gly Gln Phe Asp Ser Gln Phe Phe Val Glu Thr Gln Leu Arg
225                 230                 235                 240

Gly Thr Ala Phe Pro Gly Lys Thr Gly Ile Gln Gly Thr Val Met Ser
                245                 250                 255

Pro Leu Lys Gly Glu Met Arg Leu Gln Thr Asp His Leu Phe Ala Arg
            260                 265                 270

Asp Ser Arg Thr Ala Cys Glu Trp Gln Ser Phe Val Asn Asn Gln Thr
        275                 280                 285

Lys Leu Gln Glu Asp Phe Gln Phe Ile Phe Thr Ala Leu Ser Thr Leu
    290                 295                 300

Gly His Asp Met Asn Ala Met Ile Asp Cys Ser Glu Val Ile Pro Ala
305                 310                 315                 320

Pro Lys Pro Val Asn Phe Gly Pro Ser Phe Pro Ala Gly Lys Thr
                325                 330                 335

His Ala Asp Ile Glu Gln Ala Cys Ala Ser Thr Pro Phe Pro Thr Leu
            340                 345                 350

Ile Thr Ala Pro Gly Pro Ser Ala Ser Val Ala Arg Ile Pro Pro Pro
        355                 360                 365

Pro Ser Pro Asn
    370
```

<210> SEQ ID NO 21
<211> LENGTH: 1263
<212> TYPE: DNA
<213> ORGANISM: Phanerochaete chrysosporium

<400> SEQUENCE: 21

```
gctacagctc accgtccggt ctcagcagca gcaatggcgt tcaagcagct cctcgcagcc    60
ctctccgtcg ccctgaccct ccaggtcacc caagctgccc cgaacctcga caagcgcgtc   120
gcttgccccg acggcgtgca caccgcctcc aacgcggcgt gctgtgcatg gttcccggtc   180
ctcgatgata tccagcagaa cctcttccac ggtggccagt gcggtgccga ggcccacgag   240
gcccttcgta tggtcttcca cgactccatc gctatctcgc ccaagcttca gtcgcagggc   300
aagtttggcg gcggcggcgc ggacggctcg atcattacct tctcctcgat cgagaccacg   360
taccacccga acatcggcct cgacgaggtc gtcgccatcc agaagccgtt catcgcgaag   420
cacggcgtca cccgtggcga cttcatcgca ttcgctggtg ccgtcggcgt gagcaactgc   480
ccgggcgcgc gcagatgca gttcttcctt ggccgccccg aggcaacgca ggccgccccc   540
gacggtctcg tgcccgagcc cttccacacc atcgatcagg ttctcgctcg catgcttgac   600
gctggtggct cgacgagat cgagactgtc tggctgctct ctgcccactc catcgcggct   660
gcgaacgacg tcgacccgac catctccggc ctgccgttcg actccactcc cggccagttc   720
gactcccagt tcttcgtcga cacgcagctc cgcggtaccg cattccctgg caagactggt   780
atccagggca ccgtcatgtc cccgctcaag ggcgagatgc gtctgcagac ggaccacttg   840
ttcgcgcgtg actcgcgcac ggcatgcgag tggcagtcct tcgtcaacaa ccagacgaag   900
ctgcaggagg acttccagtt catcttcacg gcgctctcga cgctcggcca cgacatgaac   960
gccatgatcg actgctccga ggtcatcccc cgcgcccaag ccgtcaactt cggcccgtcg  1020
ttcttccccg ccggtaagac gcacgccgac atcgagcagg cctgcgcatc cacgccgttc  1080
ccgacgctca tcaccgcccc cggtccctct gcgtccgtcg ctcgcatccc ccgccgccg   1140
tcccccaact aagctatgtc tatgctggac atgctctcgg ttctacctcg tcggtatcgt  1200
cgcacggtta tctcgcgttt gcatcatgta tacctgctcg tggaatatac aaagtggtct  1260
atc                                                                1263
```

<210> SEQ ID NO 22
<211> LENGTH: 372
<212> TYPE: PRT
<213> ORGANISM: Phanerochaete chrysosporium

<400> SEQUENCE: 22

```
Met Ala Leu Lys Gln Leu Ala Ala Ala Val Ala Leu Ala Leu Ser Ile
1               5                   10                  15

Gln Ala Ala Gln Gly Ala Ala Val Lys Glu Lys Arg Ala Thr Cys Ser
            20                  25                  30

Asn Gly Ala Thr Val Gly Asp Ala Ser Ser Cys Ala Trp Phe Asp Val
        35                  40                  45

Leu Asp Asp Ile Gln Gln Asn Leu Phe Asn Gly Ala Gln Cys Gly Ala
    50                  55                  60

Glu Ala His Glu Ser Ile Arg Leu Val Phe His Asp Ala Ile Ala Ile
65                  70                  75                  80

Ser Pro Ala Leu Glu Ser Gln Gly Lys Phe Gly Gly Gly Gly Ala Asp
                85                  90                  95
```

```
Gly Ser Ile Ile Leu Phe Asp Asp Ile Glu Thr Asn Phe His Pro Asn
            100                 105                 110

Ile Gly Leu Asp Glu Ile Val Asn Leu Gln Lys Pro Phe Ile Gln Lys
        115                 120                 125

His Gly Val Thr Pro Gly Asp Phe Ile Ala Phe Ala Gly Ala Val Ala
    130                 135                 140

Met Ser Asn Cys Pro Gly Ala Pro Gln Met Asn Phe Phe Thr Gly Arg
145                 150                 155                 160

Ala Pro Ala Thr Gln Ala Ala Pro Asp Gly Leu Val Pro Glu Pro Phe
                165                 170                 175

His Thr Val Asp Gln Ile Ile Ser Arg Val Asn Asp Ala Gly Glu Phe
            180                 185                 190

Asp Glu Leu Glu Leu Val Trp Met Leu Ser Ala His Ser Val Ala Ala
        195                 200                 205

Ala Asn Asp Val Asp Pro Thr Ile Gln Gly Leu Ala Phe Asp Ser Thr
    210                 215                 220

Pro Gly Val Phe Asp Ser Gln Phe Phe Val Glu Thr Gln Leu Arg Gly
225                 230                 235                 240

Thr Ala Phe Pro Gly Ser Gly Asn Gln Gly Glu Val Glu Ser Pro
                245                 250                 255

Leu Pro Gly Glu Met Arg Leu Gln Ser Asp Ser Ser Ile Ala Arg Asp
            260                 265                 270

Ser Arg Thr Ala Cys Glu Trp Gln Ser Phe Val Asn Asn Gln Ser Lys
        275                 280                 285

Leu Val Ser Asp Phe Gln Phe Ile Phe Leu Ala Leu Thr Gln Leu Gly
    290                 295                 300

Glu Asn Pro Asp Ala Met Thr Asp Cys Ser Asp Val Ile Pro Ile Ser
305                 310                 315                 320

Lys Pro Val Pro Asn Asn Val Pro Phe Ser Phe Pro Ala Gly Lys
                325                 330                 335

Thr Met Ala Asp Val Glu Gln Ala Cys Ala Glu Thr Pro Phe Pro Thr
            340                 345                 350

Leu Thr Thr Leu Pro Gly Pro Glu Thr Ser Val Gln Arg Ile Gln Pro
        355                 360                 365

Pro Pro Gly Ala
    370

<210> SEQ ID NO 23
<211> LENGTH: 1119
<212> TYPE: DNA
<213> ORGANISM: Phanerochaete chrysosporium

<400> SEQUENCE: 23
atggctctta agcaactcgc tgctgccgtc gctctcgcac tctcgatcca ggctgcccaa      60
ggcgctgctg tgaaggagaa gcgcgccacc tgctccaacg gcgcgactgt cggcgacgcg     120
tcgtcgtgcg cctggtttga cgttctcgac gacatccagc agaaccctct caacggcgcc     180
cagtgtggtg ctgaggctca cgagtccatt cgtcttgtct ccacgacgc catcgctatc     240 tcgcctgccc ttgagtctca aggcaaattc ggtggtggag cgctgatgg ctccattatc     300 ctcttcgacg atatcgagac caactttcac cccaacattg gccttgacga gattgtcaac     360
ctgcagaagc ccttcatcca gaagcacggc gttactcctg gcgatttcat tgcctttgct     420
ggcgccgtcg ccatgagcaa ctgccctggt gctccgcaga tgaacttctt caccggtcgt     480
gctcctgcta ctcaggccgc tccagacggc ctcgttcccg agccattcca cactgtcgac     540
```

-continued

```
cagatcatct ctcgcgtcaa cgacgctggc gagtttgacg agcttgagct cgtctggatg      600
ctgtctgctc actccgtcgc tgcggcgaac gatgtcgatc cgacgatcca ggggcttgcg      660
ttcgactcta ccccgggtgt cttcgactcg cagttcttcg ttgagacaca gcttcgcggc      720
acggcgttcc ccggctcggg tggcaaccag ggtgaggttg aatcccctct ccccggtgag      780
atgcgcctcc agtccgactc ctcgatcgcc cgcgactcgc gcacggcgtg cgagtggcag      840
tccttcgtca acaaccagtc gaagctcgtt agcgacttcc agttcatctt cctcgccctt      900
acccagctcg gcgagaaccc ggatgctatg accgactgct cagacgtgat cccgatctcg      960
aagccggtcc ccaacaacgt cccgttctcg ttcttcccgg ctggcaagac catggctgat     1020
gttgagcagg cgtgtgctga cgcccttc ccgactctga cgacgcttcc tggccccgag     1080
acctcggtgc agcgcatcca gcctcctccg ggtgcttaa                             1119
```

<210> SEQ ID NO 24
<211> LENGTH: 372
<212> TYPE: PRT
<213> ORGANISM: Phanerochaete sordida

<400> SEQUENCE: 24

```
Met Ala Phe Lys Arg Leu Leu Ala Val Leu Thr Ala Ala Ile Ser Leu
1               5                  10                  15

Gly Ala Val Gln Gly Val Ala Val Glu Lys Arg Ala Thr Cys Ser Asn
            20                  25                  30

Gly Lys Thr Val Ser Ala Ser Cys Cys Ala Trp Phe Asn Val Leu
        35                  40                  45

Ser Asp Ile Gln Glu Asn Leu Phe Asn Gly Gly Gln Cys Gly Ala Glu
    50                  55                  60

Ala His Glu Ser Ile Arg Leu Val Phe His Asp Ser Ile Ala Ile Ser
65                  70                  75                  80

Pro Ala Met Glu Ala Ala Gly Gln Phe Gly Gly Gly Ala Asp Gly
                85                  90                  95

Ser Ile Met Ile Phe Asp Glu Ile Glu Thr Asn Phe His Pro Asn Ile
            100                 105                 110

Gly Leu Asp Glu Ile Val Arg Leu Gln Lys Pro Phe Val Gln Lys His
        115                 120                 125

Gly Val Thr Pro Gly Asp Phe Ile Ala Phe Ala Gly Ala Val Ala Leu
    130                 135                 140

Ser Asn Cys Pro Gly Ala Pro Gln Met Asn Phe Phe Thr Gly Arg Ala
145                 150                 155                 160

Pro Ala Thr Gln Ala Ala Pro Asp Gly Leu Val Pro Glu Pro Phe His
                165                 170                 175

Thr Val Asp Gln Ile Ile Asp Arg Val Gly Asp Ala Gly Glu Phe Asp
            180                 185                 190

Glu Leu Glu Leu Val Trp Met Leu Ser Ala His Ser Ile Ala Ala Ala
        195                 200                 205

Asn Asp Val Asp Pro Thr Thr Gln Gly Leu Pro Phe Asp Ser Thr Pro
    210                 215                 220

Gly Ile Phe Asp Ser Gln Phe Val Glu Thr Gln Leu Ala Gly Thr
225                 230                 235                 240

Gly Phe Pro Ala Ser Ala Asn Asn Gln Gly Glu Val Thr Ser Pro Leu
                245                 250                 255

Ala Gly Glu Met Arg Leu Gln Ser Asp Phe Leu Ile Ala Arg Asp Ala
            260                 265                 270
```

```
Arg Thr Ala Cys Glu Trp Gln Ser Phe Val Asn Asn Gln Ser Lys Leu
                275                 280                 285

Val Ser Asp Phe Gln Phe Ile Phe Leu Ala Leu Thr Gln Leu Gly Gln
            290                 295                 300

Asp Pro Thr Val Met Thr Asp Cys Ser Asp Val Ile Pro Ile Ser Lys
305                 310                 315                 320

Pro Ala Pro Ala Asn Thr Pro Gly Phe Ser Phe Phe Pro Ala Gly Lys
                325                 330                 335

Thr Met Ala Asp Val Glu Gln Ala Cys Ala Glu Thr Pro Phe Pro Thr
            340                 345                 350

Leu Ser Thr Leu Pro Gly Pro Gln Thr Ser Val Ala Arg Ile Gln Pro
                355                 360                 365

Pro Pro Gly Ala
        370

<210> SEQ ID NO 25
<211> LENGTH: 1727
<212> TYPE: DNA
<213> ORGANISM: Phanerochaete sordida

<400> SEQUENCE: 25
aggtcactct cagcctctca gactcttctc cagtcgccct agctcagaca tggctttcaa      60
gaggctcctc gctgttctca ccgccgccat ctccctcggc gccgtccagg gtacgtccta    120
cgcttcccca ctttaccgca ggacactgac agcggcgcct aggtgtcgct gttgagaagc    180
gcgccacctg ctccaacggc aagacggtca gcgcgtcgtc gtgctgcgcc tggttcaatg    240
tcctctcgga catccaggag aacctcttca acggcggcca gtgcggcgct gaggcccatg    300
agtccatccg cctgtaagca tcaccctctg tccctagcgt tcttgcactg atctcgtcgc    360
agtgtcttcc acgactccat cgccatctcg cctgctatgg aggccgctgg tcagtttggg    420
tatgtagacg tggcctccgc ttctgcacaa tcctgacaga gcacaatata gcggcggcgg    480
tgctgacggc tccatcatga tcttcgacga gatcgagacc aacttccacc caacatcgg    540
cctcgacgag atcgtgcgcc tgcagaagcc cttcgtccag aagcacggcg tcaccccgg    600
cgacttcatc gccttcgctg gcgcggttgc cctgtccaac tgccccggtg ccccgcagat    660
gaacttcttc accggccgtg ctcccgccac ccaggccgcc cccgatggtc ttgtccccga    720
gcccttccgt gagttattcc gcccacatat gtcgaccgta gcgaactgac agcactcgta    780
gacactgtcg accagattat cgaccgtgtc ggcgacgccg gcgagttcga tgagctcgag    840
ctcgtctgga tgctttccgc gtacggcttc gttctcactg ccggctatcg catactgatc    900
aatcgactcc agccattcca ttgcggctgc gaacgacgtc gacccgacca cccagggtct    960
tcccttcgac tccaccccgg gtatcttcga ctcgcagttc ttcgtcgaga cccagctcgc   1020
cggcactggc ttcccgcgt acgtctcctc gtctttccct ccttctgcgc tgctcaccac   1080
gcctacagct ccgcgaacaa ccagggcgag gtcacgtccc cgcttgcggg cgagatgcgc   1140
ctgcagtccg acttcctcat cgcccgcgac gcgcgcaccg catgcgagtg cagtccttc   1200
gtcaacaacc agtcgaagct cgtgtccgac ttccagttca tcttcctcgc cctcacgcag   1260
ctcggccagg acccgaccgt catgaccgac tgctcggacg ttattcccat ctccaagccc   1320
gcgcccgcga acacccccgg attctctttt ccccgccg gcaagaccat ggctgacgtc   1380
gagcaggctg tgcgtgaatt catgtttgag cgcatatatg tggctggcaa gctgacgaac   1440
gctcctctag tgcgccgaga cgcccttccc gactctctcg accctccccg gcccgcaaac   1500
```

-continued

```
ctcggtcgct cgcatgttcg tactaaaatt caatcatatc cggggggccag ctgacaatgt  1560 tttcttacag ccaaccccct cccggtgctt aaatagccac cacaacccgg ttctctcccc  1620
ggcacaggca gctaagctta gacttaaccc cagaaggttc agatgtagaa actgctcgct  1680
ttgtctcaat accgcttttg aagcaaatac acgtgtatta ctggccc                1727
```

<210> SEQ ID NO 26
<211> LENGTH: 371
<212> TYPE: PRT
<213> ORGANISM: Phanerochaete chrysosporium (anamorph: Sporotrichum pruinosum)

<400> SEQUENCE: 26

| Met | Ala | Leu | Lys | Gln | Leu | Ala | Ala | Val | Ala | Leu | Ala | Leu | Ser | Ile |
|---|---|---|---|---|---|---|---|---|---|---|---|---|---|---|
| 1 | | | | 5 | | | | | 10 | | | | | 15 |

| Gln | Ala | Ala | Gln | Gly | Ala | Ala | Val | Lys | Glu | Lys | Arg | Ala | Thr | Cys | Ser |
|---|---|---|---|---|---|---|---|---|---|---|---|---|---|---|---|
| | | | 20 | | | | 25 | | | | | 30 | | | |

Asn Gly Ala Thr Val Gly Asp Ala Ser Ser Cys Ala Trp Phe Asp Val
          35                  40                  45

Leu Asp Asp Ile Gln Gln Asn Leu Phe Asn Gly Ala Gln Cys Gly Ala
 50                  55                  60

Glu Ala His Glu Ser Ile Arg Leu Val Phe His Asp Ala Ile Ala Ile
 65                  70                  75                  80

Ser Pro Ala Leu Glu Ser Gln Gly Lys Phe Gly Gly Gly Gly Ala Asp
                 85                  90                  95

Gly Ser Ile Ile Leu Phe Asp Asp Ile Glu Thr Asn Phe His Pro Asn
                100                 105                 110

Ile Gly Leu Asp Glu Ile Val Asn Leu Gln Lys Pro Phe Ile Gln Lys
                115                 120                 125

His Gly Val Thr Pro Gly Asp Phe Ile Ala Phe Ala Gly Ala Val Ala
            130                 135                 140

Met Ser Asn Cys Pro Gly Ala Pro Gln Met Asn Phe Phe Thr Gly Arg
145                 150                 155                 160

Ala Pro Ala Thr Gln Ala Ala Pro Asp Gly Leu Val Pro Glu Pro Phe
                165                 170                 175

His Thr Val Asp Gln Ile Ile Ser Arg Val Asn Asp Ala Gly Glu Phe
            180                 185                 190

Asp Glu Leu Glu Leu Val Trp Met Leu Ser Ala His Ser Val Ala Ala
        195                 200                 205

Ala Asn Asp Val Asp Pro Thr Ile Gln Gly Leu Ala Phe Asp Ser Thr
    210                 215                 220

Pro Gly Val Phe Asp Ser Gln Phe Phe Val Glu Thr Gln Leu Arg Gly
225                 230                 235                 240

Thr Ala Phe Pro Gly Ser Gly Asn Gln Gly Glu Val Glu Ser Pro
                245                 250                 255

Leu Pro Gly Glu Met Arg Leu Gln Ser Asp Ser Ser Ile Ala Arg Asp
            260                 265                 270

Ser Arg Thr Ala Cys Glu Trp Gln Ser Phe Val Asn Asn Gln Ser Lys
        275                 280                 285

Leu Val Ser Asp Phe Gln Phe Ile Phe Leu Ala Leu Thr Gln Leu Gly
    290                 295                 300

Glu Asn Pro Asp Ala Met Thr Asp Cys Ser Asp Val Ile Pro Ile Ser
305                 310                 315                 320

Lys Pro Val Pro Asn Asn Val Pro Phe Ser Phe Phe Pro Ala Gly Lys

```
                    325                 330                 335
Thr Met Ala Asp Val Glu Gln Ala Cys Ala Glu Thr Pro Phe Pro Thr
            340                 345                 350
Leu Thr Thr Leu Pro Gly Pro Glu Thr Ser Val Gln Arg Ile Pro Pro
        355                 360                 365
Pro Gly Ala
    370
```

<210> SEQ ID NO 27
<211> LENGTH: 2104
<212> TYPE: DNA
<213> ORGANISM: Phanerochaete chrysosporium (anamorph: Sporotrichum pruinosum)

<400> SEQUENCE: 27

```
tatgttttct tttaccatag tgtcttcgcc attcagtgca gagcgcaaca tgactgtcat    60
gccgccgttg ctcgacccac gactacaatg ccgtctgtcg agcatctact cccgaccgat   120
cctcgttcac aggcaaggta cgcgcttttt tcattggctg cggtggccag ggagtctgct   180
atcgagggca cacggcgcgg cgagggcatc ggcagaggcg agggtagtg caggccagag    240
cggtataaaa acgcaaacag gcaggccacc ctctctccag acactcgca gtcttctgtg    300
cgctcagctt aacagtcatg gctcttaagc aactcgctgc tgccgtcgct ctcgcactct   360
cgatccaggc tgcccaaggt gcggcatcta ctccatatcc ttgtccccc gtactgacct    420
cgatgcaggc gctgctgtga aggagaagcg cgccacctgc tccaacggcg cgactgtcgg   480
cgacgcgtcg tcgtgcgcct ggtttgacgt tctcgacgac atccagcaga acctcttcaa   540
cggcgcccag tgtggtgctg aggctcacga gtccattcgt ctgtaagtgc ctccgcttgt   600
ttcggtctag agcctactca ccgcgtctac agtgtcttcc acgacgccat cgctatctcg   660
cctgcccttg agtctcaagg caaattcggg tcgcgtcctc tctccgtttg actgcagggg   720
gtcgctgagt gtagcatagt ggtggaggcg ctgatggctc cattatcctc ttcgacgata   780
tcgagaccaa ctttcacccc aacattggcc ttgacgagat tgtcaacctg cagaagccct   840
tcatccagaa gcacggcgtt actcctggcg atttcattgc ctttgctggc gccgtcgcca   900
tgagcaactg ccctggtgct ccgcagatga acttcttcac cggtcgtgct cctggtatgt   960
gttgagcacc ccagcgtgga atcagtctga cacttgtcct gcagctactc aggccgctcc  1020
agacggcctc gttcccgagc cattccgtac gtcagctgca cagatacgca tatacacccg  1080
ctgaccaact cttacagaca ctgtcgacca gatcatctct cgcgtcaacg acgctggcga  1140
gtttgacgag cttgagctcg tctggatgct gtctgcgtaa gttgcaatcc ggctgttcta  1200
cactgacaga gctgaccaca cgccacagtc actccgtcgc tgcggcgaac gatgtcgatc  1260
cgacgatcca ggggcttgcg ttcgactcta ccccgggtgt cttcgactcg cagttcttcg  1320
ttgagacaca gcttcgcggc acggcgttcc ccggctcggg tggcaaccag ggtgaggttg  1380
aatcccctct ccccggtgag atgcgcctcc agtccgactc ctcgatcgcc cgcgactcgc  1440
gcacggcgtg cgagtggcag tccttcgtca gtgcgtatta catgtgcatc ctagggcgag  1500
tggtcagacg ctgagtttgc gccgtagaca accagtcgaa gctcgttagc gacttccagt  1560
tcatcttcct cgcccttacc cagctcggcg agaacccgga tgctatgacc gactgctcag  1620
acgtgatccc gatctcgaag ccggtcccca acaacgtccc gttctcgttc ttccgggctg  1680
gcaagaccat ggctgatgtt gagcaggcgg tgcgtagcaa ctcacgtcta ccatattgct  1740
gcaggagcta acttatgcac agtgtgctga cacgcccttc ccgactctga cgacgcttcc  1800
```

```
tggccccgag acctcggtgc agcgcatgta agtactttct gatgccaatg tacaagcacc    1860
aaggcactaa cggtccattg cagccaghcc tcctccgggt gcttaaattg tattcatcac    1920
ggtcatcacg ttcacggtac tactacgtct ggattgcgtc gccttggctg cctttgtagg    1980
cttatcgaat acacagcttt tctctcagtc atgaccatga agtgtgccat ggtaagcgga    2040
gacaagcaat tcttcgattg tggctcgcat gccgcccgta gcacatagct cctatgtagt    2100
gcac                                                                 2104
```

ENZYMATIC SYSTEM-CONTAINING COSMETIC COMPOSITIONS

RELATED APPLICATIONS

This application is a National Phase of PCT Patent Application No. PCT/IL2014/050477 having International filing date of May 27, 2014, which claims the benefit of priority under 35 USC § 119(e) of U.S. Provisional Patent Application No. 61/827,685 filed on May 27, 2013. The contents of the above applications are all incorporated by reference as if fully set forth herein in their entirety.

SEQUENCE LISTING STATEMENT

The ASCII file, entitled 64282SequenceListing.txt, created on Oct. 20, 2015 comprising 78,904 bytes, submitted concurrently with the filing of this application is incorporated herein by reference.

FIELD AND BACKGROUND OF THE INVENTION

The present invention, in some embodiments thereof, relates to novel cosmetic compositions, kits and methods and, more particularly, but not exclusively, to cosmetic compositions, kits and methods, which utilize an enzymatic system for producing hydrogen peroxide in situ, and to uses thereof in, for example, lightening skin and/or hair.

The color of human skin is governed by the quantity, quality, and distribution of melanin, a pigment which is also present in plants and microorganisms.

The synthesis of melanin initiates from the precursor L-tyrosine, which is transformed into a second precursor dopaquinone via the action of tyrosinase. Synthesis of melanin takes place in melanosomes, which are present in melanocyte cells present in the epidermal basal layer; synthesis of melanin in these cells is induced by ultraviolet (UV) light. Following synthesis, melanin migrates to epidermal cells and is dispersed therein, where melanin is decolored following dermal metabolism and then scaled off in the form of dirt at the time of skin renewal. Melanin has a clinical importance since it protects the skin from adverse effects caused by UV light. However, high levels of melanin can result in unwanted skin darkening, while the heterogeneous distribution thereof can lead to chloasma and freckling which can be aesthetically displeasing.

Skin lightening products have become increasingly popular in the past few years. The main purpose of skin lightening products is to lighten or whiten the skin or to treat pigmentation disorders such as chloasma, freckles, pregnancy marks and age spots. Several types of skin lightening products are presently available.

Products based on the degeneration and death of pigment cells typically include harsh chemicals, such as hydroquinone, 4-isopropylcatechol, and hydroquinone monobenzyl ether, that promote skin whitening, lightening or fade out skin pigmentation. Other agents which are commonly-available for skin-whitening include kojic acid and derivatives thereof, which inhibits melanin production, and a variety of extracts such as licorice (*Glycyrrhiza glabra*) which include glabridin that decreases oxidization activity of the melanin creating cells in the skin in similar way as Kojic acid does.

Other lightening products are based on the inhibition of tyrosinase, the enzyme that transforms the precursor L-tyrosine into a second precursor dopaquinone. This group of products includes arbutin, a glucose hydroquinone compound, which is capable of inhibiting tyrosinase by chelating copper ions thereby suppressing the tautomerization from dopachrome to 5,6-dihydroxyindole (DHI) and 5,6-dihydroxyindole-2-carboxylic acid (DHICA). Melanostat is another lightening product that acts through tyrosinase. Melanostat is a synthetic peptide that functions in deactivating melanogenesis in melanocytes.

Several antioxidant compounds that can inhibit the production of melanin are also utilized in lightening products. Since the synthesis of melanin involves an oxidation reaction, blocking the oxidation at various points from tyrosine/DOPA to melanin ultimately inhibits the synthesis of melanin. For example, L-ascorbic acid (vitamin C) acts as a reducing agent on melanin intermediates and blocks oxidative reactions; other antioxidants utilized by lightening products include bioflavonoids, which are typically extracted from mulberry or licorice.

However, the currently available skin whitening products are typically inefficient and may be harmful to the skin since a continuous external application of these products can lead to permanent leucoderma and side effects such as dyschromatosis and rash.

Consumers frequently use cosmetic products to care for their skin. Rough and/or broken skin and hyperpigmentations (such as age spots, freckles, and brown patches associated with sunlight exposure, skin aging or environmental damage to the human skin) are areas consumers typically seek to treat. Skin whitening is of particular interest in certain Asian populations.

U.S. Patent Application Publication No. 20050013784 discloses a treatment mask comprising a water insoluble substrate and a liquid composition comprising a skin tone changing agent and a water-soluble thickening agent.

Treatment masks, which include hydrogen peroxide, are currently available from Reviva Labs (e.g., Oxygen Mask, Green Papaya & Hydrogen Peroxide Oxygen Mask, REV-11305).

International Patent Application Publication WO 2004/052275 discloses methods of producing lignin peroxidase, and methods and cosmetic compositions suitable for skin and hair lightening as well as kits and an article-of-manufacturing including active ingredients for skin and hair lightening.

International Patent Application Publication WO 2012/153336 discloses kits and methods for lightening a skin of a subject, using a mask comprising an oxidizing activator such as hydrogen peroxide, and a cosmetic composition comprising a lignin peroxidase; or a mask comprising a lignin peroxidase and a cosmetic composition comprising the oxidizing activator.

U.S. Pat. No. 8,426,158 describes methods for increasing hydrolysis of a cellulosic material by hydrolyzing the cellulosic material with an enzyme composition in the presence of a polypeptide having peroxidase activity, the peroxidase activity being for reducing the inhibition of hydrolysis by peroxides generated during fermentation.

Hydrogen peroxide is formed in saliva by oxidation of glucose by glucose oxidase. The hydrogen peroxide serves as a substrate for lactoperoxidase in the saliva, which forms bactericidal oxidized intermediates such as hypothiocyanate, hypobromite and hypoiodite from thiocyanate, bromide and iodide, respectively.

International Patent Application Publication WO 88/002600 describes a bactericidal composition comprising a hydrogen peroxide-forming enzyme such as glucose oxidase, a peroxidase such as lactoperoxidase, a thiocyanate and lysozyme. Hydrogen peroxide generated during use is intended, in combination with the peroxidase, to convert the thiocyanate into hypothiocyanate, thereby attenuating bacteria such that they are lysed by the lysozyme.

Midda & Cooksey [*J Clin Periodontol* 1986, 13:950-956] describe mouthrinses and dentrifices which contain amyloglucosidase and glucose oxidase for producing hydrogen peroxide from dietary fermentable carbohydrates, which in turn converts thiocyanate to hypothiocyanate in the presence of salivary lactoperoxidase, thereby inhibiting bacteria.

Enzycal™ toothpaste (Curaprox) contains lactoperoxidase, glucose oxidase and amyloglucosidase, for strengthening the antibacterial effect of saliva [*Br Dent J* 2008, 205:681].

Biotene™ toothpaste and mouthwash (GlaxoSmithKline) contain glucose oxidase, lactoferrin, lactoperoxidase, lysozyme.

U.S. Pat. No. 5,607,681 describes anti-microbial compositions containing iodide, thiocyanate, glucose oxidase, D-glucose and optionally also a peroxidase such as lactoperoxidase. The compositions are for use as preservatives or as active agents in oral hygiene, deodorant and anti-dandruff products. The compositions may be provided as non-reacting dry powders and non-aqueous solutions which may be diluted in order to obtain anti-microbial activity.

U.S. Pat. No. 6,214,339 describes treatment of otitis externa in dogs and cats by administering to the outer ear of a non-aqueous composition containing an oxidizable substrate such as glucose and an oxidoreductase enzyme such as glucose oxidase, for producing hydrogen peroxide upon encountering the environment of the outer ear. The composition further contains an iodide salt and a peroxidase such as lactoperoxidase for producing hypoiodite from the hydrogen peroxide.

U.S. Pat. No. 7,833,290 describes a method of dyeing keratinous fibers by treatment with a compound such as hematoxylin, hematein, brazilin and brazilein; a metal salt; a bicarbonate; and hydrogen peroxide or a system which generates hydrogen peroxide, such as urea peroxide, metal peroxides, perborates, percarbonates and oxidases in the presence of a suitable substrate.

Additional background art includes Hugoson et al. [*Odontol Rev* 1974, 25:69-80]; U.S. Pat. No. 7,981,166; and U.S. Patent Application Publication Nos. 20040161435 and 20090130040.

SUMMARY OF THE INVENTION

The present inventors have now devised and successfully practiced a methodology which circumvents the need to include hydrogen peroxide in cosmetic compositions and kits, and in lignin peroxidase-containing compositions and kits in particular.

According to an aspect of some embodiments of the invention, there is provided a cosmetic composition for lightening a skin and/or hair of a subject, the composition comprising a lignin peroxidase, a hydrogen peroxide-producing enzyme, and a substrate of the hydrogen peroxide-producing enzyme.

According to an aspect of some embodiments of the invention, there is provided a kit for lightening a skin and/or hair of a subject, the kit comprising a hydrogen peroxide-producing enzyme, a substrate of the hydrogen peroxide-producing enzyme and a lignin peroxidase, wherein at least one of the hydrogen peroxide-producing enzyme, the substrate of the hydrogen peroxide-producing enzyme and the lignin peroxidase forms a part of a composition which is packaged individually within the kit.

According to an aspect of some embodiments of the invention, there is provided a cosmetic method of lightening a skin and/or hair of a subject, the method comprising contacting a skin and/or hair region of the subject with a composition comprising a lignin peroxidase, a hydrogen peroxide-producing enzyme and a substrate of the hydrogen peroxide-producing enzyme, thereby lightening the skin and/or hair of the subject.

According to an aspect of some embodiments of the invention, there is provided a cosmetic or pharmaceutical composition for application to skin, hair and/or a nail of a subject, the composition comprising a hydrogen peroxide-producing enzyme, and a substrate of the hydrogen peroxide-producing enzyme.

According to an aspect of some embodiments of the invention, there is provided a kit for applying a cosmetic or pharmaceutical composition to skin, hair and/or a nail of a subject, the cosmetic or pharmaceutical composition comprising hydrogen peroxide, the kit comprising a first composition comprising a hydrogen peroxide-producing enzyme, and a second composition comprising a substrate of the hydrogen peroxide-producing enzyme.

According to an aspect of some embodiments of the invention, there is provided a method of administering hydrogen peroxide to skin, hair and/or a nail of a subject, the method comprising contacting a skin, hair and/or a nail region of the subject with a composition comprising a hydrogen peroxide-producing enzyme and a substrate of the hydrogen peroxide-producing enzyme, thereby generating hydrogen peroxide on the skin, hair and/or nail.

According to some of any of the embodiments of the invention, and any combination thereof, a concentration of lignin peroxidase in the composition is in a range of from 1.25 to 125 units/gram.

According to some of any of the embodiments of the invention, and any combination thereof, a concentration of the hydrogen peroxide-producing enzyme in the composition is in a range of from 0.125 to 1250 units/gram.

According to some of any of the embodiments of the invention, and any combination thereof, a concentration of the substrate of the hydrogen peroxide-producing enzyme in the composition is in a range of from 0.0175 μmole/gram to 175 μmole/gram.

According to some of any of the embodiments of the invention, and any combination thereof, the composition further comprises an oxidizing mediator.

According to some of any of the embodiments of the invention, and any combination thereof, the oxidizing mediator is selected from the group consisting of veratryl alcohol, veratrole and 1,4-dimethoxybenzene.

According to some of any of the embodiments of the invention, and any combination thereof, a concentration of the oxidizing mediator in the composition is in a range of from 0.03 μmole/gram to 300 μmole/gram.

According to some of any of the embodiments of the invention, and any combination thereof, the hydrogen peroxide-producing enzyme is selected from the group consisting of a glucose oxidase, a hexose oxidase, a cholesterol oxidase, an aryl alcohol oxidase, an L-gulonolactone oxidase, a galactose oxidase, a pyranose-2-oxidase, a pyridoxine-4-oxidase, an alcohol oxidase, a 2-hydroxy-acid oxidase, a choline oxidase, a long-chain-alcohol oxidase, a glycerol-3-phosphate oxidase, a D-arabinono-1,4-lactone oxidase, a vanillyl alcohol oxidase, an alditol oxidase, a prosolanapyrone II oxidase, a paromamine 6'-oxidase, a glyoxal oxidase, a veratryl alcohol oxidase, an alcohol dehydrogenase, a cellobiose dehydrogenase, an aldehyde oxidase, an oxalate oxidase, an aryl aldehyde oxidase, a dihydroorotate oxidase, a pyrroloquinoline-quinone synthase, an L-amino acid oxidase, an L-glutamate oxidase, a polyamine oxidase, an NAD(P)H oxidase, a urate oxidase, a hydroxylamine oxidase, a thiol oxidase, a glutathione oxidase, a cytochrome c oxidase, a xanthine oxidase and a superoxide dismutase.

According to some of any of the embodiments of the invention, and any combination thereof, the hydrogen peroxide-producing enzyme comprises glucose oxidase and the substrate comprises D-glucose.

According to some of any of the embodiments of the invention, and any combination thereof, the lignin peroxidase is isoenzyme H1 or a modified form of isoenzyme H2.

According to some of any of the embodiments of the invention, and any combination thereof, the lignin peroxidase is a lignin peroxidase of a white rot fungus.

According to some of any of the embodiments of the invention, and any combination thereof, the lignin peroxidase is an extract of a *Phanerochaete chrysosporium* fungus.

According to some of any of the embodiments of the invention, and any combination thereof, the lignin peroxidase is recombinantly expressed.

According to some of any of the embodiments of the invention, and any combination thereof, the lignin peroxidase comprises a polypeptide sequence set forth in SEQ ID NO:1.

According to some of any of the embodiments of the invention, and any combination thereof, the cosmetic composition is in a form selected from the group consisting of a mask, a serum, a lotion, a cream, a shampoo, a gel and a toner.

According to some of any of the embodiments of the invention, and any combination thereof, the composition further comprises a cosmetically acceptable carrier and/or pharmaceutically acceptable carrier.

According to some of any of the embodiments of the invention, and any combination thereof, the composition further comprises a cosmetically acceptable carrier.

According to some of any of the embodiments of the invention, and any combination thereof, the composition is packaged in an air-tight container.

According to some of any of the embodiments of the invention, and any combination thereof, the air-tight container is configured for dispensing the composition without entry of air into the container.

According to some of any of the embodiments of the invention, and any combination thereof, the hydrogen peroxide-producing enzyme forms a part of a first composition of the kit and the substrate forms a part of a second composition of the kit, the first and second compositions being packaged individually within the kit.

According to some of any of the embodiments of the invention, and any combination thereof, the first composition further comprises lignin peroxidase.

According to some of any of the embodiments of the invention, and any combination thereof, the second composition further comprises lignin peroxidase.

According to some of any of the embodiments of the invention, and any combination thereof, the lignin peroxidase forms a part of a third composition within the kit, the third composition being packaged individually within the kit.

According to some of any of the embodiments of the invention, and any combination thereof, the hydrogen peroxide-producing enzyme and the substrate of the hydrogen peroxide-producing enzyme are packaged together in an air-tight package within the kit.

According to some of any of the embodiments of the invention, and any combination thereof, the air-tight package is a container configured for dispensing the composition without entry of air into the container.

According to some of any of the embodiments of the invention, and any combination thereof, a concentration of lignin peroxidase in a composition comprising the lignin peroxidase is in a range of from 2.5 to 250 units/gram.

According to some of any of the embodiments of the invention, and any combination thereof, the kit comprises an oxidizing mediator, the hydrogen peroxide-producing enzyme, the substrate of said hydrogen peroxide-producing enzyme and the lignin peroxidase.

According to some of any of the embodiments of the invention, and any combination thereof, the oxidizing mediator forms a part of a composition that comprises the lignin peroxidase.

According to some of any of the embodiments of the invention, and any combination thereof, a concentration of the oxidizing mediator in the composition is in a range of from 0.06 µmole/gram to 600 µmole/gram.

According to some of any of the embodiments of the invention, and any combination thereof, a concentration of the hydrogen peroxide-producing enzyme in a composition comprising the enzyme is in a range of from 0.25 to 2500 units/gram.

According to some of any of the embodiments of the invention, and any combination thereof, a concentration of the substrate in a composition comprising the substrate is in a range of from 0.035 µmole/gram to 350 µmole/gram.

According to some of any of the embodiments of the invention, and any combination thereof, the kit comprises:

a first composition comprising lignin peroxidase at a concentration in a range of from 2.5 to 250 units/gram, and glucose oxidase at a concentration in a range of from 2.5 to 250 units/gram; and a second composition comprising D-glucose at a concentration in a range of from 0.35 µmole/gram to 35 µmole/gram.

According to some of any of the embodiments of the invention, and any combination thereof, the composition which is packaged individually within the kit is in a form selected from the group consisting of a mask, a serum, a lotion, a cream, a shampoo, a gel and a toner.

According to some of any of the embodiments of the invention, and any combination thereof, the composition which is packaged individually within the kit further comprises a cosmetically acceptable carrier.

According to some of any of the embodiments of the invention, and any combination thereof, the composition is formed by a lignin peroxidase, a hydrogen peroxide-producing enzyme and a substrate of the hydrogen peroxide-producing enzyme as packaged within a kit described hereinabove.

According to some of any of the embodiments of the invention, and any combination thereof, the contacting is effected at least five times.

According to some of any of the embodiments of the invention, and any combination thereof, the contacting is effected once or twice per day.

According to some of any of the embodiments of the invention, and any combination thereof, the composition is formed by contacting the skin and/or hair region with the hydrogen peroxide-producing enzyme and/or the substrate of the hydrogen peroxide-producing enzyme subsequent to contacting the skin and/or hair region with the lignin peroxidase.

According to some of any of the embodiments of the invention, and any combination thereof, the skin comprises facial skin.

According to some of any of the embodiments of the invention, and any combination thereof, the skin comprises a skin region exposed to the sun.

According to some of any of the embodiments of the invention, and any combination thereof, lightening the skin comprises lightening whole skin complexion.

According to some of any of the embodiments of the invention, and any combination thereof, the skin comprises an uneven skin tone, dark spot(s), freckle(s), melasma, hyperpigmentation, skin discoloration, age spot(s), acne mark(s) and/or a scar.

According to some of any of the embodiments of the invention, and any combination thereof, the composition further comprises at least one agent which exhibits a cosmetic or pharmaceutical activity in a presence of hydrogen peroxide.

According to some of any of the embodiments of the invention, and any combination thereof, the at least one agent is selected from the group consisting of a peroxidase and an oxidative dye precursor.

According to some of any of the embodiments of the invention, and any combination thereof, the composition is selected from the group consisting of a bleaching composition, a hair-dye composition, an anti-microbial composition and an odor-removal composition.

According to some of any of the embodiments of the invention, and any combination thereof, the kit further comprises at least one agent which exhibits a cosmetic or pharmaceutical activity in a presence of hydrogen peroxide.

According to some of any of the embodiments of the invention, and any combination thereof, the first composition comprises glucose oxidase at a concentration in a range of from 2.5 to 250 units/gram, and the second composition comprises D-glucose at a concentration in a range of from 0.35 µmole/gram to 35 µmole/gram.

According to some of any of the embodiments of the invention, and any combination thereof, the first composition and second composition are each independently in a form selected from the group consisting of a mask, a serum, a lotion, a cream, a shampoo, a gel and a toner.

According to some of any of the embodiments of the invention, and any combination thereof, the first composition and second composition further comprise a cosmetically acceptable carrier and/or pharmaceutically acceptable carrier.

According to some of any of the embodiments of the invention, and any combination thereof, the composition is formed by a hydrogen peroxide-producing enzyme and a substrate of the hydrogen peroxide-producing enzyme as packaged within a kit described hereinabove.

According to some of any of the embodiments of the invention, and any combination thereof, the composition of a method as described hereinabove is any of the compositions described herein, including any one of the embodiments thereof, in any combination.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
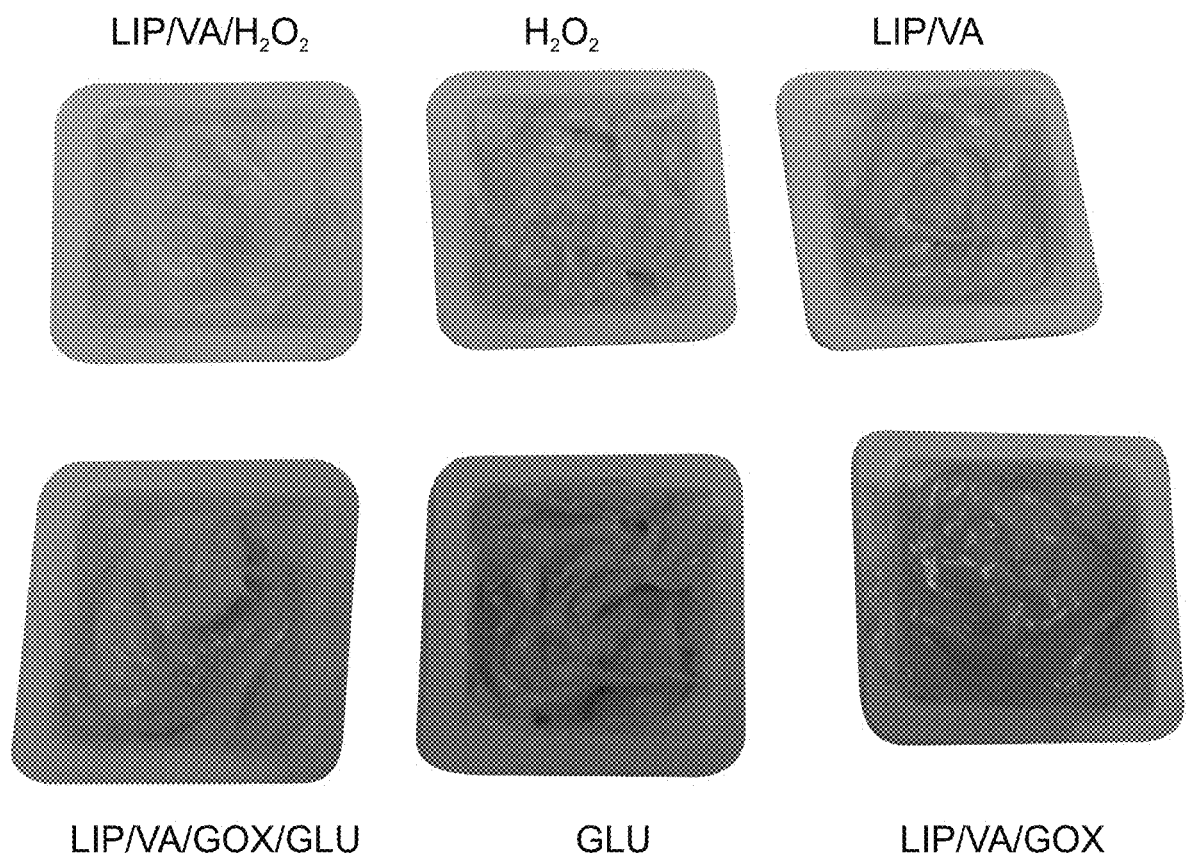
Figure 2A:
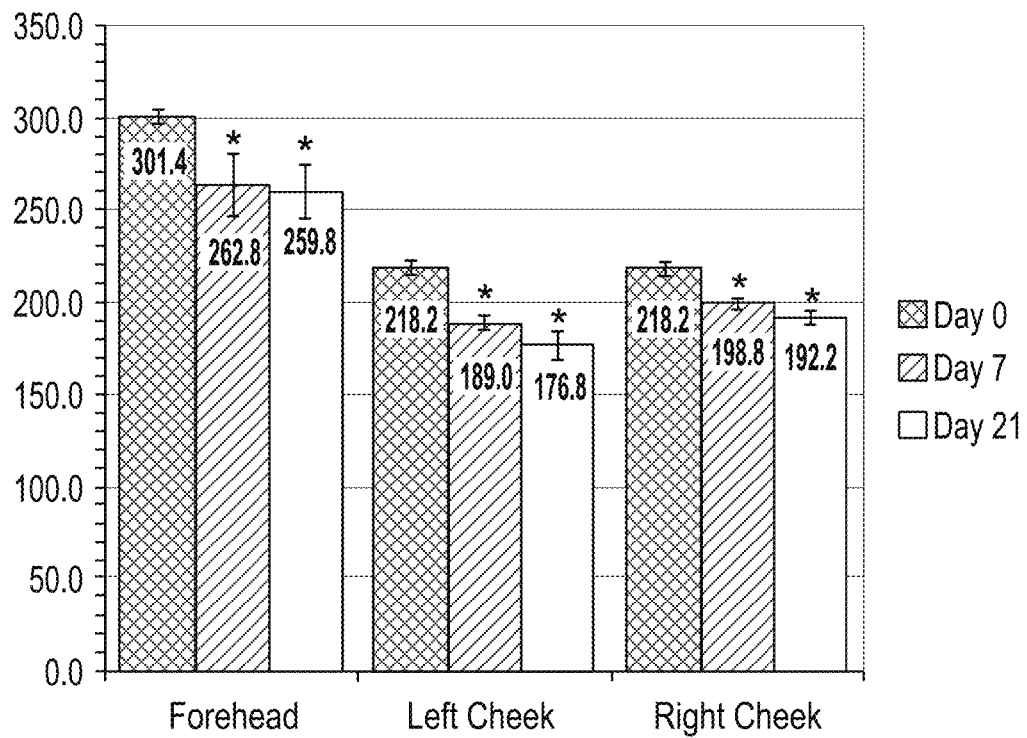
Figure 2B:
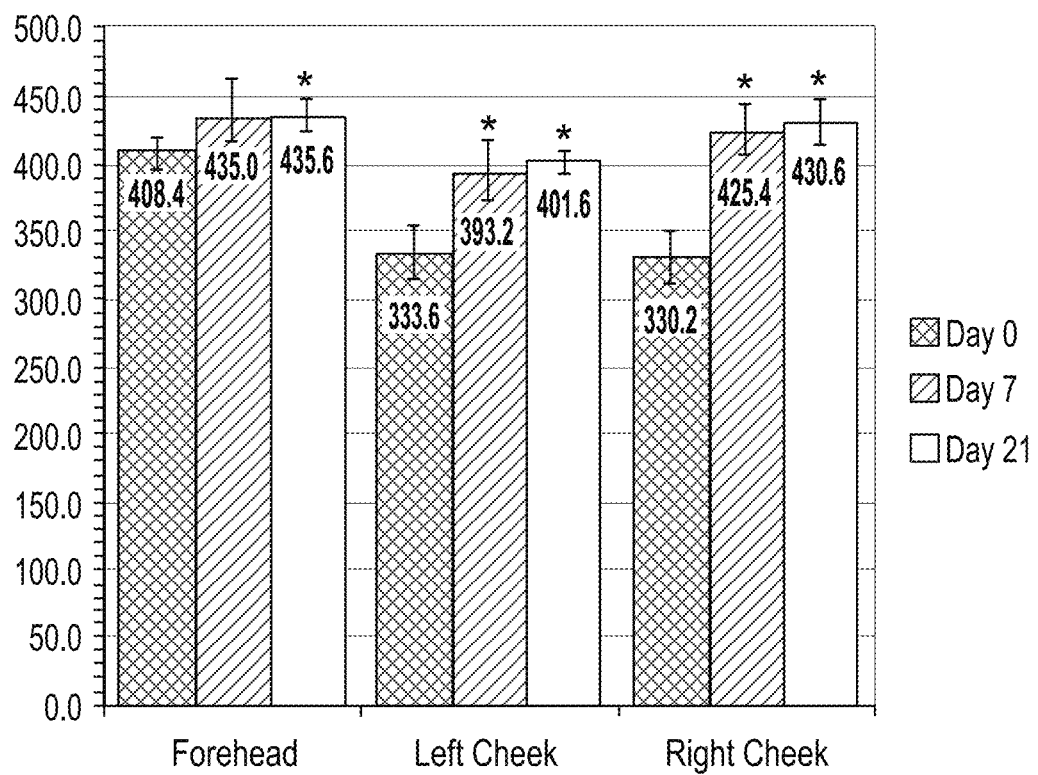
Figure 3A:
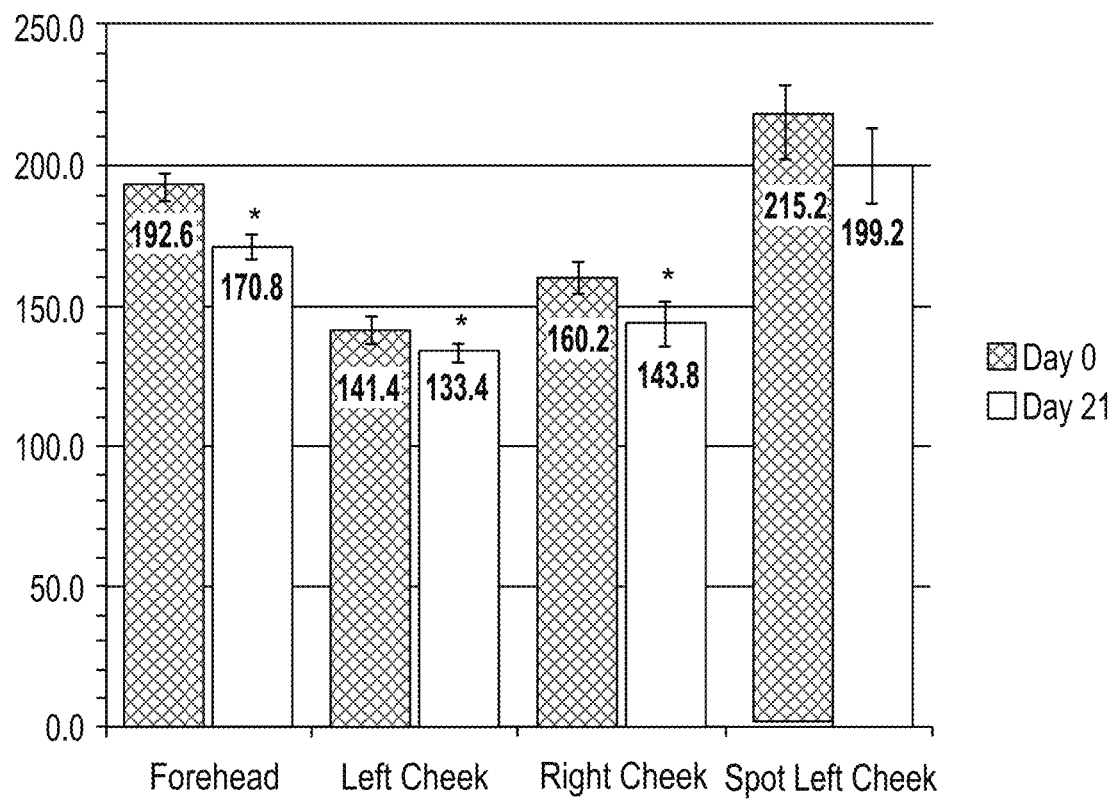
Figure 3B:
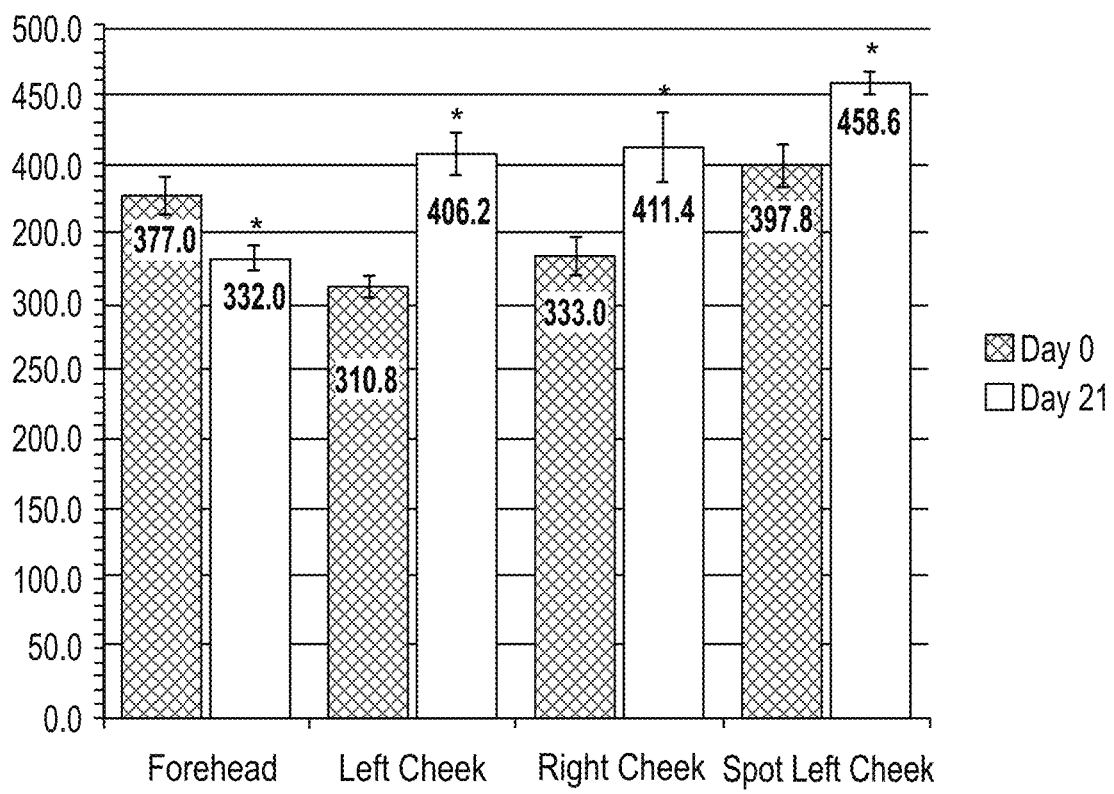
Figure 4A:
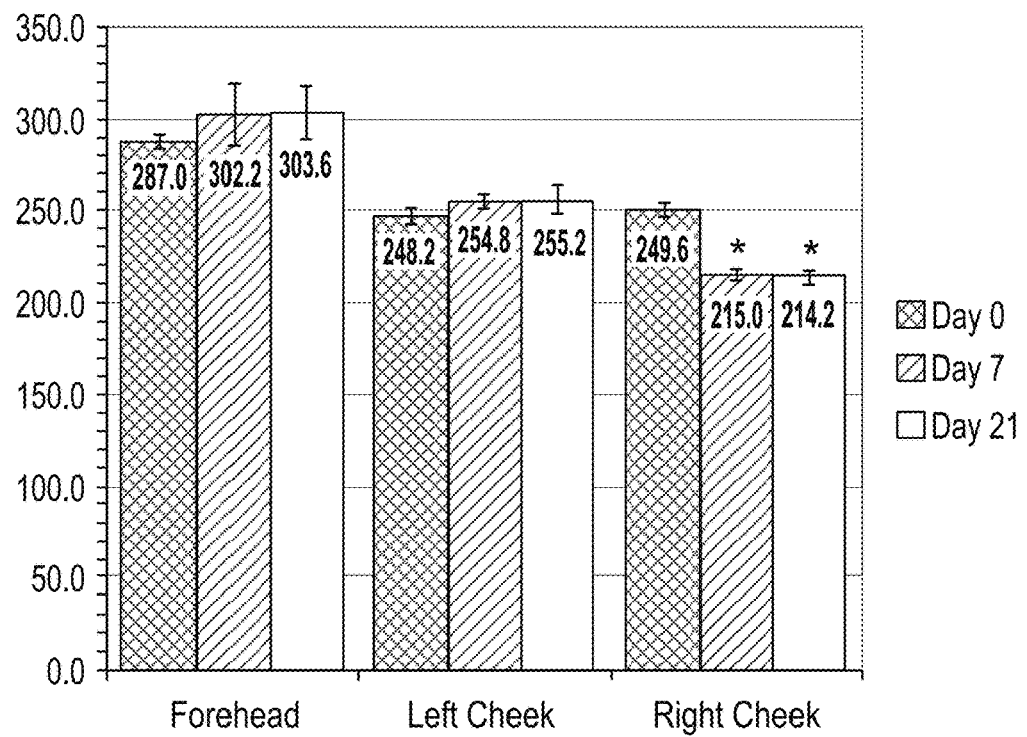
Figure 4B:
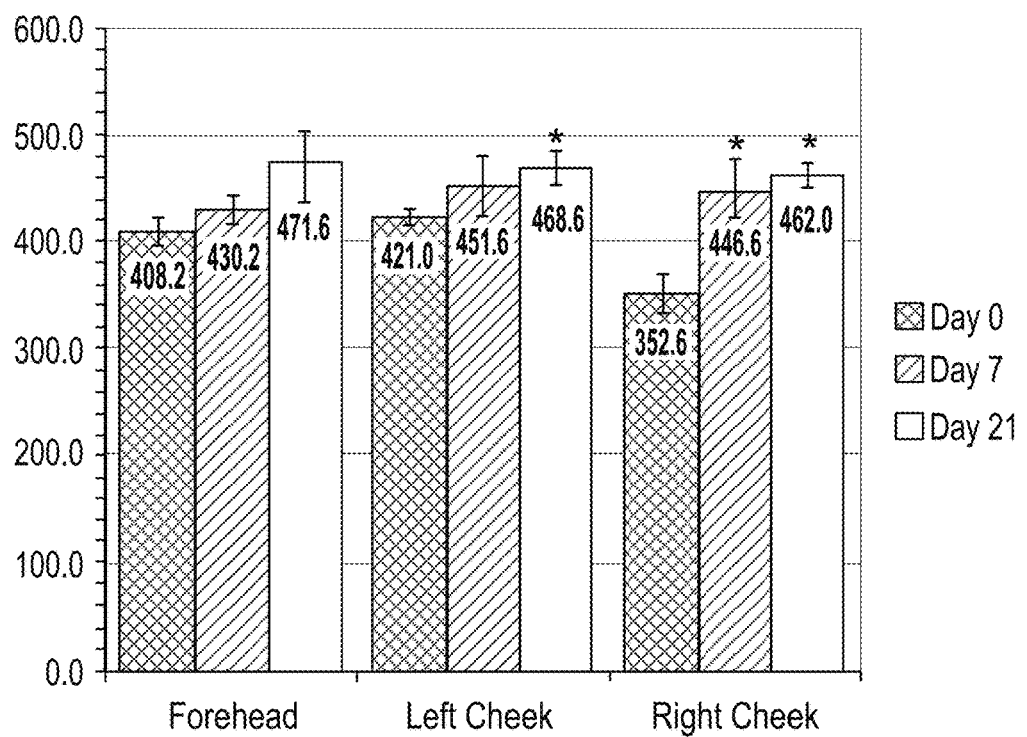
Figure 5A:
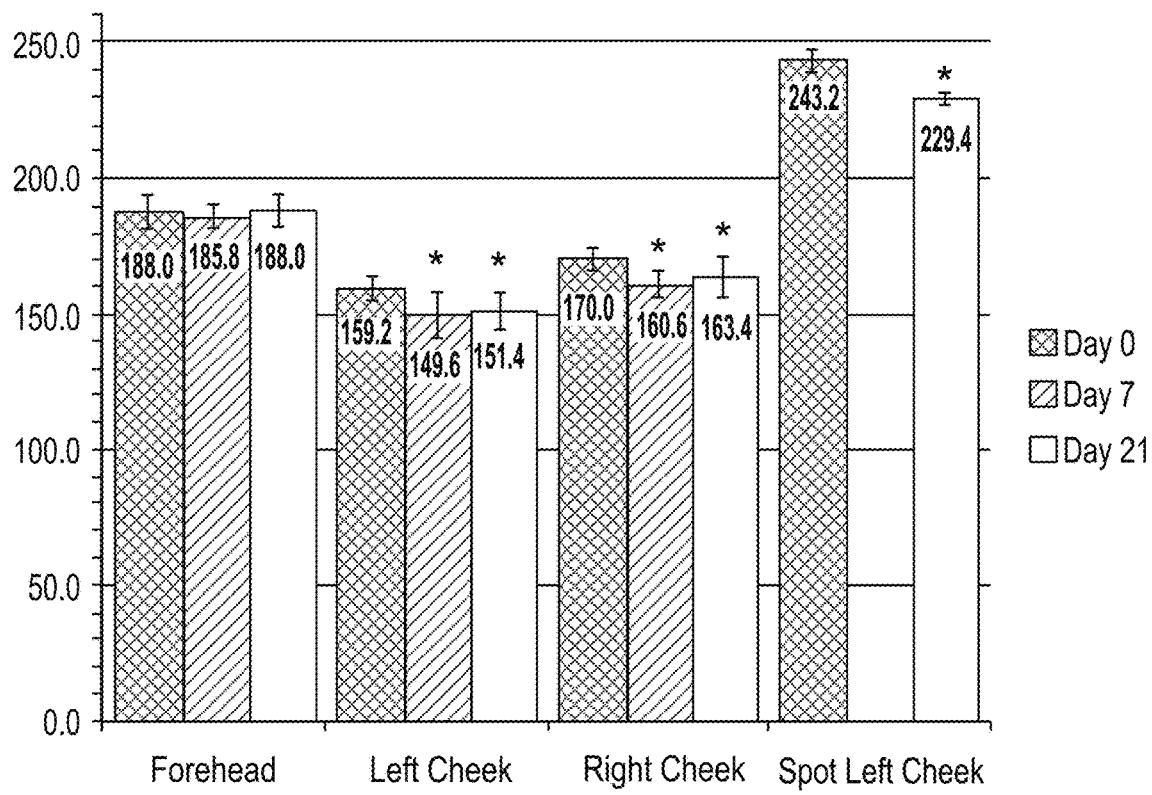
Figure 5B:
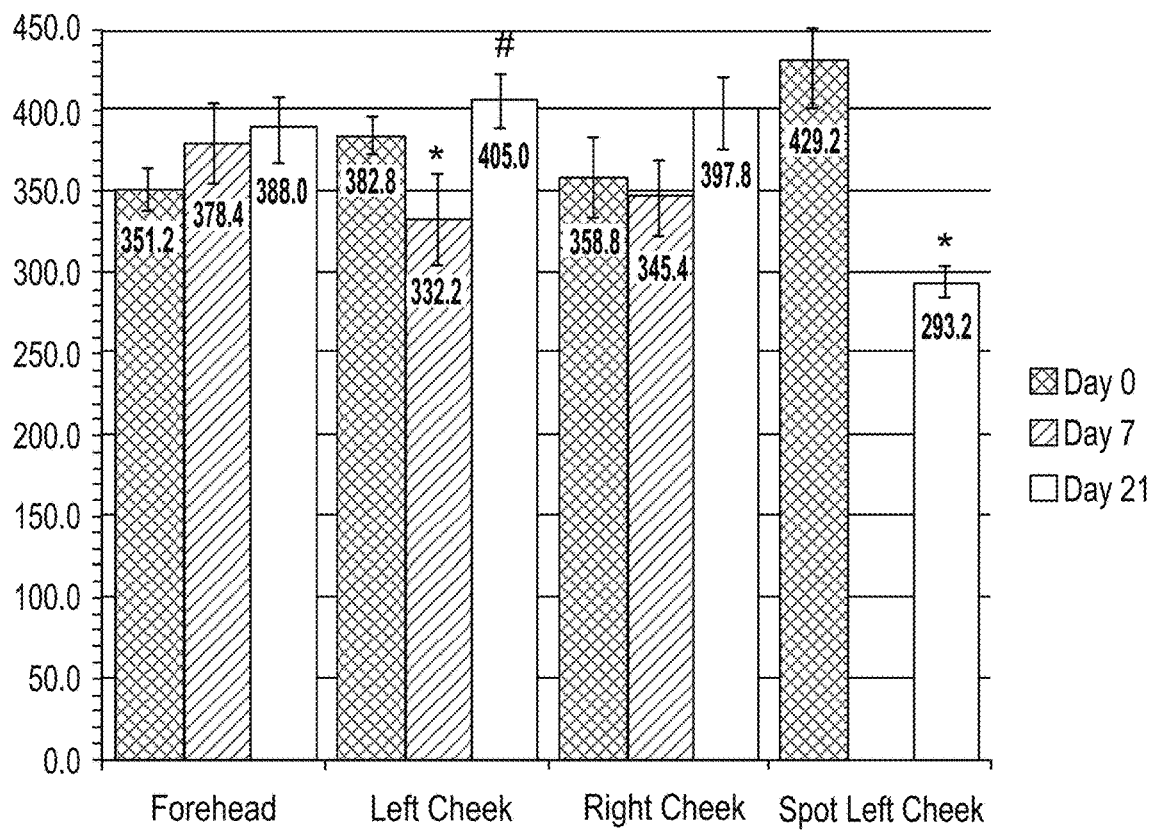
Figure 6A:
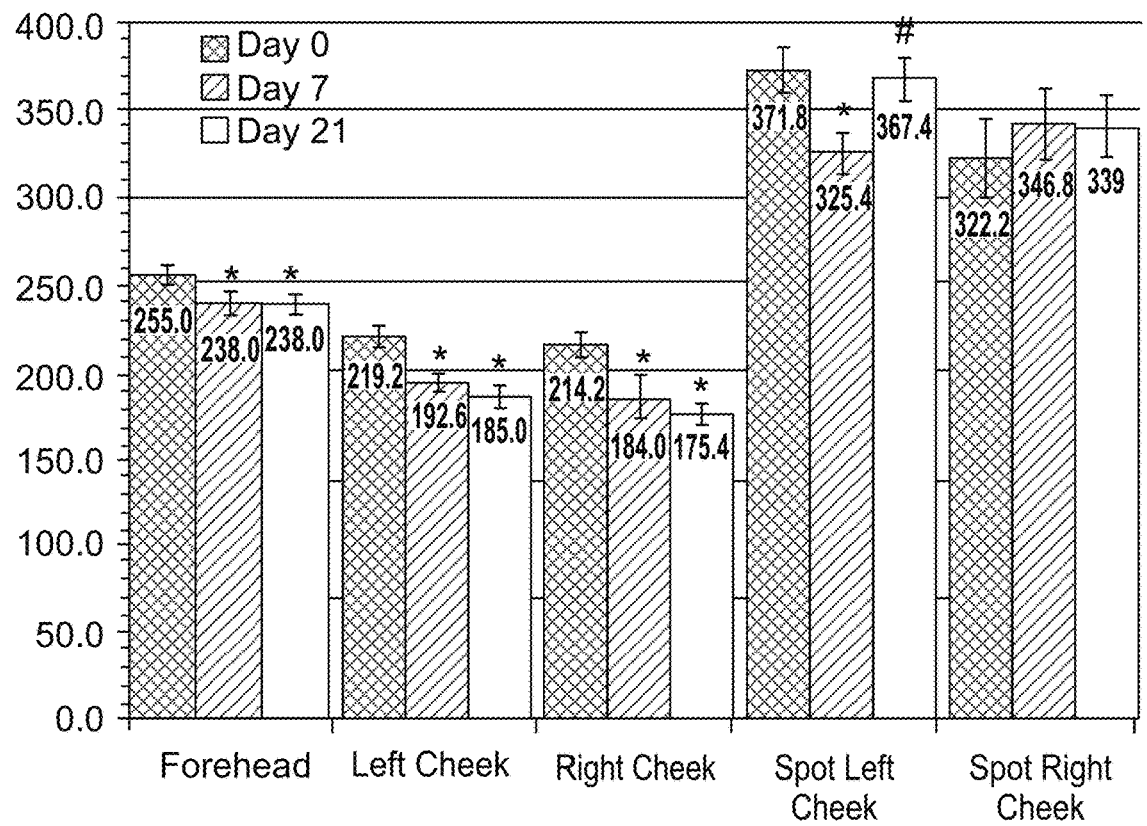
Figure 6B:
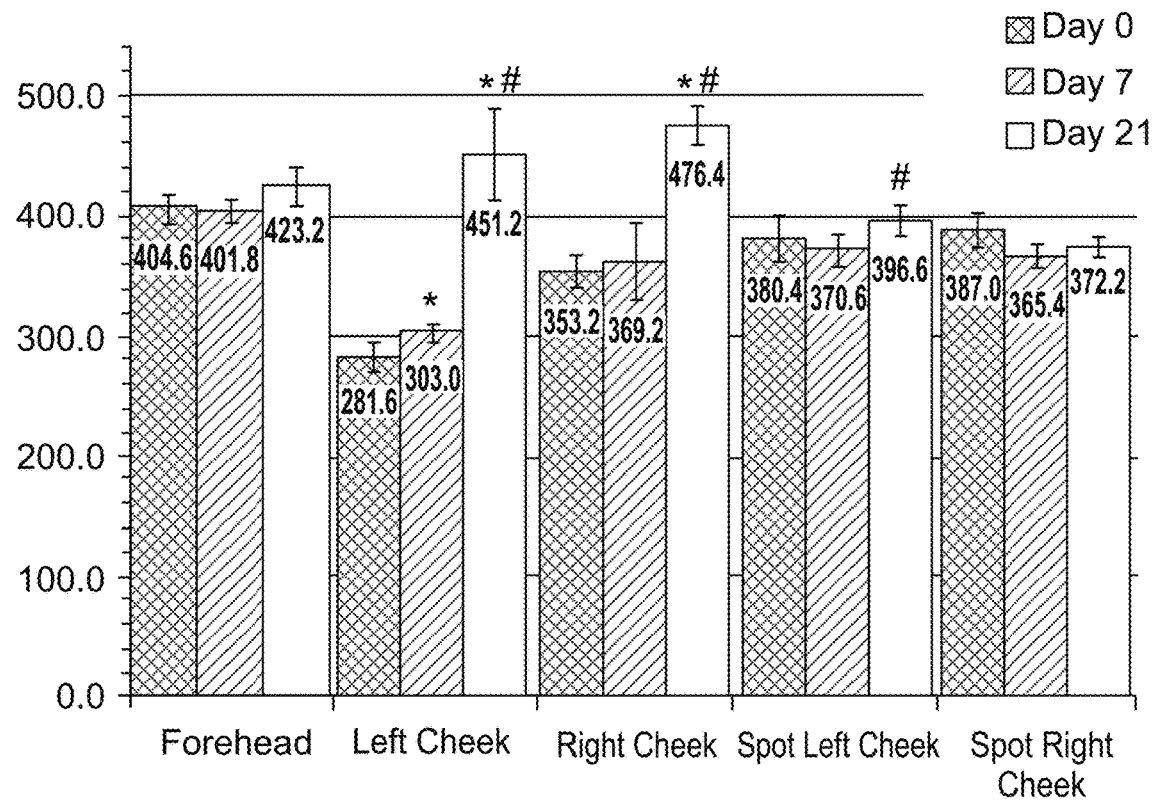
Figure 7A:
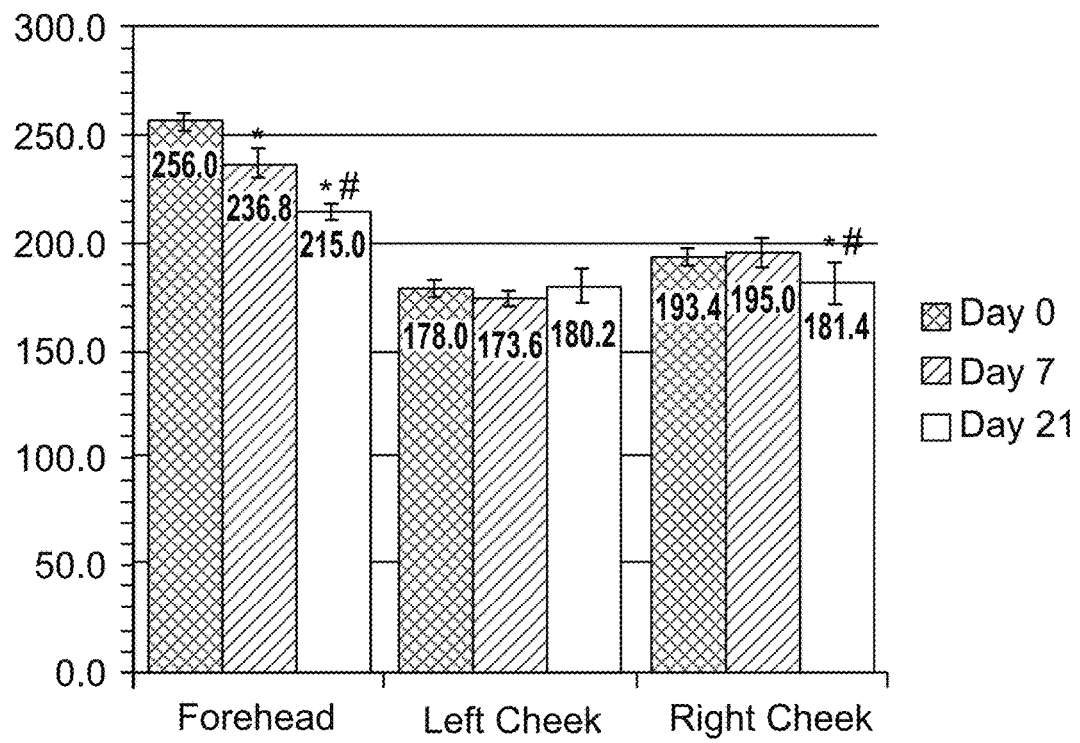
Figure 7B:
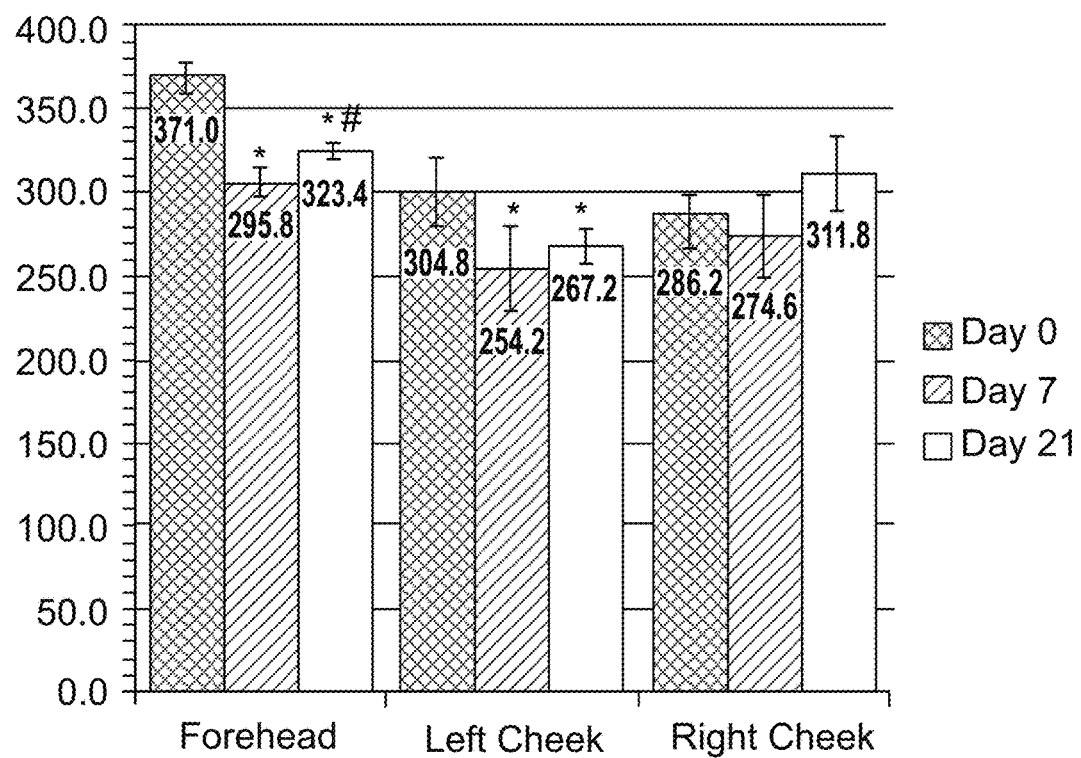
Figure 8A:
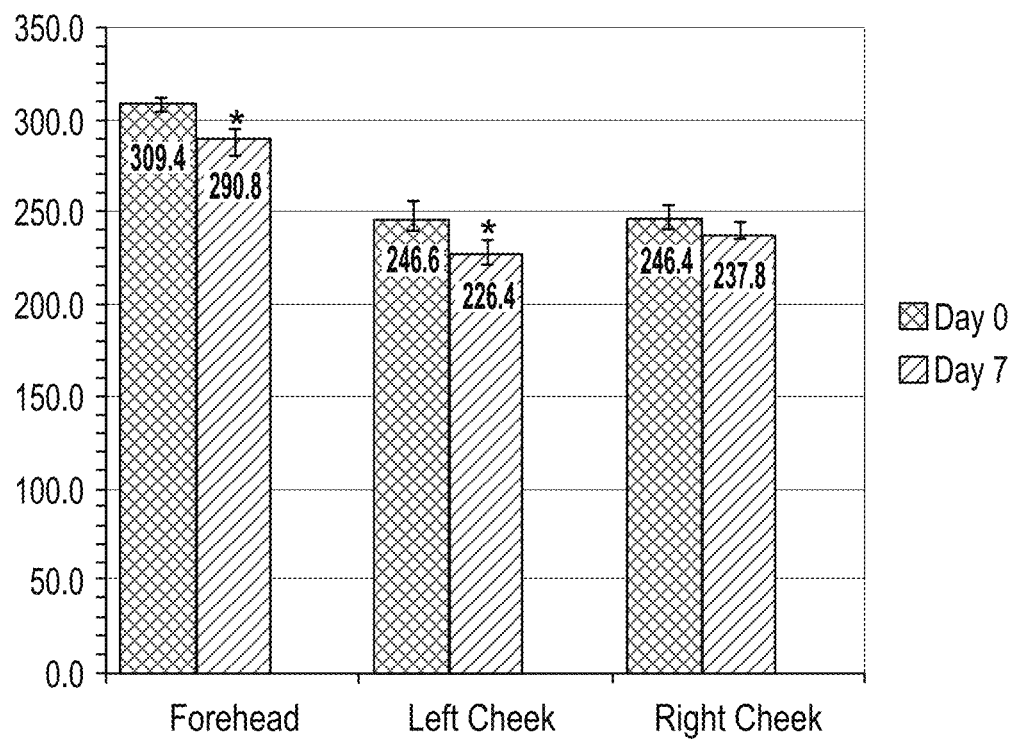
Figure 8B:
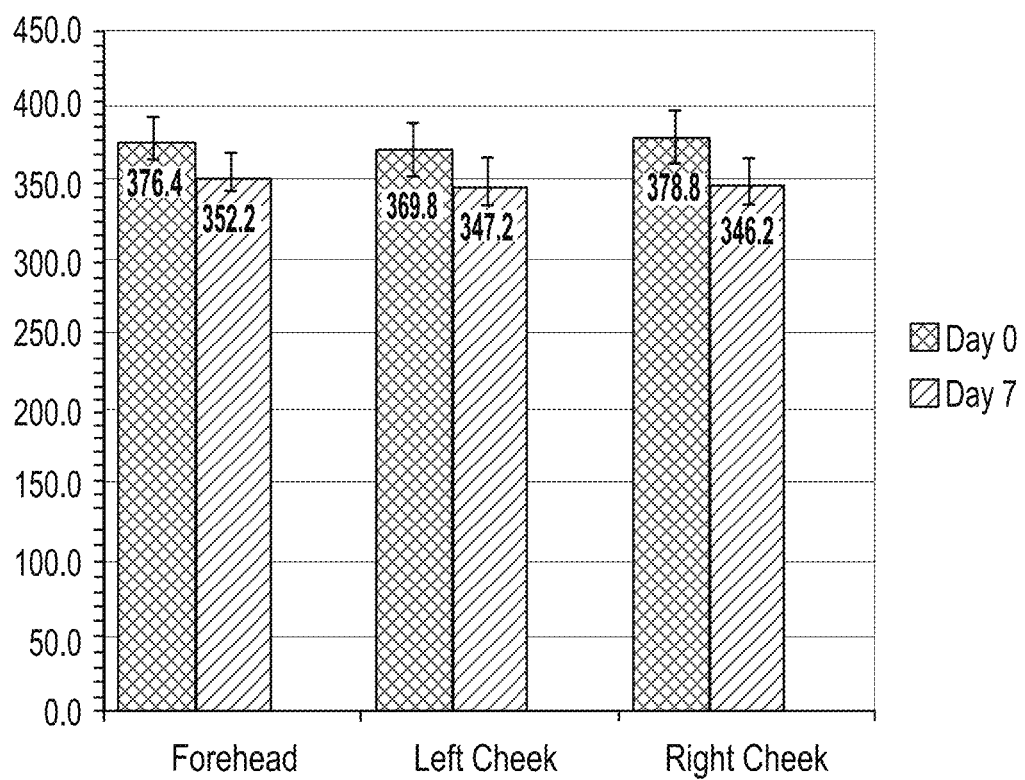
Figure 9A:
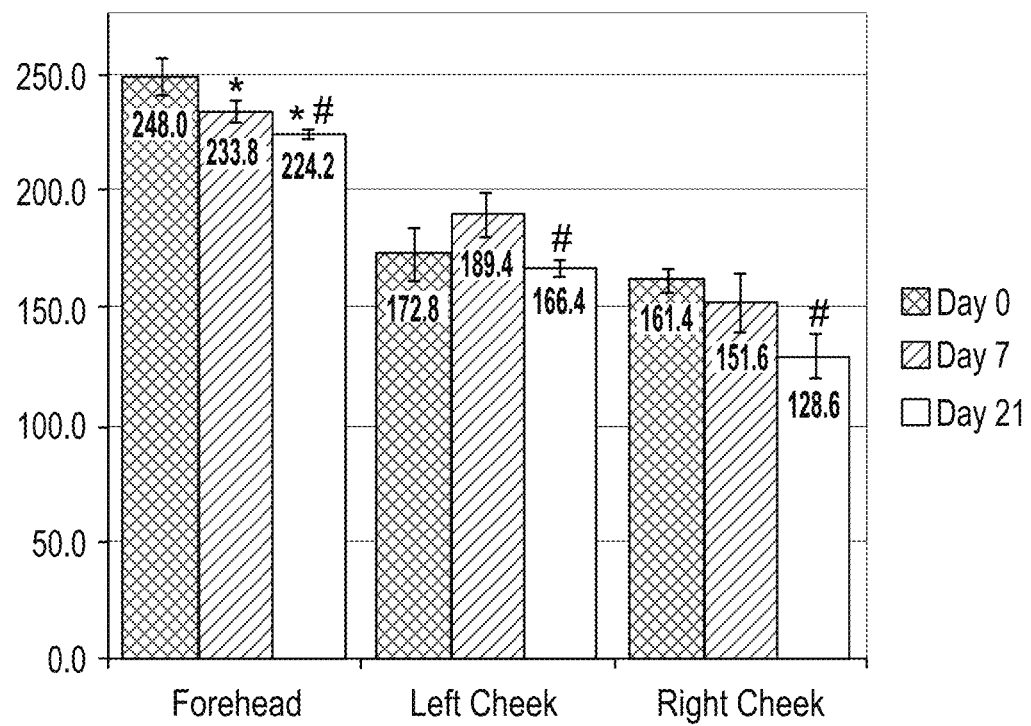
Figure 9B:
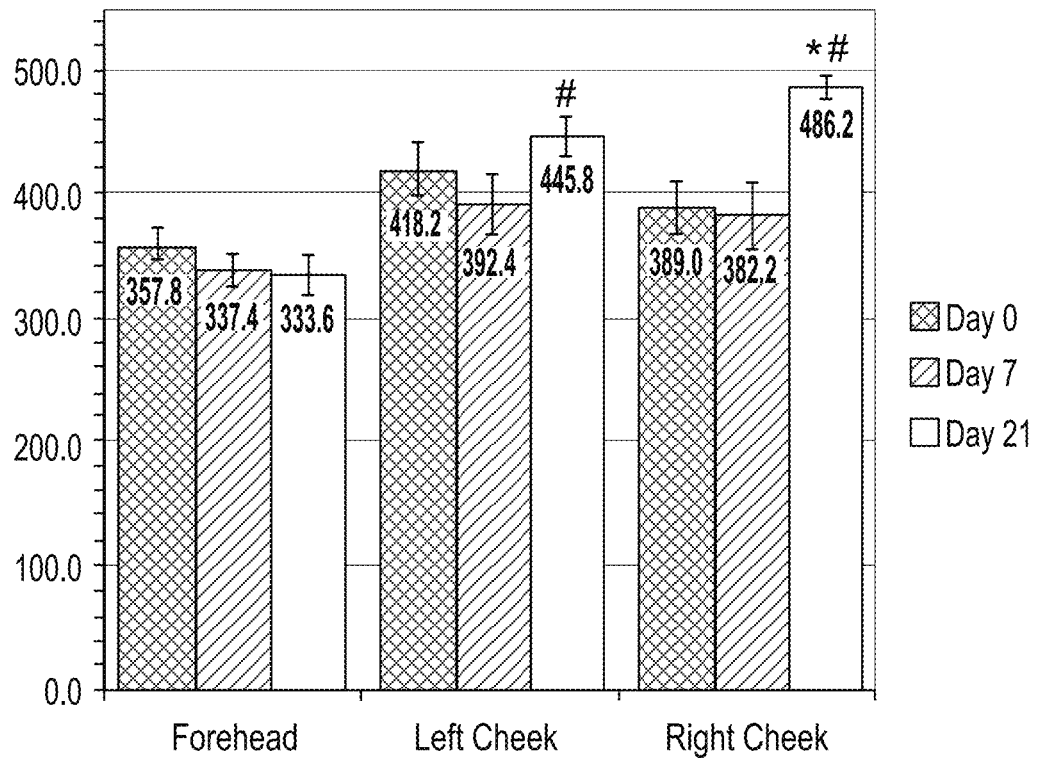
Figure 10A:
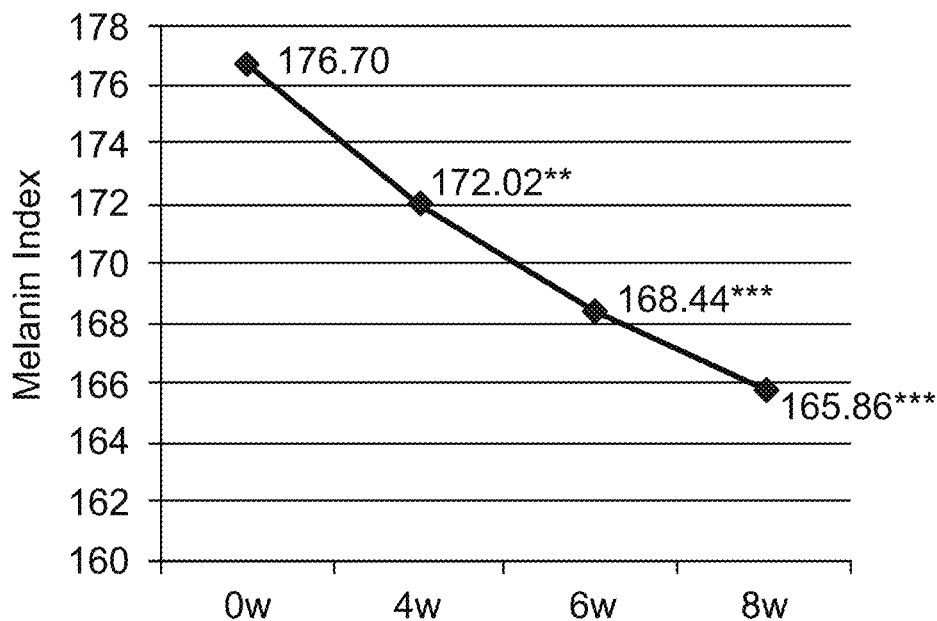
Figure 10B:
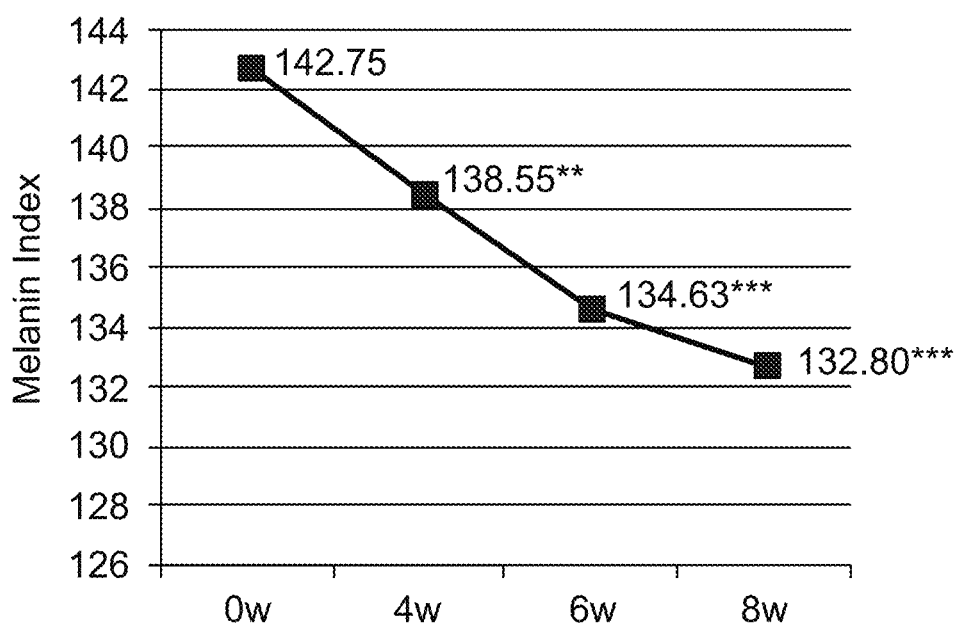
Figure 11:
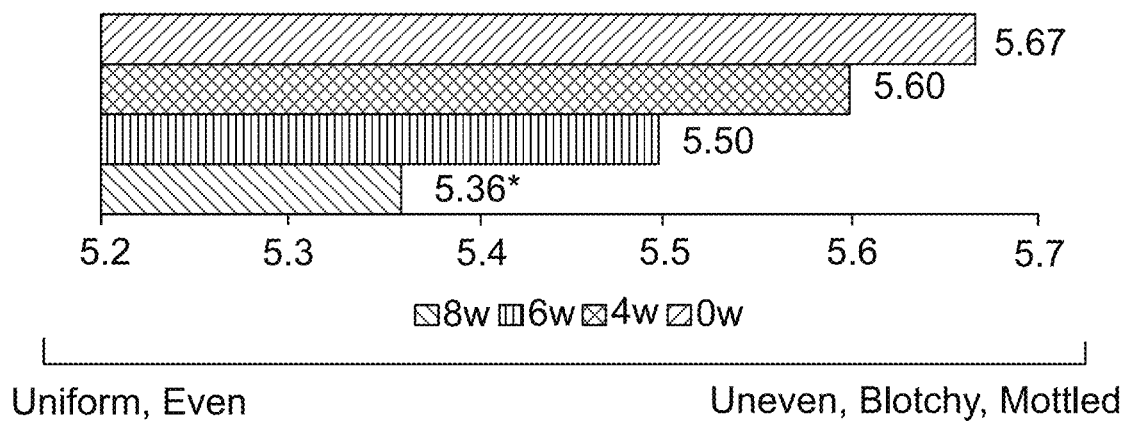
Figure 12:
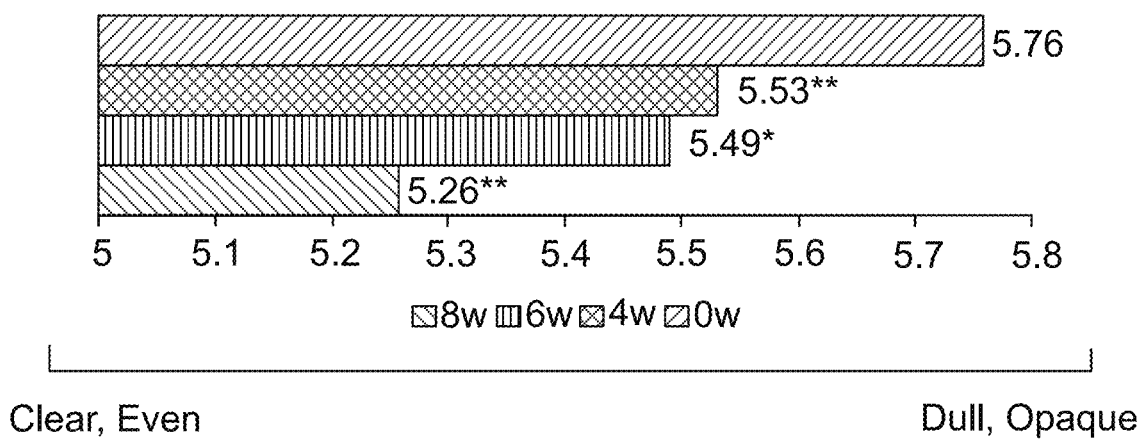
Figure 13:
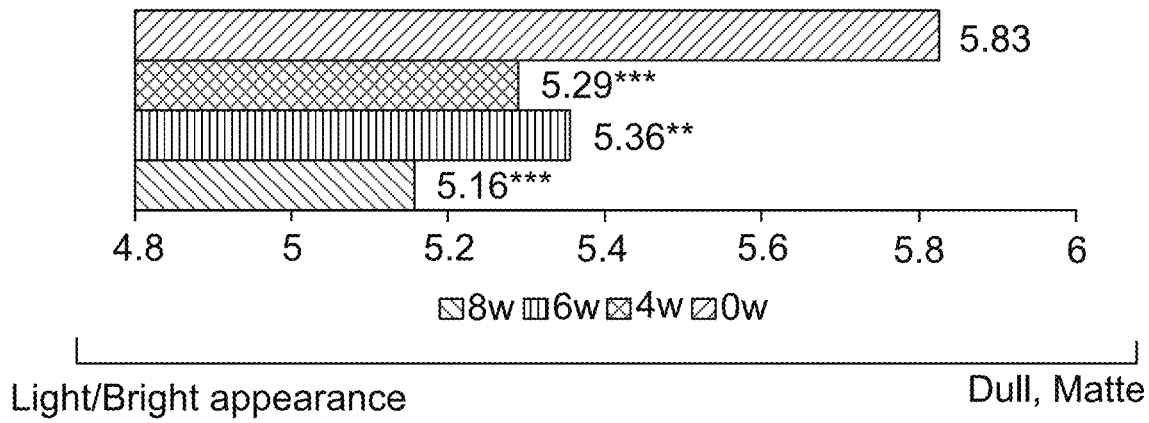
Figure 14:
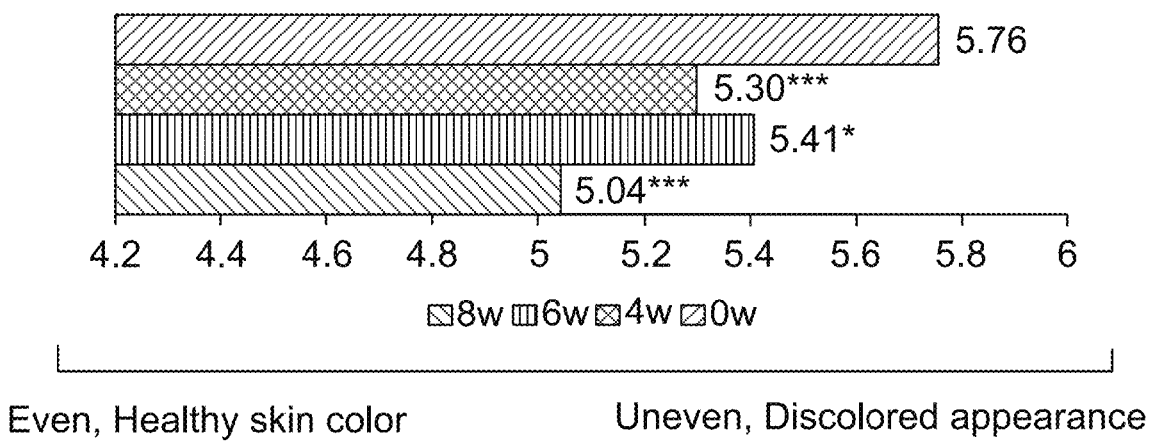
Figure 15:
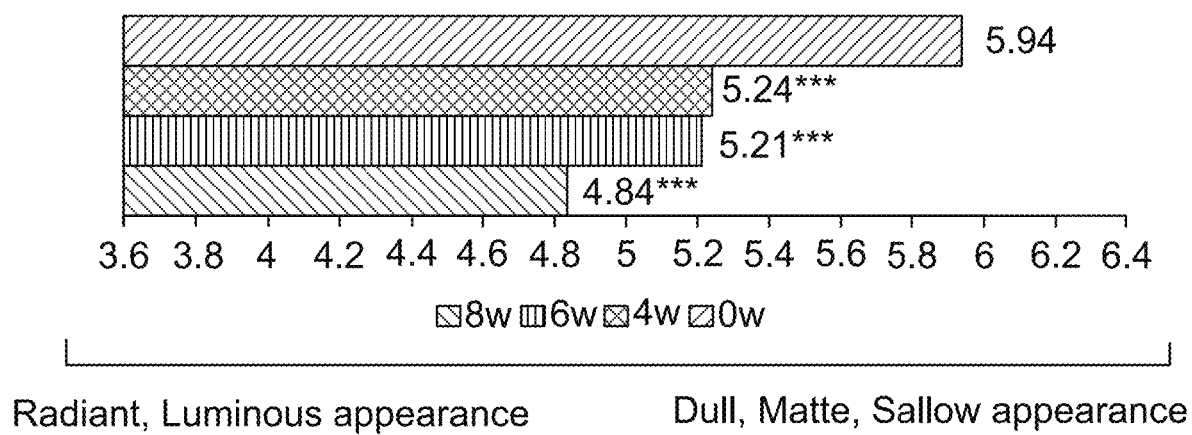
Figure 16:
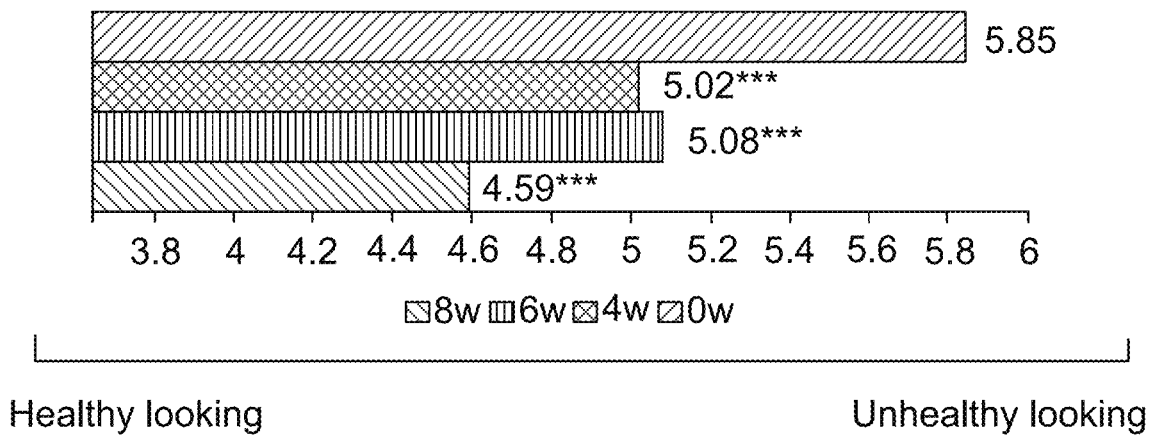
Figure 17:
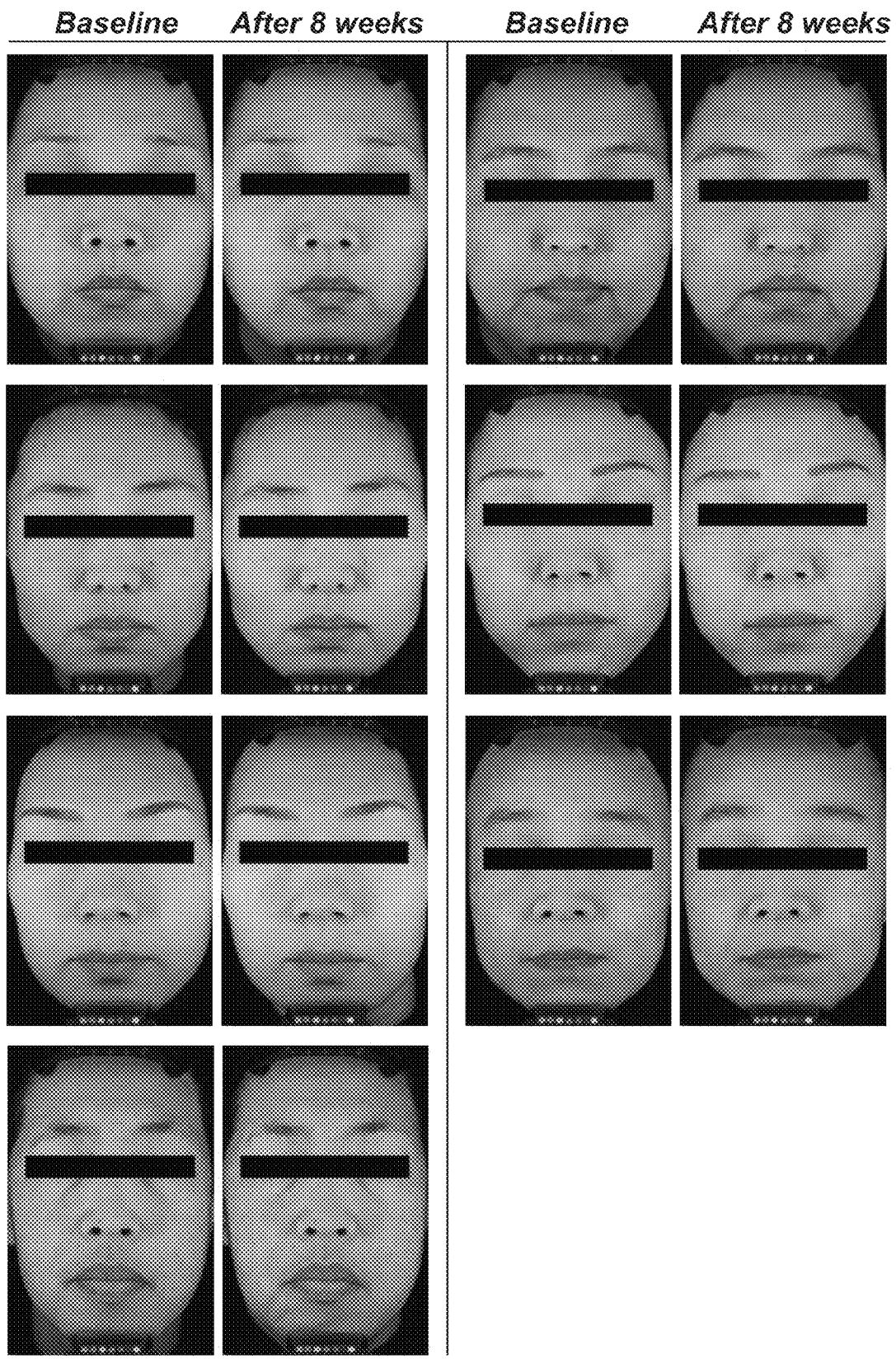

FIG. 1 presents images showing an exemplary enzyme cream comprising 25 units/gram lignin peroxidase (LIP) isoenzyme H1 fraction, 25 units/gram glucose oxidase (GOX) and 6 mmol/kg veratryl alcohol (VA) with 140 µg/ml melanin (LIP/VA/GOX) and an exemplary activator cream comprising 3.5 mmol/kg glucose (GLU), a control enzyme cream comprising 25 units/gram LIP isoenzyme H1 fraction and 6 mmol/kg VA with 140 µg/ml melanin (LIP/VA) and control activator cream comprising 3.53 mmol/kg $H_2O_2$, as well as a mixture of the exemplary enzyme and activator cream (LIP/VA/GOX/GLU) and a mixture of the control enzyme and activator cream (LIP/VA/$H_2O_2$);

FIGS. 2A and 2B present bar graphs showing values for a melanin index (FIG. 2A) and erythema index (FIG. 2B) in various facial regions of a subject on days 0, 7 and 21 of a treatment comprising administration twice per day of LIP isoenzyme H1, glucose oxidase and glucose, according to an exemplary embodiment of the invention (* $p<0.05$ vs. day 0);

FIGS. 3A and 3B present bar graphs showing values for a melanin index (FIG. 3A) and erythema index (FIG. 3B) in various facial regions of a subject on days 0 and 21 of a treatment comprising administration twice per day of LIP isoenzyme H1, glucose oxidase and glucose, according to an exemplary embodiment of the invention (* $p<0.05$ vs. day 0);

FIGS. 4A and 4B present bar graphs showing values for a melanin index (FIG. 4A) and erythema index (FIG. 4B) in various facial regions of a subject on days 0, 7 and 21 of a treatment comprising administration twice per day of LIP isoenzyme H1, glucose oxidase and glucose, according to an exemplary embodiment of the invention (* $p<0.05$ vs. day 0);

FIGS. 5A and 5B present bar graphs showing values for a melanin index (FIG. 5A) and erythema index (FIG. 5B) in various facial regions of a subject on days 0, 7 and 21 of a treatment comprising administration twice per day of LIP isoenzyme H1, glucose oxidase and glucose, according to an exemplary embodiment of the invention (* $p<0.05$ vs. day 0, # $p<0.05$ vs. day 7);

FIGS. 6A and 6B present bar graphs showing values for a melanin index (FIG. 6A) and erythema index (FIG. 6B) in various facial regions of a subject on days 0, 7 and 21 of a treatment comprising administration twice per day of LIP isoenzyme H1, glucose oxidase and glucose, according to an exemplary embodiment of the invention (* $p<0.05$ vs. day 0, # $p<0.05$ vs. day 7);

FIGS. 7A and 7B present bar graphs showing values for a melanin index (FIG. 7A) and erythema index (FIG. 7B) in various facial regions of a subject on days 0, 7 and 21 of a treatment comprising administration twice per day of LIP isoenzyme H1, glucose oxidase and glucose, according to an exemplary embodiment of the invention (* $p<0.05$ vs. day 0, # $p<0.05$ vs. day 7);

FIGS. 8A and 8B present bar graphs showing values for a melanin index (FIG. 8A) and erythema index (FIG. 8B) in various facial regions of a subject on days 0 and 7 of a treatment comprising administration twice per day of LIP isoenzyme H1, glucose oxidase and glucose, according to an exemplary embodiment of the invention (* $p<0.05$ vs. day 0);

FIGS. 9A and 9B present bar graphs showing values for a melanin index (FIG. 9A) and erythema index (FIG. 9B) in various facial regions of a subject on days 0, 7 and 21 of a treatment comprising administration twice per day of LIP isoenzyme H1, glucose oxidase and glucose, according to an exemplary embodiment of the invention (* $p<0.05$ vs. day 0, # $p<0.05$ vs. day 7; increase for erythema index in cheeks on day 21 due to irritation unrelated to treatment);

FIGS. 10A and 10B present graphs showing the melanin index of pigmented (FIG. 10A) and non-pigmented (FIG. 10B) skin after 0, 4, 6 and 8 weeks of a treatment comprising administration twice per day of LIP isoenzyme H1, glucose oxidase and glucose, according to an exemplary embodiment of the invention ( $p<0.01$ ($p=0.001$ in FIG. 10A and $p=0.007$ in FIG. 10B), * $p<0.001$);

FIG. 11 presents a visual analogue scale showing uniformity of pigmentation of skin, as judged by a dermatologist, after 0, 4, 6 and 8 weeks of a treatment comprising administration twice per day of LIP isoenzyme H1, glucose oxidase and glucose, according to an exemplary embodiment of the invention (0=uniform, even, 10=uneven, blotchy, mottled, * $p<0.05$);

FIG. 12 presents a visual analogue scale showing clarity of skin, as judged by a dermatologist, after 0, 4, 6 and 8 weeks of a treatment comprising administration twice per day of LIP isoenzyme H1, glucose oxidase and glucose, according to an exemplary embodiment of the invention (0=clear, even, 10=dull, opaque, * $p<0.05$, ** $p<0.01$);

FIG. 13 presents a visual analogue scale showing lightening/brightening of skin, as judged by a dermatologist, after 0, 4, 6 and 8 weeks of a treatment comprising administration twice per day of LIP isoenzyme H1, glucose oxidase and glucose, according to an exemplary embodiment of the invention (0=light/bright appearance, 10=dull, matte,  $p<0.01$, * $p<0.001$);

FIG. 14 presents a visual analogue scale showing skin tone, as judged by a dermatologist, after 0, 4, 6 and 8 weeks of a treatment comprising administration twice per day of LIP isoenzyme H1, glucose oxidase and glucose, according to an exemplary embodiment of the invention (0=even, healthy skin color, 10=uneven, discolored appearance, * $p<0.05$, *** $p<0.001$);

FIG. 15 presents a visual analogue scale showing radiance of skin, as judged by a dermatologist, after 0, 4, 6 and 8 weeks of a treatment comprising administration twice per day of LIP isoenzyme H1, glucose oxidase and glucose, according to an exemplary embodiment of the invention (0=radiant, luminous appearance, 10=dull, matte, sallow appearance, *** $p<0.001$);

FIG. 16 presents a visual analogue scale showing overall appearance of skin, as judged by a dermatologist, after 0, 4, 6 and 8 weeks of a treatment comprising administration twice per day of LIP isoenzyme H1, glucose oxidase and glucose, according to an exemplary embodiment of the invention (0=healthy looking, 10=unhealthy looking, * $p<0.001$); and FIG. 17** presents photographs of subjects before (baseline) and after 8 weeks of a treatment comprising administration twice per day of LIP isoenzyme H1, glucose oxidase and glucose, according to an exemplary embodiment of the invention.

DESCRIPTION OF SPECIFIC EMBODIMENTS OF THE INVENTION

The present invention, in some embodiments thereof, relates to novel cosmetic compositions, kits and methods and, more particularly, but not exclusively, to hydrogen peroxide-producing cosmetic compositions, kits and methods, and to uses thereof in, for example, lightening skin and/or hair.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Methods for lightening a skin of a subject, using hydrogen peroxide and a lignin peroxidase, have been previously disclosed (see, for example, International Patent Application Publication WO 2012/153336, discussed hereinabove). Such methods require utilization of compositions containing hydrogen peroxide.

Many other cosmetic compositions and methods include or utilize hydrogen peroxide.

However, utilizing hydrogen peroxide in cosmetic applications has recently been recognized as undesired.

In a search for methodologies in which the need to utilize compositions containing hydrogen peroxide is circumvented, the present inventors have envisioned and successfully devised and practiced a novel methodology which utilizes an enzymatic system for generating hydrogen peroxide upon application. More specifically, the present inventors have utilized a hydrogen peroxide-producing enzyme and a substrate thereof, for generating hydrogen peroxide in situ, immediately prior to application of a composition or system containing same and/or during application of a composition or system containing same. The enzymatic system is readily controllable by keeping the enzyme and substrate separate, until hydrogen peroxide generation is desired and/or by keeping the enzyme and the substrate inactive towards one another, by storage in the absence of oxygen. The herein disclosed methodology is advantageous by being capable of generating the hydrogen peroxide gradually in situ, where it is consumed, such that a concentration of hydrogen peroxide remains low and stable over time.

While reducing the present invention to practice, the inventors have demonstrated the efficacy of an enzymatic system for generating hydrogen peroxide for activating lignin peroxidase in order to lighten skin.

Thus, as shown in the Examples section which follows, the present inventors have designed a cosmetic composition which comprises lignin peroxidase, and an activator composition which comprises glucose, which when applied together (e.g., on a skin region of a subject) results in a significant whitening effect as a result of reduction in melanin content (FIGS. 1-9B), due to the interaction of lignin peroxidase with hydrogen peroxide generated by the glucose oxidase and glucose.

These results demonstrate the efficacy of using an enzyme/substrate system for generating hydrogen peroxide in situ (i.e., in or on a region of the body where it is intended to react (e.g., with melanin in a peroxidase-catalyzed reaction).

According to an aspect of some embodiments of the invention, there is provided a cosmetic or pharmaceutical composition for topical application (e.g., for application to skin, hair and/or nail of a subject). According to some embodiments of the present invention, the composition comprises a hydrogen peroxide-producing enzymatic system, namely, a hydrogen peroxide-producing enzyme and a substrate of the hydrogen peroxide-producing enzyme.

As used herein throughout, the term "cosmetic" with regard to any of the compositions, kits and methods (and any other aspect) disclosed herein, refers to compositions, kits and method which enhance the appearance or odor of the human body.

In some embodiments, the term "cosmetic" follows the definition regulatory authorities worldwide. For example, in some embodiments, the term "cosmetic" follows the definition of the U.S. Food and Drug Administration (FDA), as being "intended to be applied to the human body for cleansing, beautifying, promoting attractiveness, or altering the appearance without affecting the body's structure or functions".

The Hydrogen Peroxide Producing Enzymatic System:

As used herein throughout, the phrase "hydrogen peroxide-producing enzyme" refers to an enzyme which catalyzes a reaction in which hydrogen peroxide is a product.

As used herein throughout, the "substrate" of a hydrogen peroxide-producing enzyme refers to any compound other than $O_2$ or water which serves as a substrate for the above-mentioned reaction catalyzed by the hydrogen peroxide-producing enzyme in which hydrogen peroxide is a product. The "substrate" may be a single compound or a plurality of compounds. The plurality of compounds may interact with the enzyme as part of different reactions, or the enzyme catalyzes a single reaction which utilizes a plurality of compounds as substrates.

In some embodiments, the enzyme catalyzes a reaction in which the substrate is oxidized and $O_2$ is reduced to hydrogen peroxide.

In some embodiments, the enzyme catalyzes a reaction in which the substrate is reduced and water is oxidized to hydrogen peroxide.

Examples of hydrogen peroxide-producing enzymes which may be used in embodiments of the invention include, without limitation:

an EC 1.1.3 oxidoreductase such as, for example, a glucose oxidase (EC 1.1.3.4), a hexose oxidase (EC 1.1.3.5), a cholesterol oxidase (EC 1.1.3.6), an aryl alcohol oxidase (EC 1.1.3.7), an L-gulonolactone oxidase (EC 1.1.3.8), a galactose oxidase (EC 1.1.3.9), a pyranose-2-oxidase (EC 1.1.3.10), a pyridoxine-4-oxidase (EC 1.1.3.12), an alcohol oxidase (EC 1.1.3.13), a 2-hydroxy-acid oxidase (EC 1.1.3.15), a choline oxidase (EC 1.1.3.17), a long-chain-alcohol oxidase (EC 1.1.3.20), a glycerol-3-phosphate oxidase (EC 1.1.3.21), a D-arabinono-1,4-lactone oxidase (EC 1.1.3.37), a vanillyl alcohol oxidase (EC 1.1.3.38), an alditol oxidase (EC 1.1.3.41), a prosolanapyrone II oxidase (EC 1.1.3.42), a paromamine 6'-oxidase (EC 1.1.3.43), a glyoxal oxidase and a veratryl alcohol oxidase;
an alcohol dehydrogenase (EC 1.1.99.8);
a cellobiose dehydrogenase (EC 1.1.99.18);

an EC 1.2.3 oxidoreductase such as, for example, an aldehyde oxidase (EC 1.2.3.1), an oxalate oxidase (EC 1.2.3.4), and an aryl aldehyde oxidase (EC 1.2.3.9);

an EC 1.3.3 oxidoreductase such as, for example, a dihydroorotate oxidase (EC 1.3.3.1), and a pyrroloquinoline-quinone synthase (EC 1.3.3.11);

an EC 1.4.3 oxidoreductase such as, for example, an L-amino acid oxidase (EC 1.4.3.2), and an L-glutamate oxidase (1.4.3.11);

an EC 1.5.3 oxidoreductase such as, for example, a polyamine oxidase (1.5.3.11);

an EC 1.6.3 oxidoreductase such as, for example, an NAD(P)H oxidase (1.6.3.1);

an EC 1.7.3 oxidoreductase such as, for example, a urate oxidase (EC 1.7.3.3), and a hydroxylamine oxidase (EC 1.7.3.4);

an EC 1.8.3 oxidoreductase such as, for example, a thiol oxidase (EC 1.8.3.2), and a glutathione oxidase (EC 1.8.3.3);

an EC 1.9.3 oxidoreductase, such as, for example, a cytochrome c oxidase (EC 1.9.3.1);

an EC 1.17.3 oxidoreductase such as, for example, a xanthine oxidase (EC 1.17.3.2); and a superoxide dismutase (EC 1.15.1.1).

The EC nomenclature herein is according to the International Union of Biochemistry and Molecular Biology.

In some embodiments, the hydrogen peroxide-producing enzyme is one or more of an EC 1.1.3 oxidoreductase, an EC 1.2.3 oxidoreductase, an EC 1.3.3 oxidoreductase, an EC 1.4.3 oxidoreductase, an EC 1.5.3 oxidoreductase, an EC 1.6.3 oxidoreductase, an EC 1.7.3 oxidoreductase, an EC 1.8.3 oxidoreductase, an EC 1.9.3 oxidoreductase and an EC 1.17.3 oxidoreductase (e.g., such as an oxidoreductase described herein).

In some embodiments a superoxide dismutase is included for producing hydrogen peroxide from superoxide, in combination with a source of superoxide. In some embodiments, the source of superoxide is an enzyme which produces superoxide, for example, an NAD(P)H oxidase and/or a xanthine oxidase.

In some embodiments, the hydrogen peroxide-producing enzyme produces superoxide. As superoxide normally reacts to a considerable degree to form hydrogen peroxide (e.g., by dismutation), production of superoxide is considered herein to encompass production of hydrogen peroxide.

Suitable substrates of the hydrogen peroxide-producing enzyme will be apparent to the skilled person.

In exemplary embodiments, the enzyme is a glucose oxidase (EC 1.1.3.4) and the substrate comprises D-glucose.

In some embodiments, the enzyme is a hexose oxidase (EC 1.1.3.5) and the substrate comprises D-glucose, D-galactose, D-mannose, maltose, lactose and/or cellobiose.

In some embodiments, the enzyme is a cholesterol oxidase (EC 1.1.3.6) and the substrate comprises cholesterol.

In some embodiments, the enzyme is an aryl alcohol oxidase (EC 1.1.3.7) and the substrate comprises an aromatic primary alcohol.

In some embodiments, the enzyme is an L-gulonolactone oxidase (EC 1.1.3.8) and the substrate comprises L-gulono-1,4-lactone.

In some embodiments, the enzyme is a galactose oxidase (EC 1.1.3.9) and the substrate comprises a primary alcohol (e.g., methanol, ethanol, n-propanol, n-butanol, isobutanol), a monosaccharide, an oligosaccharide and/or a polysaccharide.

In some embodiments, the enzyme is a pyranose-2-oxidase (EC 1.1.3.10) and the substrate comprises an aldopyranose (e.g., D-glucose, D-xylose, D-galactose), L-sorbose and/or 1,5-anhydroglucitol, and/or disaccharides thereof. It is to be appreciated that pyranose-2-oxidase is a natural source for hydrogen peroxide for activating lignin cellulose.

In some embodiments, the enzyme is a pyridoxine-4-oxidase (EC 1.1.3.12) and the substrate comprises pyridoxine.

In some embodiments, the enzyme is an alcohol oxidase (EC 1.1.3.13) and the substrate comprises a primary alcohol (e.g., methanol, ethanol, n-propanol, n-butanol, isobutanol).

In some embodiments, the enzyme is a 2-hydroxy-acid oxidase (EC 1.1.3.15) and the substrate comprises an (S)-2-hydroxy acid (e.g., glycolate, 2-hydroxyglutarate) and/or an (S)-2-amino acid.

In some embodiments, the enzyme is a choline oxidase (EC 1.1.3.17) and the substrate comprises choline and/or glycine betaine aldehyde.

In some embodiments, the enzyme is a long-chain-alcohol oxidase (EC 1.1.3.20) and the substrate is a long-chain alcohol (e.g., a fatty alcohol).

In some embodiments, the enzyme is a glycerol-3-phosphate oxidase (EC 1.1.3.21) and the substrate comprises glycerol-3-phosphate.

In some embodiments, the enzyme is a D-arabinono-1,4-lactone oxidase (EC 1.1.3.37) and the substrate comprises L-gulono-1,4-lactone, D-arabinono-1,4-lactone, and/or L-galactono-1,4-lactone.

In some embodiments, the enzyme is a vanillyl alcohol oxidase (EC 1.1.3.38) and the substrate comprises a 4-allylphenol, a 4-hydroxybenzyl alcohol (e.g., vanillyl alcohol), a 4-hydroxybenzamine and/or a 4-(methoxymethyl)phenol.

In some embodiments, the enzyme is an alditol oxidase (EC 1.1.3.41) and the substrate comprises an alditol (e.g., xylitol, D-sorbitol).

In some embodiments, the enzyme is a prosolanapyrone II oxidase (EC 1.1.3.42) and the substrate comprises prosolanapyrone II.

In some embodiments, the enzyme is a paromamine 6'-oxidase (EC 1.1.3.43) and the substrate comprises paromamine and/or 6'''-deamino-6'''hydroxyneomycin C.

In some embodiments, the enzyme is a veratryl alcohol oxidase and the substrate is a primary (4-methoxy)-aromatic alcohol (e.g., veratryl alcohol).

In some embodiments, the enzyme is a glyoxal oxidase and the substrate is glyoxal, an alkyl glyoxal (e.g., methyl glyoxal) and/or cellobiose.

In some embodiments, the enzyme is an alcohol dehydrogenase (EC 1.1.99.8) and the substrate comprises a primary alcohol (e.g., methanol, ethanol, n-propanol, n-butanol, isobutanol).

In some embodiments, the enzyme is a cellobiose dehydrogenase (EC 1.1.99.18) and the substrate comprises cellobiose, a cello-oligosaccharide, lactose, and/or D-glucosyl-1,4-β-D-mannose.

In some embodiments, the enzyme is an aldehyde oxidase (EC 1.2.3.1) and the substrate comprises an aldehyde.

In some embodiments, the enzyme is an oxalate oxidase (EC 1.2.3.4) and the substrate comprises oxalate.

In some embodiments, the enzyme is an aryl aldehyde oxidase (EC 1.2.3.9) and the substrate comprises an aromatic aldehyde (e.g., benzaldehyde, vanillin).

In some embodiments, the enzyme is a dihydroorotate oxidase (EC 1.3.3.1) and the substrate comprises dihydroorotate.

In some embodiments, the enzyme is a pyrroloquinoline-quinone synthase (EC 1.3.3.11) and the substrate comprises 6-(2-amino-2-carboxyethyl)-7,8-dioxo-1,2,3,4,7,8-hexahydroquinoline-2,4-dicarboxylate.

In some embodiments, the enzyme is an L-amino acid oxidase (EC 1.4.3.2) and the substrate comprises an L-amino acid.

In some embodiments, the enzyme is an L-glutamate oxidase (1.4.3.11) and the substrate comprises L-glutamate.

In some embodiments, the enzyme is a polyamine oxidase (1.5.3.11) and the substrate comprises $N_1$-acetylspermine.

In some embodiments, the enzyme is an NAD(P)H oxidase (1.6.3.1) and the substrate comprises NADH and/or NADPH.

In some embodiments, the enzyme is a urate oxidase (EC 1.7.3.3) and the substrate comprises urate.

In some embodiments, the enzyme is a hydroxylamine oxidase (EC 1.7.3.4) and the substrate comprises a hydroxylamine.

In some embodiments, the enzyme is a thiol oxidase (EC 1.8.3.2) and the substrate comprises a thiol group.

In some embodiments, the enzyme is a glutathione oxidase (EC 1.8.3.3) and the substrate comprises glutathione and/or cysteine.

In some embodiments, the enzyme is a cytochrome c oxidase (EC 1.9.3.1) and the substrate comprises ferrocytochrome c.

In some embodiments, the enzyme is a xanthine oxidase (EC 1.17.3.2) and the substrate comprises xanthine and/or hypoxanthine.

The hydrogen peroxide-producing enzyme described herein (e.g., glucose oxidase) may be obtained, for example, from a commercial supplier, by extraction from a natural source, and/or by recombinant expression. General procedures for expressing a protein are described in detail hereinafter, and may be used for expressing a hydrogen peroxide-producing enzyme described herein.

The Hydrogen Peroxide Producing Compositions:

A hydrogen peroxide-producing composition as described herein produces hydrogen peroxide whenever the hydrogen peroxide-producing enzyme and its substrate contact one another in the presence of oxygen (or air) and/or water.

It is to be understood that a hydrogen peroxide-producing composition according to any one of the embodiments relating to such compositions (e.g., as described in this section) may utilize a hydrogen peroxide-producing system according to any one of the embodiments described herein relating to such systems.

In some embodiments of any of the embodiments described herein, any of the composition described herein is prepared in situ, that is, on the site of application (e.g., skin, hair and/or nail) of the subject, by contacting different components of the composition with each other. In some embodiments, hydrogen peroxide generation begins only upon contacting the hydrogen peroxide-producing enzyme with the substrate thereof in situ.

In some embodiments of any of the embodiments described herein, the composition is prepared on the site of application (e.g., skin, hair and/or nail) of the subject, by contacting the application site with a part of the composition that comprises the enzyme and thereafter contacting the application site with a part of the composition that comprises the enzyme's substrate, or vice versa, contacting the application site with a part of the composition that comprises the enzyme's substrate and thereafter contacting the application site with a part of the composition that comprises the enzyme.

In some embodiments of any of the embodiments described herein, the composition is prepared shortly before being contacted with the application site (e.g., skin, hair and/or nail) of the subject, by contacting a part of the composition that comprises the enzyme's substrate with a part of the composition that comprises the enzyme's substrate, and thereafter contacting the resulting composition with the application site (e.g., skin, hair and/or nail) of a subject.

The composition may be prepared from components packaged in a kit, as described in further detail hereinunder.

In some embodiments of any of the embodiments described herein, the composition is packaged in a container, and can be used well after packaging.

In some of any of these embodiments, a composition comprises the hydrogen peroxide-producing enzyme in contact with its substrate, but the enzyme in the composition is inhibited from producing hydrogen peroxide due to a lack of oxygen in the container.

In some embodiments of any of the embodiments described herein, the container is air-tight, in order to limit the amount of oxygen which can be used by the enzyme to produce hydrogen peroxide.

Herein, the term "air-tight" refers to a packaging and/or container sealed in such a manner such that there are no openings which allow gases such as oxygen to enter or escape, and wherein packaging and/or container is formed of a material which is substantially impermeable to such gases.

In some embodiments of any of the embodiments described herein, air is evacuated from the packaging and/or container before sealing, for example, by subjecting the packaging and/or container to a reduced pressure and/or by purging the packaging and/or container with a gas which does not contain oxygen (e.g., nitrogen).

In some embodiments of any of the embodiments described herein, the air-tight container is configured for dispensing the composition (e.g., dispensing more than once) without entry of air into the container, so as to avoid production of hydrogen peroxide in the container after dispensing some of the composition.

In some embodiments of any of the embodiments described herein, the container has a volume which decreases upon dispensing, such that the container has little or no room for air to enter, even when the volume of the composition in the container decreases upon dispensing. Examples of such containers include, for example, a flexible tube (e.g., similar to a toothpaste tube) which dispenses a composition when subjected to pressure, and a container comprising a piston which moves when dispensing a composition.

In some embodiments of any of the embodiments described herein, an opening of the container (e.g., a nozzle) comprises a valve configured so as to be open only when a composition is exiting the container through the opening, at which time the composition being dispensed obstructs air from entering through the opening.

In some embodiments of any of the embodiments described herein, a composition comprises the hydrogen peroxide-producing enzyme in contact with its substrate, but the enzyme in the composition is inhibited from producing hydrogen peroxide due to a lack of water or humidity in the container. Means for packaging in non-humid environment are well known in the art.

In embodiments where the composition is packaged in a container, the container can be identified for use in any cosmetic application that requires hydrogen peroxide, as described in further detail hereinafter.

The concentrations of the hydrogen peroxide-producing enzyme and the substrate thereof may be selected so as to result in a suitable rate of hydrogen peroxide production. The skilled person can determine a suitable rate of hydrogen peroxide based on a desired concentration (e.g., steady state concentration) of hydrogen peroxide (which will depend on an intended use of the composition) and on a rate at which the hydrogen peroxide is consumed, which will depend, for example, on a concentration and reactivity of compounds which react with hydrogen peroxide (e.g., agents such as described herein).

In some embodiments of any of the embodiments described in the context of a hydrogen peroxide-producing composition, a concentration of the hydrogen peroxide-producing enzyme (e.g., glucose oxidase) in the composition is in a range of from 0.125 to 1250 units/gram. In some embodiments, the concentration is in a range of from 1.25 to 125 units/gram. In some embodiments, the concentration is in a range of from 4 to 40 units/gram. In some embodiments, the concentration is in a range of from 6 to 20 units/gram. In some embodiments, the concentration is about 12.5 units/gram.

In some embodiments of any of the embodiments described in the context of a hydrogen peroxide-producing composition, a concentration of the hydrogen peroxide-producing enzyme (e.g., glucose oxidase) in the composition is in a range of from 1.25 to 1250 units/gram. In some embodiments, the concentration is in a range of from 4 to 1250 units/gram. In some embodiments, the concentration is in a range of from 12.5 to 1250 units/gram.

In some embodiments of any of the embodiments described in the context of a hydrogen peroxide-producing composition, a concentration of the hydrogen peroxide-producing enzyme (e.g., glucose oxidase) in the composition is in a range of from 0.125 to 125 units/gram. In some embodiments, the concentration is in a range of from 0.125 to 40 units/gram. In some embodiments, the concentration is in a range of from 0.125 to 12.5 units/gram.

As used herein and in the art, a "unit" of an enzyme refers to an amount of the enzyme which catalyzes a conversion of 1 micromole of a substrate (e.g., a substrate as described herein) per minute, at a temperature of 25° C. and at substrate concentrations which yield a maximal conversion rate.

In some embodiments of any of the embodiments described in the context of a hydrogen peroxide-producing composition, a concentration of the substrate of the hydrogen peroxide-producing enzyme (e.g., glucose) in the composition is in a range of from 0.0175 μmole/gram to 175 μmole/gram. In some embodiment, the concentration is in a range of from 0.175 to 17.5 μmole/gram. In some embodiment, the concentration is in a range of from 0.5 to 6 μmole/gram. In some embodiment, the concentration is in a range of from 1 to 3.5 μmole/gram. In some embodiment, the concentration is about 1.75 μmole/gram.

In some embodiments of any of the embodiments described in the context of a hydrogen peroxide-producing composition, a concentration of the substrate of the hydrogen peroxide-producing enzyme (e.g., glucose) in the composition is in a range of from 0.175 μmole/gram to 175 μmole/gram. In some embodiment, the concentration is in a range of from 0.5 to 175 μmole/gram. In some embodiment, the concentration is in a range of from 1.75 to 175 μmole/gram.

In some embodiments of any of the embodiments described in the context of a hydrogen peroxide-producing composition, a concentration of the substrate of the hydrogen peroxide-producing enzyme (e.g., glucose) in the composition is in a range of from 0.0175 μmole/gram to 17.5

μmole/gram. In some embodiment, the concentration is in a range of from 0.0175 to 6 μmole/gram. In some embodiment, the concentration is in a range of from 0.0175 to 1.75 μmole/gram.

In some embodiments of any of the embodiments described in the context of a hydrogen peroxide-producing composition, a concentration of the hydrogen peroxide-producing enzyme (e.g., glucose oxidase) in the composition is in a range of from 0.125 to 1250 units/gram, and a concentration of the substrate of the hydrogen peroxide-producing enzyme (e.g., glucose) in the composition is in a range of from 0.0175 μmole/gram to 175 μmole/gram. In some embodiments, the enzyme concentration is in a range of from 1.25 to 125 units/gram. In some embodiments, the enzyme concentration is in a range of from 4 to 40 units/gram. In some embodiments, the enzyme concentration is in a range of from 6 to 20 units/gram. In some embodiments, the enzyme concentration is about 12.5 units/gram. In some embodiments, the enzyme is glucose oxidase and the substrate is glucose.

In some embodiments of any of the embodiments described in the context of a hydrogen peroxide-producing composition, a concentration of the hydrogen peroxide-producing enzyme (e.g., glucose oxidase) in the composition is in a range of from 0.125 to 1250 units/gram, and a concentration of the substrate of the hydrogen peroxide-producing enzyme (e.g., glucose) in the composition is in a range of from 0.175 μmole/gram to 175 μmole/gram. In some embodiments, the enzyme concentration is in a range of from 1.25 to 125 units/gram. In some embodiments, the enzyme concentration is in a range of from 4 to 40 units/gram. In some embodiments, the enzyme concentration is in a range of from 6 to 20 units/gram. In some embodiments, the enzyme concentration is about 12.5 units/gram. In some embodiments, the enzyme is glucose oxidase and the substrate is glucose.

In some embodiments of any of the embodiments described in the context of a hydrogen peroxide-producing composition, a concentration of the hydrogen peroxide-producing enzyme (e.g., glucose oxidase) in the composition is in a range of from 0.125 to 1250 units/gram, and a concentration of the substrate of the hydrogen peroxide-producing enzyme (e.g., glucose) in the composition is in a range of from 0.0175 μmole/gram to 17.5 μmole/gram. In some embodiments, the enzyme concentration is in a range of from 1.25 to 125 units/gram. In some embodiments, the enzyme concentration is in a range of from 4 to 40 units/gram. In some embodiments, the enzyme concentration is in a range of from 6 to 20 units/gram. In some embodiments, the enzyme concentration is about 12.5 units/gram. In some embodiments, the enzyme is glucose oxidase and the substrate is glucose.

In some embodiments of any of the embodiments described in the context of a hydrogen peroxide-producing composition, a concentration of the hydrogen peroxide-producing enzyme (e.g., glucose oxidase) in the composition is in a range of from 0.125 to 1250 units/gram, and a concentration of the substrate of the hydrogen peroxide-producing enzyme (e.g., glucose) in the composition is in a range of from 0.175 μmole/gram to 17.5 μmole/gram. In some embodiments, the enzyme concentration is in a range of from 1.25 to 125 units/gram. In some embodiments, the enzyme concentration is in a range of from 4 to 40 units/gram. In some embodiments, the enzyme concentration is in a range of from 6 to 20 units/gram. In some embodiments, the enzyme concentration is about 12.5 units/gram. In some embodiments, the enzyme is glucose oxidase and the substrate is glucose.

In some embodiments of any of the embodiments described in the context of a hydrogen peroxide-producing composition, a concentration of the hydrogen peroxide-producing enzyme (e.g., glucose oxidase) in the composition is in a range of from 0.125 to 1250 units/gram, and a concentration of the substrate of the hydrogen peroxide-producing enzyme (e.g., glucose) in the composition is in a range of from 0.5 to 175 μmole/gram. In some embodiments, the enzyme concentration is in a range of from 1.25 to 125 units/gram. In some embodiments, the enzyme concentration is in a range of from 4 to 40 units/gram. In some embodiments, the enzyme concentration is in a range of from 6 to 20 units/gram. In some embodiments, the enzyme concentration is about 12.5 units/gram. In some embodiments, the enzyme is glucose oxidase and the substrate is glucose.

In some embodiments of any of the embodiments described in the context of a hydrogen peroxide-producing composition, a concentration of the hydrogen peroxide-producing enzyme (e.g., glucose oxidase) in the composition is in a range of from 0.125 to 1250 units/gram, and a concentration of the substrate of the hydrogen peroxide-producing enzyme (e.g., glucose) in the composition is in a range of from 0.0175 to 6 μmole/gram. In some embodiments, the enzyme concentration is in a range of from 1.25 to 125 units/gram. In some embodiments, the enzyme concentration is in a range of from 4 to 40 units/gram. In some embodiments, the enzyme concentration is in a range of from 6 to 20 units/gram. In some embodiments, the enzyme concentration is about 12.5 units/gram. In some embodiments, the enzyme is glucose oxidase and the substrate is glucose.

In some embodiments of any of the embodiments described in the context of a hydrogen peroxide-producing composition, a concentration of the hydrogen peroxide-producing enzyme (e.g., glucose oxidase) in the composition is in a range of from 0.125 to 1250 units/gram, and a concentration of the substrate of the hydrogen peroxide-producing enzyme (e.g., glucose) in the composition is in a range of from 0.5 to 6 μmole/gram. In some embodiments, the enzyme concentration is in a range of from 1.25 to 125 units/gram. In some embodiments, the enzyme concentration is in a range of from 4 to 40 units/gram. In some embodiments, the enzyme concentration is in a range of from 6 to 20 units/gram. In some embodiments, the enzyme concentration is about 12.5 units/gram. In some embodiments, the enzyme is glucose oxidase and the substrate is glucose.

In some embodiments of any of the embodiments described in the context of a hydrogen peroxide-producing composition, a concentration of the hydrogen peroxide-producing enzyme (e.g., glucose oxidase) in the composition is in a range of from 0.125 to 1250 units/gram, and a concentration of the substrate of the hydrogen peroxide-producing enzyme (e.g., glucose) in the composition is in a range of from 1.75 to 175 μmole/gram. In some embodiments, the enzyme concentration is in a range of from 1.25 to 125 units/gram. In some embodiments, the enzyme concentration is in a range of from 4 to 40 units/gram. In some embodiments, the enzyme concentration is in a range of from 6 to 20 units/gram. In some embodiments, the enzyme concentration is about 12.5 units/gram. In some embodiments, the enzyme is glucose oxidase and the substrate is glucose.

In some embodiments of any of the embodiments described in the context of a hydrogen peroxide-producing composition, a concentration of the hydrogen peroxide-producing enzyme (e.g., glucose oxidase) in the composition is in a range of from 0.125 to 1250 units/gram, and a concentration of the substrate of the hydrogen peroxide-producing enzyme (e.g., glucose) in the composition is in a range of from 0.0175 to 1.75 µmole/gram. In some embodiments, the enzyme concentration is in a range of from 1.25 to 125 units/gram. In some embodiments, the enzyme concentration is in a range of from 4 to 40 units/gram. In some embodiments, the enzyme concentration is in a range of from 6 to 20 units/gram. In some embodiments, the enzyme concentration is about 12.5 units/gram. In some embodiments, the enzyme is glucose oxidase and the substrate is glucose.

In some embodiments of any of the embodiments described in the context of a hydrogen peroxide-producing composition, a concentration of the hydrogen peroxide-producing enzyme (e.g., glucose oxidase) in the composition is in a range of from 0.125 to 1250 units/gram, and a concentration of the substrate of the hydrogen peroxide-producing enzyme (e.g., glucose) in the composition is in a range of from 1 to 3.5 µmole/gram. In some embodiments, the enzyme concentration is in a range of from 1.25 to 125 units/gram. In some embodiments, the enzyme concentration is in a range of from 4 to 40 units/gram. In some embodiments, the enzyme concentration is in a range of from 6 to 20 units/gram. In some embodiments, the enzyme concentration is about 12.5 units/gram. In some embodiments, the enzyme is glucose oxidase and the substrate is glucose.

It is to be noted that for any one of the embodiments pertaining to a composition as described herein, any one of the hydrogen peroxide producing enzymes, including any of the embodiments described herein with respect thereto, in any combination, can be utilized (unless other indicated).

In some embodiments of any of the embodiments and any of the aspects described herein, the composition is for obtaining hydrogen peroxide per se as an active agent. The hydrogen peroxide may be intended, for example, for lightening a topical bodily site of a subject (e.g., a region of the skin, hair and/or nail of a subject) by direct reaction (e.g., bleaching) with the topical bodily site, for exhibiting an anti-microbial activity, or for exhibiting an odor removal activity (e.g., removal of skunk odor).

In some embodiments of any of the embodiments and any of the aspects described herein, the composition further comprises at least one agent which exhibits a cosmetic or pharmaceutical activity in a presence of hydrogen peroxide. In some embodiment, the composition is for obtaining the activity of such an agent, by generating hydrogen peroxide in a presence of the agent.

Herein, "an agent that exhibits a cosmetic or pharmaceutical activity in the presence of hydrogen peroxide" encompasses agents that are activated in the presence of hydrogen peroxide. By "activated" it is meant that the agent is chemically modified (e.g., oxidized) in the presence of hydrogen peroxide and its oxidized form exhibits a desired cosmetic or pharmaceutical activity; or the agent is an enzyme which requires hydrogen peroxide for exhibiting its activity (e.g., requires hydrogen peroxide as a substrate or as a co-activator).

Non-limiting examples of agents which exhibit a cosmetic or pharmaceutical activity in a presence of hydrogen peroxide include, for example, peroxidases and oxidative dye precursors.

Oxidative dye precursors are compounds which react to form a colorant (e.g., a permanent dye) upon oxidation, for example, for use in coloring hair. Hydrogen peroxide is commonly used for oxidizing such dye precursors, and many suitable oxidative dye precursors and their precise uses will be known to the skilled person. In some embodiments of any of the embodiments described herein, the composition comprises at least one oxidative dye precursor for coloring hair.

Peroxidases are enzymes which catalyze a formation of a reactive compound, such as a reactive oxygen species (ROS), in a presence of hydrogen peroxide. A peroxidase thereby enhances a reactivity of the hydrogen peroxide, by converting it to a more reactive compound. Such a composition may be useful, for example, for lightening a topical bodily site by reaction of the reactive compound with the bodily site, for exhibiting an anti-microbial activity, or for exhibiting an enhanced odor removal activity (e.g., removal of skunk odor).

In some embodiments of any of the embodiments described herein, a peroxidase oxidizes thiocyanate to hypothiocyanate and/or at least one halide (e.g., chloride, bromide and/or iodide) to a hypohalite (e.g., hypochlorite, hypobromite and/or hypoiodite). Examples of such peroxidases include, without limitation, myeloperoxidase and eosinophil peroxidase (which can each oxidize, for example, thiocyanate, chloride, bromide and iodide), lactoperoxidase (which can oxidize, for example, thiocyanate, bromide and iodide), ovoperoxidase and vanadium bromoperoxidase (which can each oxidize, for example, bromide and iodide), Murex bromoperoxidase (which can oxidize, for example, bromide), horseradish peroxidase (which can oxidize, for example, thiocyanate and iodide) and thyroid peroxidase (which can oxidize, for example, iodide).

In some embodiments of any of the embodiments described herein, the composition further comprises a substrate (e.g., thiocyanate, chloride, bromide, iodide, and/or an oxidizing mediator as described herein) which is oxidized in the presence of hydrogen peroxide and the peroxidase.

Herein, the phrase "oxidizing mediator" refers to a molecule which facilitates a redox reaction catalyzed by the peroxidase, for example, by increasing the oxidative potential and/or the stability of a peroxidase, and/or by acting as a co-factor for the peroxidase, and/or by acting as a substrate of the peroxidase which forms a reactive intermediate product (e.g., a free radical). Oxidizing mediators include compounds (e.g., aromatic compounds) capable of stabilizing electrons (e.g., by delocalization) transferred during a reaction catalyzed by the peroxidase.

In some embodiments of any of the embodiments described herein, the peroxidase oxidizes a substrate (e.g., thiocyanate, chloride, bromide, iodide) present in or on the topical bodily site in the presence of hydrogen peroxide.

Other cosmetic or pharmaceutical activities of peroxidases may also be utilized in the context of any of the embodiments of this aspect of the invention.

In some embodiments of any of the embodiments described herein, the peroxidase is capable, in a presence of hydrogen peroxide, of degrading melanin in a subject (e.g., in skin and/or hair). In some embodiments, a presence of an oxidizing mediator is necessary for the peroxidase to degrade melanin in the presence of hydrogen peroxide. Degradation of melanin is useful for lightening skin and/or hair. Lignin peroxidase is an exemplary peroxidase capable of degrading melanin.

Without being bound by any particular theory, it is believed that some peroxidases (e.g., lignin peroxidase)

degrade melanin by oxidizing an oxidizing mediator (which serves as a substrate) so as to form a free radical, and the free radical then reacts so as to degrade melanin.

In some embodiments of any of the embodiments and any of the aspects described herein, the composition is a hair-dye composition. Herein, the phrase "hair-dye composition" refers to any composition used in the coloring (e.g., permanent dyeing) of hair, including compositions which comprise a hair dye and/or precursor thereof and compositions which do not comprise a hair dye or precursor thereof, but which are intended to be contacted with a hair dye and/or precursor thereof (e.g., on the hair).

In some embodiments of any of the embodiments and any of the aspects described herein, the composition is an odor-removal composition, for example, for removal of skunk odor (e.g., from skin, hair and/or nail). In some embodiments, the odor-removal composition further comprises a detergent (e.g., sodium lauryl sulfate) and/or an alkaline agent (e.g., sodium bicarbonate).

In some embodiment of any of the embodiments and any of the aspects described herein, the composition is an anti-microbial composition. Herein, the phrase "anti-microbial composition" refers to any composition for killing or otherwise inhibiting microscopic animals, plants, fungi, bacteria, archaebacteria and/or viruses.

In some embodiments of any of the embodiments and any of the aspects described herein, the composition is a bleaching composition. Herein, the phrase "bleaching composition" refers to any composition for removing at least a portion of a color, and includes, for example, compositions for lightening skin and/or portions of skin, hair bleaching compositions, and compositions for removing stains from nails.

As exemplified herein, lignin peroxidase is capable of degrading melanin, thereby lightening skin and/or hair.

Lignin peroxidase is an exemplary agent which exhibits a cosmetic activity in a presence of hydrogen peroxide.

In some embodiments, lignin peroxidase is utilized in combination with any one of the embodiments described herein for a composition and/or hydrogen peroxide producing enzyme, and any combination thereof.

In some embodiments of any of the embodiments described herein, the skin to be lightened comprises facial skin (e.g., forehead and/or cheeks).

In some embodiments of any of the embodiments described herein, the skin to be lightened comprises a skin region exposed to the sun (e.g., a tanned region).

In some embodiments of any of the embodiments described herein, lightening skin comprises lightening a whole skin complexion.

In some embodiments of any of the embodiments described herein, the skin to be lightened comprises a relatively dark portion of skin, for example, skin comprising an uneven tone, one or more dark spots, one or more freckles, melasma, hyperpigmentation of skin, skin discoloration, one or more age spots, one or more acne marks and/or a scar.

As described herein, a desired concentration of hydrogen peroxide may be determined by selecting suitable concentrations of hydrogen peroxide-producing enzyme and the substrate thereof and compounds which react with hydrogen peroxide (if any described herein).

In some embodiments of any of the embodiments described herein, a composition for obtaining hydrogen peroxide per se (e.g., a bleaching composition) has concentrations of ingredients selected so as to result in a relatively high hydrogen peroxide concentration, for example, from 0.5 to 12 weight percents. In some embodiments, the hydrogen peroxide concentration is no more than 6 weight percents. In some embodiments, the hydrogen peroxide concentration is no more than 3 weight percents. A relatively high hydrogen peroxide concentration may be obtained, for example, by minimizing a presence of compounds which react with hydrogen peroxide and/or by selecting higher concentration of the component of the enzymatic system, as described herein.

In some embodiments of any of the embodiments described herein, a composition comprising an agent exhibiting an activity in a presence of hydrogen peroxide (e.g., as described herein) has concentrations of ingredients selected so as to result in a hydrogen peroxide concentration suitable for obtaining the activity of the agent. In some embodiments, the hydrogen peroxide concentration is relatively low, for example, no more than 0.5 weight percents. In some embodiments, the hydrogen peroxide concentration is no more than 0.1 weight percents. In some embodiments, the hydrogen peroxide concentration is no more than 0.02 weight percents. It is to be appreciated that the agent may help to maintaining a relatively low hydrogen peroxide concentration by reacting with the hydrogen peroxide. The agent may continuously react with the generated hydrogen peroxide such that a low concentration of hydrogen peroxide is continuously maintained.

Low concentration of hydrogen peroxide may be especially advantageous, for example, in a composition comprises an agent (e.g., a protein such as a peroxidase) which may be sensitive to (e.g., adversely affected by) high peroxide concentrations and/or which may be highly efficient at reacting with hydrogen peroxide. Such agents which may be adversely affected by high hydrogen peroxide concentrations include, for example, certain peroxidases (e.g., lignin peroxidase), which are known for, for example, undergoing "self-suicidality" in the presence of high concentrations of hydrogen peroxide.

Kits for Obtaining the Hydrogen Peroxide Producing Composition:

It is to be understood that a hydrogen peroxide-producing composition according to any one of the embodiments relating to such compositions may be obtained using a kit according to any one of the embodiments described herein relating to such kits (e.g., as described in this section). The skilled person will be capable of selecting a suitable kit as described herein so as to obtain any desired composition described herein, based on the guidance provided herein.

For any one of the embodiments describing a kit, any one of the hydrogen peroxide-producing enzymes and/or compositions, including any one of the respective embodiments thereof, and any combination thereof, can be utilized.

In some embodiments of any of the embodiments described herein, any of the compositions as described herein can be considered as a two (or more)-part composition, in which one part of the composition comprises a hydrogen peroxide-producing enzyme as described herein and one part of the composition comprises a substrate of the enzyme.

In some embodiments of any of the embodiments described herein, the two-part composition is packaged in a kit and is identified for use in any cosmetic or pharmaceutical application that utilizes hydrogen peroxide, either per se, or in combination with another agent, as described herein.

According to an aspect of some embodiments of the invention, there is provided a kit for forming and/or applying (topically) to a topical bodily site of a subject a cosmetic or pharmaceutical composition, as described herein, wherein the cosmetic or pharmaceutical composition comprises hydrogen peroxide (e.g., in accordance with a method described herein).

In some embodiments of any of the embodiments described herein, the composition is packaged in the kit such that all of its components are packaged together in a container, under conditions that inhibit hydrogen peroxide formation, as described herein. In some of these embodiments, once the composition is dispensed from the container and applied on the bodily site, its exposure to air and/or humidity promotes a reaction between the hydrogen peroxide-producing enzyme and its substrate and hydrogen peroxide is produced.

In some embodiments of any of the embodiments described herein, a part of the composition which comprises a hydrogen peroxide-producing enzyme and a part of the composition which comprise the substrate are packaged individually within the kit, such that the composition is formed once these two parts of the composition are mixed.

By "packaged individually" it is meant that the there is no direct contact between the parts of the composition (or the first and second compositions as described herein) when in the kit.

For example, each part of the composition (e.g., a first composition and a second composition, as described herein) is individually packaged within a sealed container in the kit. The container can be made of e.g., plastic, wood, nylon, glass, fabric, metal, leather and/or metal foil.

One or more of the containers may include means for dispensing its content, either directly to the topical bodily site or to a receptacle for mixing with other parts of the composition which are packaged individually within the kit. Alternatively, the kit further comprises means for dispensing the contents of one or more of the containers, and/or means for mixing the contents of the container and means for dispensing the obtained mixture on the topical bodily site.

In some embodiments of any of the embodiments described herein, the kit comprises a first composition comprising a hydrogen peroxide-producing enzyme (e.g., as described herein) and a second composition comprising a substrate of the hydrogen peroxide-producing enzyme (e.g., as described herein). In some embodiments, the first and second compositions of the kit are packaged individually in the kit. The first composition and second composition of the kit may be combined so as to prepare the cosmetic or pharmaceutical composition (e.g., a composition described herein) in which the enzyme contacts the substrate, thereby producing hydrogen peroxide in the composition.

In some embodiments of any of the embodiments described herein, the kit further comprises at least one agent which exhibits a cosmetic or pharmaceutical activity in a presence of hydrogen peroxide (e.g., as described herein). The agent(s) may be included within the first composition, the second composition and/or in a third composition within the kit, which is individually packaged in the kit. The first composition and second composition and optional third composition of the kit may be combined so as to prepare the cosmetic or pharmaceutical composition comprising the agent(s) (e.g., as described herein).

Combining the first and second compositions of the kit can be effected immediately before application to the topical bodily site (e.g., between 1 minute and 10 minutes before application), or during application to the topical bodily site.

Minimizing a time interval between combination of the compositions may be advantageous in avoiding a situation in which hydrogen peroxide is being produced in the presence of an agent, such as a peroxidase or an oxidative dye precursor, which reacts with the hydrogen peroxide (e.g., as described herein) when the composition is not in contact with the topical body site, as such a situation could result in non-productive consumption (e.g., a waste) of the hydrogen peroxide.

Combining the first and second compositions of the kit during application can be effected, for example, by co-administering the first and second compositions of the kit to the topical bodily site.

By "co-administering" it is meant that the first and second compositions are topically administered to the bodily site at the same time (concomitantly) or, that the first and second compositions of the kit are administered sequentially, in any order, whereby the time interval between administration of the first composition and administration of the second composition may range from 0.1 minute to 5 minute. In some embodiments, the time interval is no more than 2 minutes.

If a third composition is included in the kit, it can be combined with the first and second composition before application to the bodily site, or be co-administered to the bodily site with the first and second compositions.

The third composition can be co-administered concomitantly with the first and/or second composition, before administration of the first and/or second composition, or thereafter, with the time interval between administrations is as described hereinabove.

In some embodiments of any of the embodiments described herein, the kit further comprises written instructions for how to use a composition(s) therein, for example, an amount of a composition to be applied, a sequence in which different compositions are to be applied, a timing and/or frequency of applications, and/or a duration of treatment (e.g., as described herein).

In some embodiments of any of the embodiments described herein, the kit further comprises a wash composition, such as a facial wash, for cleaning a topical body site prior to contact with a composition described herein.

According to exemplary embodiments, the facial wash comprises ingredients as presented in Table 1:

TABLE 1

| Facial wash according to exemplary embodiments | |
|---|---|
| Ingredient | Weight percentage range |
| Water | 25-50% |
| Propanediol | 10-25% |
| Glycerin | 10-25% |
| Stearic acid | 10-25% |
| Myristic acid | 5-10% |
| Potassium hydroxide | 5-10% |
| Lauric acid | 1-5% |
| Decyl glucoside | 1-5% |
| Glycol distearate | 1-5% |
| Glyceryl stearate | 1-5% |
| PEG-100 stearate | 1-5% |
| Synthetic beeswax | 1-5% |
| Potassium cocoyl glycinate | 0-0.1% |
| Butylated hydroxytoluene (BHT) | 0-0.1% |
| Lignin peroxidase | 0-0.1% |

In some embodiments of any of the embodiments described herein, the kit includes appropriate instructions for use and labels indicating approval by a regulatory agency for the indicated use, as described herein.

Cosmetic Applications of a Hydrogen Peroxide Producing Composition:

As exemplified herein, by providing a hydrogen peroxide-producing enzyme in contact with its substrate, the compositions described herein are effective at administering hydrogen peroxide to a surface.

According to an aspect of embodiments of the invention, there is provided a method of topically administering hydrogen peroxide to a topical bodily site of a subject (e.g., to skin, hair and/or nail of a subject). The method, according to some of these embodiments, is effected by contacting a topical bodily site, or a region thereof, of the subject with a composition (e.g., a composition described herein) comprising a hydrogen peroxide-producing enzyme and a substrate of the hydrogen peroxide-producing enzyme. In some embodiments, the composition is formed by a hydrogen peroxide-producing enzyme and a substrate thereof as packaged within a kit as described herein.

It is to be understood that a method of topically administering hydrogen peroxide according to any one of the embodiments relating to such a method (e.g., as described in this section) may utilize a hydrogen peroxide-producing system and/or a kit according to any one of the embodiments described herein relating to such systems and/or kits.

As used herein the terms "topical" and "topically" refer to a topical body site, as defined herein, including, for example, to administration of a composition by application onto a topical body site, and to compositions for administration in such a manner.

Herein, the phrase "topical body site" or "topical bodily site" refers to a skin surface (including any particular region of the skin surface), and/or hair (including all hair and/or any particular region of hair) from any part of the body, and/or a nail surface (including all fingernails and/or toenails, and/or any individual nail and/or a region thereof). The skin may be of any part of a body, for example, facial skin, neck skin, arm skin, hand skin, torso skin and/or leg skin. The hair may be, for example, head hair, facial hair and/or pubic hair. This phrase encompasses also a certain region or part of a skin surface (e.g., a part of a facial skin, a part of an arm or leg skin), or of a hair (e.g., a part of facial, head or pubic hair), as described in further detail elsewhere herein.

In some embodiments of any of the embodiments described herein, the skin of a topical body site does not include mucous membranes such as those of the mouth, lips, eyelids, ears, genital area and anus.

In some embodiments of any of the embodiments described herein, the composition is formed by contacting the topical bodily site or a region thereof with the hydrogen peroxide-producing enzyme and/or the substrate thereof subsequent to contacting the topical bodily site or a region thereof with the agent which exhibits a cosmetic or pharmaceutical activity in a presence of hydrogen peroxide. In such a sequence, hydrogen peroxide will only be generated in a presence of the agent which exhibits a cosmetic or pharmaceutical activity in a presence of hydrogen peroxide, which may allow for a more efficient utilization of the hydrogen peroxide.

In some embodiments of any of the embodiments described herein, the composition is formed by contacting the topical body site with the hydrogen peroxide-producing enzyme before contacting the topical body site with the substrate.

In some embodiments of any of the embodiments described herein, the composition is formed by contacting the topical body site with the hydrogen peroxide-producing enzyme after contacting the topical body site with the substrate.

In some embodiments of any of the embodiments described herein, the composition is formed by contacting the topical body site with the hydrogen peroxide-producing enzyme concomitantly with contacting the topical body site with the substrate.

The agent which exhibits a cosmetic or pharmaceutical activity in a presence of hydrogen peroxide may be contacted with the topical body site (or region thereof) before, after or concomitantly with contacting the topical region with any of the other components, for example, by co-administering (as defined herein) the agent with the hydrogen peroxide-producing enzyme and/or the substrate thereof.

In some embodiments of any of the embodiments described herein, the method is for coloring hair, and the method further comprising contacting the hair with at least one oxidative dye precursor for coloring hair, as described herein.

In some embodiments of any of the embodiments described herein, the method further comprises contacting the topical body site with a peroxidase (e.g., as described herein). Such a method, may be useful, for example, for lightening a topical bodily site, for exhibiting an anti-microbial activity, or for exhibiting an enhanced odor removal activity (e.g., as described herein).

In some embodiments of any of the embodiments described herein, the method further comprises contacting the topical body site with a substrate and/or oxidizing mediator of the peroxidase (e.g., as described herein).

In some embodiments of any of the embodiments described herein, the method is for removal of skunk odor (e.g., from a topical body site). In some embodiments, the method further comprises contacting the topical body site with a detergent (e.g., sodium lauryl sulfate) and/or an alkaline agent (e.g., sodium bicarbonate).

In some embodiments of any of the embodiments described herein, the method is for obtaining an anti-microbial activity, for example, by forming an anti-microbial composition (e.g., as described herein).

In some embodiments of any of the embodiments described herein, the method is for bleaching a topical body site or a region thereof, for example, by forming a bleaching composition (e.g., as described herein). The method may comprise, for example, lightening skin and/or portions of skin, bleaching hair, and/or removing stains from nails.

In some embodiments of any of the embodiments described herein, the method is for lightening facial skin (e.g., forehead and/or cheeks).

In some embodiments of any of the embodiments described herein, the method is for lightening a skin region exposed to the sun (e.g., a tanned region).

In some embodiments of any of the embodiments described herein, the method is for lightening a whole skin complexion.

In some embodiments of any of the embodiments described herein, the method is for lightening a relatively dark portion of skin, for example, skin comprising an uneven tone, one or more dark spots, one or more freckles, melasma, hyperpigmentation of skin, skin discoloration, one or more age spots, one or more acne marks and/or a scar.

In some embodiments of any of the embodiments described herein, the method is effected repeatedly, optionally even indefinitely, in order to respond to repeated color formation, such as newly formed melanin in skin, new growth of dark hair, chronic stain formation in nails, and so forth.

In some embodiments of any of the embodiments described herein, the method is effected by contacting the topical region with the composition at least 5 times. In some embodiments, the method is effected by contacting the topical region with the composition at least 10 times. In some embodiments, the method is effected by contacting the topical region with the composition at least 20 times. In some embodiments, the method is effected by contacting the topical region with the composition at least 50 times. In some embodiments, the method is effected by contacting the topical region with the composition at least 100 times. In some embodiments, the method is effected by contacting the topical region with the composition at least 200 times.

In some embodiments of any of the embodiments described herein, the method is effected by contacting the topical region once or twice per day. In exemplary embodiments, contacting is effected twice per day.

In some embodiments of any of the embodiments described herein, the method is effected for at least one week. In some embodiments, the method is effected for at least two weeks. In some embodiments, the method is effected for at least three weeks. In some embodiments, the method is effected for at least four weeks. In some embodiments, the method is effected for at least six weeks. In some embodiments, the method is effected for at least eight weeks. In some embodiments, the method is effected for at least three months. In some embodiments, the method is effected for at least four months. In some embodiments, the method is effected for at least six months. In some embodiments, the method is effected for at least one year.

The dosing and course of treatment will depend on the type of treatment and the severity of an affliction being treated, with course of treatment lasting from one day to several weeks or longer, or until cure is effected or diminution of the condition being treated is achieved.

The amount of a composition to be administered will, of course, be dependent on the subject being treated, the degree of a condition being treated, the manner of administration, the judgment of a prescribing physician or a cosmetician or the consumer, the desired effect of the composition, etc.

In some embodiments of any of the embodiments described herein, the topical body site is cleaned (e.g., with a wash, as described herein) prior to contact with a composition described herein.

In embodiments where the method is, for example, for bleaching or coloring hair, the method can be effected once, for achieving a desired effect and can be repeated once the desired effect is reduced or diminished.

In embodiments where the method is, for example, for treating an infection, the treatment is effected once, until the infection is eliminated, and the number of administrations and treatment duration is effected until cure is effected.

Hydrogen Peroxide Producing Compositions, Methods and Kits for Lightening Skin and/or Hair:

An exemplary embodiment of the compositions, methods and kits described herein is a composition for lightening a topical body site such as skin and/or hair in which a hydrogen peroxide-producing composition as described herein is used in combination with lignin peroxidase.

It is to be understood that a composition, method and/or kit according to any one of the embodiments relating to such compositions, methods and/or kits may be utilized for lightening kin and/or hair, as described herein (e.g., in this section).

In some embodiments of any of the embodiments described herein, there is provided a cosmetic composition for lightening a topical body site such as skin and/or hair of a subject (e.g., as described herein), the composition comprising a lignin peroxidase, a hydrogen peroxide-producing enzyme (e.g., as described herein) and a substrate of the hydrogen peroxide-producing enzyme (e.g., as described herein).

According to another aspect of embodiments described herein, there is provided a cosmetic method of lightening a topical body site such as skin and/or hair of a subject (e.g., as described herein), the method comprising contacting a topical region of a subject with a composition comprising a lignin peroxidase, a hydrogen peroxide-producing enzyme and a substrate of the hydrogen peroxide-producing enzyme (e.g., a lignin peroxidase-containing composition described herein). In some embodiments, the composition is formed by a lignin peroxidase, a hydrogen peroxide-producing enzyme and a substrate thereof as packaged within a kit described herein.

In some embodiments of any of the embodiments described herein, the composition is formed by contacting the topical region with the hydrogen peroxide-producing enzyme and/or the substrate thereof subsequent to contacting the topical region with the lignin peroxidase. In such a sequence, hydrogen peroxide will only be generated in a presence of the lignin peroxidase, which may allow for a more efficient utilization of the hydrogen peroxide.

Compositions comprising lignin peroxidase, as described herein, can be provided at higher concentrations and be prescribed by a physician as a pharmaceutical or a cosmetic composition to treat skin pigmentation disorders such as melasma, chloasma, ochronosis, and lentigo, and/or to lighten whole skin complexion.

In some embodiments of any of the embodiments described herein, the method is effected by contacting the topical region with the composition at least 5 times. In some embodiments, the method is effected by contacting the topical region with the composition at least 10 times. In some embodiments, the method is effected by contacting the topical region with the composition at least 20 times. In some embodiments, the method is effected by contacting the topical region with the composition at least 50 times. In some embodiments, the method is effected by contacting the topical region with the composition at least 100 times. In some embodiments, the method is effected by contacting the topical region with the composition at least 100 times.

In some embodiments of any of the embodiments described herein, the method is effected by contacting the topical region once or twice per day. In exemplary embodiments, contacting is effected twice per day.

In some embodiments of any of the embodiments described herein, the method is effected for at least one week. In some embodiments, the method is effected for at least two weeks. In some embodiments, the method is effected for at least three weeks. In some embodiments, the method is effected for at least four weeks. In some embodiments, the method is effected for at least six weeks. In some embodiments, the method is effected for at least eight weeks. In some embodiments, the method is effected for at least three months. In some embodiments, the method is effected for at least four months. In some embodiments, the method is effected for at least six months. In some embodiments, the method is effected for at least one year.

The dosing and course of treatment will depend on the degree of color (e.g., pigmentation) in the region to be treated, for example, a degree of skin pigmentation in a skin pigmentation disorder (e.g., chloasma, melasma, ochronosis and lentigo), the tone of skin color, skin complexion and/or the responsiveness of the skin, with course of treatment lasting from several days to several weeks or longer, or until cure is effected or diminution of the skin disorder is achieved.

The amount of a composition to be administered will, of course, be dependent on the subject being treated, the degree of a condition being treated, the manner of administration, the judgment of a prescribing physician or a cosmetician or the consumer, etc.

Lignin Peroxidase:

It is to be understood that lignin peroxidase according to any one of the embodiments described herein relating to lignin peroxidase (e.g., as described in this section) may be used in combination with a hydrogen peroxide-producing enzymatic system according to any one of the embodiments described herein relating to such a system.

As used herein the phrase "lignin peroxidase" refers to an enzyme which plays a major role in lignin degradation. Lignin peroxidase is able to catalyze the oxidation of substrates with high redox potential. This unique ability is consistent with a heme active site of low electron density, which is indicated by high redox potential [Cai and Tien, *J Biotechnol* 1993, 30: 79-90].

Examples of lignin peroxidases are classified as EC 1.11.1.14.

Manganese peroxidase (EC 1.11.1.13) is involved in degradation of lignin in Basidomycetes (e.g., *Phanerochaete chrysosporium*), and is also defined herein as a lignin degrading peroxidase.

Lignin peroxidase is produced in various organisms and the coding sequences of the lignin peroxidase enzymes are available from GenBank via the Hypertext Transfer Protocol://World Wide Web (dot) ncbi (dot) nlm (dot) nih (dot) gov/. For example, lignin peroxidase from *Phanerochaete chrysosporium* (SEQ ID NO:1); *Mycobacterium tuberculosis* H37Rv [GenBank Accession No. NP_216416.1 (SEQ ID NO:2 (polypeptide) and SEQ ID NO:3 (polynucleotide)]; *Mycobacterium bovis* AF2122/97 [GenBank Accession No. NP_855586.1 (SEQ ID NO:4 (polypeptide) and SEQ ID NO:5 (polynucleotide)]; *Mycobacterium bovis* BCG str. Pasteur 1173P2 [GenBank Accession No. YP_978029.1 (SEQ ID NO:6 (polypeptide) and SEQ ID NO:7 (polynucleotide)]; *Mycobacterium bovis* BCG str. Tokyo 172 [GenBank Accession No. YP_002644977.1 (SEQ ID NO:8 (polypeptide) and SEQ ID NO:9 (polynucleotide)]; *Mycobacterium tuberculosis* H37Ra [GenBank Accession No. YP_001283231.1 (SEQ ID NO:10 (polypeptide) and SEQ ID NO:11 (polynucleotide)]; *Mycobacterium ulcerans* Agy99 [GenBank Accession No. YP_908214.1 (SEQ ID NO:12 (polypeptide) and SEQ ID NO:13 (polynucleotide)]; *Mycobacterium marinum* M [GenBank Accession No. YP_001848608.1 (SEQ ID NO:14 (polypeptide) and SEQ ID NO:15 (polynucleotide)]; *Mycobacterium tuberculosis* KZN 1435 [GenBank Accession No. YP_003032055.1 (SEQ ID NO:16 (polypeptide) and SEQ ID NO:17 (polynucleotide)]; *Mycobacterium tuberculosis* F11 [GenBank Accession No. YP_001287866.1 (SEQ ID NO:18 (polypeptide) and SEQ ID NO:19 (polynucleotide)]; *P. chrysosporium* ligninase (CKG4) [GenBank Accession No. M18743.1 (SEQ ID NO:20 (polypeptide) and SEQ ID NO:21 (polynucleotide)]; *Phanerochaete chrysosporium* (anamorph: *Sporotrichum pruinosum*) [GenBank Accession No. M80213.1 (SEQ ID NO:22 (polypeptide) and SEQ ID NO:23 (polynucleotide)]; *Phanerochaete sordida* ylpB [GenBank Accession No. AB455007.1 (SEQ ID NO:24 (polypeptide) and SEQ ID NO:25 (polynucleotide)]; *Phanerochaete chrysosporium* (anamorph: *Sporotrichum pruinosum*) [GenBank Accession No. M77508.1 (SEQ ID NO:26 (polypeptide) and SEQ ID NO:27 (polynucleotide)].

In some embodiments of any of the embodiments described herein, the lignin peroxidase is a lignin peroxidase of a white rot fungus, for example, a lignin peroxidase extracted from a white rot fungus or a recombinant protein derived from a white rot fungus lignin peroxidase.

Herein and in the art, the phrase "white rot fungus" refers to fungi capable of breaking down lignin in wood. As such a process often leaves the light-colored cellulose of the wood, such fungi typically cause the attacked wood to assume a lighter color.

Examples of white rot fungi producing a suitable lignin peroxidase include, without limitation, *Phanerochaete* (e.g., *Phanerochaete chrysosporium, Phanerochaete sordida*), *Trametes* (e.g., *Trametes versicolor*) and *Ganoderma*.

According to some embodiments of any of the embodiments of the invention, the lignin peroxidase enzyme used according to some embodiments of the invention is the lignin peroxidase H1 isoform, which exhibits melanin oxidation activities both in vitro and in vivo [WO 2004/052275].

In some embodiments of any of the embodiments described herein, a concentration of lignin peroxidase in the composition is in a range of from 1.25 to 125 units/gram. In some embodiments, the concentration is in a range of from 4 to 40 units/gram. In some embodiments, the concentration is in a range of from 6 to 20 units/gram. In some embodiments, the concentration is about 12.5 units/gram.

In some embodiments of any of the embodiments described herein, a concentration of lignin peroxidase in the composition is in a range of from 4 to 125 units/gram. In some embodiments, the concentration is in a range of from 6 to 125 units/gram. In some embodiments, the concentration is in a range of from 12.5 to 125 units/gram.

In some embodiments of any of the embodiments described herein, a concentration of lignin peroxidase in the composition is in a range of from 1.25 to 40 units/gram. In some embodiments, the concentration is in a range of from 1.25 to 20 units/gram. In some embodiments, the concentration is in a range of from 1.25 to 12.5 units/gram.

In some embodiments of any of the embodiments described herein, a concentration of lignin peroxidase in the composition is in a range of from 1.25 to 125 units/gram, and a concentration of the hydrogen peroxide-producing enzyme in the composition is in a range of from 0.125 to 1250 units/gram. In some embodiments, the lignin peroxidase concentration is in a range of from 1.25 to 40 units/gram. In some embodiments, the lignin peroxidase concentration is in a range of from 4 to 125 units/gram. In some embodiments, the lignin peroxidase concentration is in a range of from 4 to 40 units/gram. In some embodiments, the lignin peroxidase concentration is in a range of from 6 to 20 units/gram. In some embodiments, the lignin peroxidase concentration is about 12.5 units/gram. In some embodiments, the hydrogen peroxide-producing enzyme is glucose oxidase.

In some embodiments of any of the embodiments described herein, a concentration of lignin peroxidase in the composition is in a range of from 1.25 to 125 units/gram, and a concentration of the hydrogen peroxide-producing enzyme in the composition is in a range of from 1.25 to 1250 units/gram. In some embodiments, the lignin peroxidase concentration is in a range of from 1.25 to 40 units/gram. In some embodiments, the lignin peroxidase concentration is in a range of from 4 to 125 units/gram. In some embodiments, the lignin peroxidase concentration is in a range of from 4 to 40 units/gram. In some embodiments, the lignin peroxidase concentration is in a range of from 6 to 20 units/gram. In some embodiments, the lignin peroxidase concentration is about 12.5 units/gram. In some embodiments, the hydrogen peroxide-producing enzyme is glucose oxidase.

In some embodiments of any of the embodiments described herein, a concentration of lignin peroxidase in the composition is in a range of from 1.25 to 125 units/gram, and a concentration of the hydrogen peroxide-producing enzyme in the composition is in a range of from 0.125 to 125 units/gram. In some embodiments, the lignin peroxidase concentration is in a range of from 1.25 to 40 units/gram. In some embodiments, the lignin peroxidase concentration is in a range of from 4 to 125 units/gram. In some embodiments, the lignin peroxidase concentration is in a range of from 4 to 40 units/gram. In some embodiments, the lignin peroxidase concentration is in a range of from 6 to 20 units/gram. In some embodiments, the lignin peroxidase concentration is about 12.5 units/gram. In some embodiments, the hydrogen peroxide-producing enzyme is glucose oxidase.

In some embodiments of any of the embodiments described herein, a concentration of lignin peroxidase in the composition is in a range of from 1.25 to 125 units/gram, and a concentration of the hydrogen peroxide-producing enzyme in the composition is in a range of from 1.25 to 125 units/gram. In some embodiments, the lignin peroxidase concentration is in a range of from 1.25 to 40 units/gram. In some embodiments, the lignin peroxidase concentration is in a range of from 4 to 125 units/gram. In some embodiments, the lignin peroxidase concentration is in a range of from 4 to 40 units/gram. In some embodiments, the lignin peroxidase concentration is in a range of from 6 to 20 units/gram. In some embodiments, the lignin peroxidase concentration is about 12.5 units/gram. In some embodiments, the hydrogen peroxide-producing enzyme is glucose oxidase.

In some embodiments of any of the embodiments described herein, a concentration of lignin peroxidase in the composition is in a range of from 1.25 to 125 units/gram, and a concentration of the hydrogen peroxide-producing enzyme in the composition is in a range of from 4 to 1250 units/gram. In some embodiments, the lignin peroxidase concentration is in a range of from 1.25 to 40 units/gram. In some embodiments, the lignin peroxidase concentration is in a range of from 4 to 125 units/gram. In some embodiments, the lignin peroxidase concentration is in a range of from 4 to 40 units/gram. In some embodiments, the lignin peroxidase concentration is in a range of from 6 to 20 units/gram. In some embodiments, the lignin peroxidase concentration is about 12.5 units/gram. In some embodiments, the hydrogen peroxide-producing enzyme is glucose oxidase.

In some embodiments of any of the embodiments described herein, a concentration of lignin peroxidase in the composition is in a range of from 1.25 to 125 units/gram, and a concentration of the hydrogen peroxide-producing enzyme in the composition is in a range of from 0.125 to 40 units/gram. In some embodiments, the lignin peroxidase concentration is in a range of from 1.25 to 40 units/gram. In some embodiments, the lignin peroxidase concentration is in a range of from 4 to 125 units/gram. In some embodiments, the lignin peroxidase concentration is in a range of from 4 to 40 units/gram. In some embodiments, the lignin peroxidase concentration is in a range of from 6 to 20 units/gram. In some embodiments, the lignin peroxidase concentration is about 12.5 units/gram. In some embodiments, the hydrogen peroxide-producing enzyme is glucose oxidase.

In some embodiments of any of the embodiments described herein, a concentration of lignin peroxidase in the composition is in a range of from 1.25 to 125 units/gram, and a concentration of the hydrogen peroxide-producing enzyme in the composition is in a range of from 4 to 40 units/gram. In some embodiments, the lignin peroxidase concentration is in a range of from 1.25 to 40 units/gram. In some embodiments, the lignin peroxidase concentration is in a range of from 4 to 125 units/gram. In some embodiments, the lignin peroxidase concentration is in a range of from 4 to 40 units/gram. In some embodiments, the lignin peroxidase concentration is in a range of from 6 to 20 units/gram. In some embodiments, the lignin peroxidase concentration is about 12.5 units/gram. In some embodiments, the hydrogen peroxide-producing enzyme is glucose oxidase.

According to some embodiments of any of the embodiments described herein, lignin peroxidase is used in combination with an oxidizing mediator. In some embodiments of any of the embodiments described herein, a composition comprising lignin peroxidase further comprises an oxidizing mediator (as defined herein).

Oxidizing mediators for lignin peroxidase include aromatic molecules, such as methoxylated aromatic compounds.

Examples of suitable oxidizing mediators include, without limitation, phenolic compounds such as veratryl alcohol (3,4-dimethoxybenzyl alcohol), veratrole (1,2-dimethoxybenzene) and 1,4-dimethoxybenzene. Veratryl alcohol is an exemplary oxidizing mediator.

In some embodiments of any of the embodiments described herein, a concentration of the oxidizing mediator in the composition is in a range of from 0.03 µmole/gram to 300 µmole/gram. In some embodiments, the concentration is in a range of from 0.3 to 30 µmole/gram. In some embodiments, the concentration is in a range of from 1 to 10 µmole/gram. In some embodiments, the concentration is in a range of from 2 to 5 µmole/gram. In some embodiments, the concentration is about 3 µmole/gram.

In some embodiments of any of the embodiments described herein, a concentration of the oxidizing mediator is in a range of from 0.3 µmole/gram to 300 µmole/gram. In some embodiments, the concentration is in a range of from 1 to 300 µmole/gram. In some embodiments, the concentration is in a range of from 3 to 300 µmole/gram.

In some embodiments of any of the embodiments described herein, a concentration of the oxidizing mediator is in a range of from 0.03 µmole/gram to 30 µmole/gram. In some embodiments, the concentration is in a range of from 0.03 to 10 µmole/gram. In some embodiments, the concentration is in a range of from 0.03 to 3 µmole/gram.

In some embodiments of any of the embodiments described herein, a concentration of the oxidizing mediator in the composition is in a range of from 0.03 µmole/gram to 300 µmole/gram, and a concentration of lignin peroxidase in the composition is in a range of from 1.25 to 125 units/gram. In some embodiments, the oxidizing mediator concentration is in a range of from 0.03 to 30 µmole/gram. In some embodiments, the oxidizing mediator concentration is in a range of from 0.3 to 300 µmole/gram. In some embodiments, the oxidizing mediator concentration is in a range of from 0.3 to 30 µmole/gram. In some embodiments, the oxidizing mediator concentration is in a range of from 1 to 10 µmole/gram. In some embodiments, the oxidizing mediator concentration is in a range of from 2 to 5 µmole/gram. In some embodiments, the oxidizing mediator concentration is about 3 µmole/gram. In some embodiments, the oxidizing mediator is selected from the group consisting of veratryl alcohol, veratrole and 1,4-dimethoxybenzene. In some embodiments, the oxidizing mediator is veratryl alcohol.

In some embodiments of any of the embodiments described herein, a concentration of the oxidizing mediator in the composition is in a range of from 0.03 µmole/gram to 300 µmole/gram, and a concentration of lignin peroxidase in the composition is in a range of from 4 to 125 units/gram. In some embodiments, the oxidizing mediator concentration is in a range of from 0.03 to 30 µmole/gram. In some embodiments, the oxidizing mediator concentration is in a range of from 0.3 to 300 µmole/gram. In some embodiments, the oxidizing mediator concentration is in a range of from 0.3 to 30 µmole/gram. In some embodiments, the oxidizing mediator concentration is in a range of from 1 to 10 µmole/gram. In some embodiments, the oxidizing mediator concentration is in a range of from 2 to 5 µmole/gram. In some embodiments, the oxidizing mediator concentration is about 3 µmole/gram. In some embodiments, the oxidizing mediator is selected from the group consisting of veratryl alcohol, veratrole and 1,4-dimethoxybenzene. In some embodiments, the oxidizing mediator is veratryl alcohol.

In some embodiments of any of the embodiments described herein, a concentration of the oxidizing mediator in the composition is in a range of from 0.03 µmole/gram to 300 µmole/gram, and a concentration of lignin peroxidase in the composition is in a range of from 1.25 to 40 units/gram. In some embodiments, the oxidizing mediator concentration is in a range of from 0.03 to 30 µmole/gram. In some embodiments, the oxidizing mediator concentration is in a range of from 0.3 to 300 µmole/gram. In some embodiments, the oxidizing mediator concentration is in a range of from 0.3 to 30 µmole/gram. In some embodiments, the oxidizing mediator concentration is in a range of from 1 to 10 µmole/gram. In some embodiments, the oxidizing mediator concentration is in a range of from 2 to 5 µmole/gram. In some embodiments, the oxidizing mediator concentration is about 3 µmole/gram. In some embodiments, the oxidizing mediator is selected from the group consisting of veratryl alcohol, veratrole and 1,4-dimethoxybenzene. In some embodiments, the oxidizing mediator is veratryl alcohol.

In some embodiments of any of the embodiments described herein, a concentration of the oxidizing mediator in the composition is in a range of from 0.03 µmole/gram to 300 µmole/gram, and a concentration of lignin peroxidase in the composition is in a range of from 4 to 40 units/gram. In some embodiments, the oxidizing mediator concentration is in a range of from 0.03 to 30 µmole/gram. In some embodiments, the oxidizing mediator concentration is in a range of from 0.3 to 300 µmole/gram. In some embodiments, the oxidizing mediator concentration is in a range of from 0.3 to 30 µmole/gram. In some embodiments, the oxidizing mediator concentration is in a range of from 1 to 10 µmole/gram. In some embodiments, the oxidizing mediator concentration is in a range of from 2 to 5 µmole/gram. In some embodiments, the oxidizing mediator concentration is about 3 µmole/gram. In some embodiments, the oxidizing mediator is selected from the group consisting of veratryl alcohol, veratrole and 1,4-dimethoxybenzene. In some embodiments, the oxidizing mediator is veratryl alcohol.

In some embodiments of any of the embodiments described herein, a concentration of the oxidizing mediator in the composition is in a range of from 0.03 µmole/gram to 300 µmole/gram, and a concentration of lignin peroxidase in the composition is in a range of from 6 to 125 units/gram. In some embodiments, the oxidizing mediator concentration is in a range of from 0.03 to 30 µmole/gram. In some embodiments, the oxidizing mediator concentration is in a range of from 0.3 to 300 µmole/gram. In some embodiments, the oxidizing mediator concentration is in a range of from 0.3 to 30 µmole/gram. In some embodiments, the oxidizing mediator concentration is in a range of from 1 to 10 µmole/gram. In some embodiments, the oxidizing mediator concentration is in a range of from 2 to 5 µmole/gram. In some embodiments, the oxidizing mediator concentration is about 3 µmole/gram. In some embodiments, the oxidizing mediator is selected from the group consisting of veratryl alcohol, veratrole and 1,4-dimethoxybenzene. In some embodiments, the oxidizing mediator is veratryl alcohol.

In some embodiments of any of the embodiments described herein, a concentration of the oxidizing mediator in the composition is in a range of from 0.03 µmole/gram to 300 µmole/gram, and a concentration of lignin peroxidase in the composition is in a range of from 1.25 to 20 units/gram. In some embodiments, the oxidizing mediator concentration is in a range of from 0.03 to 30 µmole/gram. In some embodiments, the oxidizing mediator concentration is in a range of from 0.3 to 300 µmole/gram. In some embodiments, the oxidizing mediator concentration is in a range of from 0.3 to 30 µmole/gram. In some embodiments, the oxidizing mediator concentration is in a range of from 1 to 10 µmole/gram. In some embodiments, the oxidizing mediator concentration is in a range of from 2 to 5 µmole/gram. In some embodiments, the oxidizing mediator concentration is about 3 µmole/gram. In some embodiments, the oxidizing mediator is selected from the group consisting of veratryl alcohol, veratrole and 1,4-dimethoxybenzene. In some embodiments, the oxidizing mediator is veratryl alcohol.

In some embodiments of any of the embodiments described herein, a concentration of the oxidizing mediator in the composition is in a range of from 0.03 µmole/gram to 300 µmole/gram, and a concentration of lignin peroxidase in the composition is in a range of from 6 to 20 units/gram. In some embodiments, the oxidizing mediator concentration is in a range of from 0.03 to 30 µmole/gram. In some embodiments, the oxidizing mediator concentration is in a range of from 0.3 to 300 µmole/gram. In some embodiments, the oxidizing mediator concentration is in a range of from 0.3 to 30 µmole/gram. In some embodiments, the oxidizing mediator concentration is in a range of from 1 to 10 µmole/gram. In some embodiments, the oxidizing mediator concentration is in a range of from 2 to 5 µmole/gram. In some embodiments, the oxidizing mediator concentration is about 3 µmole/gram. In some embodiments, the oxidizing mediator is selected from the group consisting of veratryl alcohol, veratrole and 1,4-dimethoxybenzene. In some embodiments, the oxidizing mediator is veratryl alcohol.

In some embodiments of any of the embodiments described herein, a concentration of the oxidizing mediator in the composition is in a range of from 0.03 µmole/gram to 300 µmole/gram, and a concentration of lignin peroxidase in the composition is in a range of from 12.5 to 125 units/gram. In some embodiments, the oxidizing mediator concentration is in a range of from 0.03 to 30 µmole/gram. In some embodiments, the oxidizing mediator concentration is in a range of from 0.3 to 300 µmole/gram. In some embodiments, the oxidizing mediator concentration is in a range of from 0.3 to 30 µmole/gram. In some embodiments, the oxidizing mediator concentration is in a range of from 1 to 10 µmole/gram. In some embodiments, the oxidizing mediator concentration is in a range of from 2 to 5 µmole/gram. In some embodiments, the oxidizing mediator concentration is about 3 µmole/gram. In some embodiments, the oxidizing mediator is selected from the group consisting of veratryl alcohol, veratrole and 1,4-dimethoxybenzene. In some embodiments, the oxidizing mediator is veratryl alcohol.

In some embodiments of any of the embodiments described herein, a concentration of the oxidizing mediator in the composition is in a range of from 0.03 µmole/gram to 300 µmole/gram, and a concentration of lignin peroxidase in the composition is in a range of from 1.25 to 12.5 units/gram. In some embodiments, the oxidizing mediator concentration is in a range of from 0.03 to 30 µmole/gram. In some embodiments, the oxidizing mediator concentration is in a range of from 0.3 to 300 µmole/gram. In some embodiments, the oxidizing mediator concentration is in a range of from 0.3 to 30 µmole/gram. In some embodiments, the oxidizing mediator concentration is in a range of from 1 to 10 µmole/gram. In some embodiments, the oxidizing mediator concentration is in a range of from 2 to 5 µmole/gram. In some embodiments, the oxidizing mediator concentration is about 3 µmole/gram. In some embodiments, the oxidizing mediator is selected from the group consisting of veratryl alcohol, veratrole and 1,4-dimethoxybenzene. In some embodiments, the oxidizing mediator is veratryl alcohol.

Several approaches can be used to produce the lignin peroxidase enzyme utilized according to some embodiments of the present invention.

For example, lignin peroxidase isoenzyme H1 can be prepared from the fungus *Phanerochaete chrysosporium*. High levels of enzymatic activity of lignin peroxidase can be produced from the above fungus when grown in a stirred tank reactor (STR) fermentor while being immobilized on polyurethane foam or in suspension [Dosoretz et al., *Appl Environ Microbiol* 1993, 59: 1919-26].

According to some embodiments of the invention the fermentor is connected to a cooling system to maintain a culturing temperature of 37° C. and is stirred at speed of 50-300 rpm (rounds per minute), more preferably, 100-200 rpm, most preferably at 160 rpm. In order to increase the yield of lignin peroxidase activity the fermentor is aerated at an aeration rate of 0.1-1 liter of air per liter of culture medium per minutes. According to presently preferred configurations the fermentor is aerated at an aeration rate of 0.2 liter of air per liter of culture medium per minute.

The *Phanerochaete chrysosporium* is cultured under culturing conditions devoid of manganese ions and containing glycerol as a source of carbon. According to some embodiments of the invention, the glycerol is provided at a concentration range of 3-20 grams per liter. According to some embodiments of the invention the glycerol is provided at a concentration of 6 grams per liter.

During the purification process of lignin peroxidase isoenzyme H1 from the above fungus the enzymatic activity of the purified protein is been further tested by a change in absorbance at 310 nm that occurs due to the oxidation of veratryl alcohol to veratryl aldehyde.

As lignin peroxidase isoenzyme H1 can result from a post-translational de-phosphorylation of isoenzme H2 [Kuan and Tien, *J Biol Chem* 1989, 264:20350-20355], the lignin peroxidase used according to some embodiments of the invention can be prepared by dephosphorylating the lignin peroxidase isoenzyme H2.

According to some embodiments of any of the embodiments of the invention, the lignin peroxidase can be recombinantly expressed using a nucleic acid construct designed to express the coding sequence of lignin peroxidase in a host cell. Non-limiting examples of such nucleic acid sequences are provided in SEQ ID NOs: 3, 5, 7, 9, 11, 13, 15, 17, 19, 21, 23, 25 and 27.

General procedures for expressing a protein such as lignin peroxidase are described in detail herein.

According to some embodiments of any of the embodiments of the invention, the lignin peroxidase is expressed in bacterial cells modified to express the lignin peroxidase as disclosed in U.S. Pat. No. 5,200,338. For example, a bacterial cell, such as, *E. coli*, can be transformed with an expression vector including the lignin peroxidase coding sequence positioned under the regulatory control of a strong constitutive promoter (e.g., SP6) (e.g., coding for a polypeptide having SEQ ID NO: 1). Following expression, the bacterial cells can be lysed and the lignin peroxidase can be collected using chromatographic techniques (see, Billman-Jacobe [*Curr Opin Biotechnol* 1996, 7: 500-4]; Harris and Emtage [*Microbiol. Sci.* 1986, 3: 28-31], for further details).

The lignin peroxidase according to some embodiments of any of the embodiments of the invention can be extracted from mammalian cell lines such as HeLa cells. In this case the lignin peroxidase coding sequence is positioned under a strong mammalian promoter (e.g., CMV) in a suitable expression vector (e.g., pCDNA3.1, Invitrogen Life Technologies, Frederick, Md., USA). Following transfection of HeLa cells with the expression vector, the lignin peroxidase expression product can be extracted from the cells or medium (e.g., by modifying the lignin peroxidase sequence to include a secretion signal) by conventional purification and chromatography techniques (see Cunha and Aires-Barros [*Mol. Biotechnol.* 2002, 20: 29-40] for further details).

Protein Expression:

A nucleic acid construct (also referred to herein as an "expression vector") used in some embodiments of the invention (e.g., for expressing a lignin peroxidase or hydrogen peroxide-producing enzyme described herein) includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N. Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation (e.g., lignin peroxidase mRNA translation). Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Various methods can be used to introduce the expression vector of some embodiments of the invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as electroporation, since higher transfection efficiency can be obtained due to the infectious nature of viruses.

Other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the lignin peroxidase H1 or H2 protein of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the lignin peroxidase H1 or H2 protein and the heterologous protein, the lignin peroxidase protein can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265: 15854-15859].

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of E. coli expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art and are further described hereinbelow can also be used by some embodiments of the invention.

Recovery of the recombinant polypeptide is effected following an appropriate time in culture. The phrase "recovering the recombinant polypeptide" refers to collecting the whole fermentation medium containing the polypeptide and need not imply additional steps of separation or purification. Notwithstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

A Lignin Peroxidase-Containing Kit:

According to another aspect of some embodiments of the invention, there is provided a kit for lightening a topical body site such as skin and/or hair of a subject (e.g., in accordance with a method described herein). The kit comprises a lignin peroxidase (e.g., as described herein), a hydrogen peroxide-producing enzyme (e.g., as described herein) and a substrate of the hydrogen peroxide-producing enzyme (e.g., as described herein). At least one of the lignin peroxidase, hydrogen peroxide-producing enzyme and substrate thereof forms a part of a composition which is packaged individually within the kit.

It is to be understood that a lignin peroxidase-containing kit described herein (e.g., in this section) may contain a lignin peroxidase according to any one of the embodiments described herein relating to lignin peroxidase, and may contain a hydrogen peroxide-producing system (e.g., enzyme and/or substrate) according to any one of the embodiments described herein relating to such a system and/or to a kit containing such a system.

In some embodiments of any of the embodiments described herein, the hydrogen peroxide-producing enzyme forms a part of a first composition and the substrate forms a part of a second composition, wherein the first composition and second composition are packaged individually within the kit. That is, the enzyme and substrate thereof are in separate compositions within the kit, and there is no contact between the enzyme and substrate while they are in the kit.

In some embodiments of any of the embodiments described herein, the second composition further comprises the lignin peroxidase (e.g., the lignin peroxidase is packaged within the same composition as the substrate of the hydrogen peroxide-producing enzyme). In such embodiments, the first composition is also referred to as an "activator", as it results in activation of lignin peroxidase when contacted with the lignin peroxidase-containing second composition.

In exemplary embodiments, the first composition further comprises the lignin peroxidase (e.g., the lignin peroxidase is packaged within the same composition as the hydrogen peroxide-producing enzyme). In such embodiments, the first composition is also referred to as the "enzyme" formulation (e.g., "enzyme cream"), as it comprises the two active enzymes. The second composition is also referred to as an "activator", as it results in activation of lignin peroxidase when contacted with the lignin peroxidase-containing first composition.

In some embodiments of any of the embodiments described herein, the lignin peroxidase forms a part of a third composition within the kit, wherein the third composition is packaged individually within the kit.

In any of the embodiments described herein, each of the first composition described herein, the second composition described herein, and any other part of the hydrogen peroxide-producing composition described herein may be referred to herein also as a formulation, which is packaged within the kit, whereby mixing these formulations results in formation of any of the hydrogen peroxide-producing composition, as described herein.

The first composition and second composition and optional third composition of the kit may be combined so as to prepare a cosmetic composition comprising a lignin peroxidase, a hydrogen peroxide-producing enzyme and a substrate thereof (e.g., as described herein).

In some embodiments of any of the embodiments described herein, the hydrogen peroxide-producing enzyme and the substrate thereof are packaged together (e.g., as part of a single composition) in an air-tight package within the kit (e.g., an air-tight container described herein). The lignin peroxidase may be packaged together with the hydrogen peroxide-producing enzyme and substrate thereof or packaged separately.

In some embodiments of any of the embodiments described herein, a concentration of lignin peroxidase in a composition in the kit which comprises the lignin peroxidase is in a range of from 2.5 to 250 units/gram. In some embodiments, the concentration is in a range of from 8 to 80 units/gram. In some embodiments, the concentration is in a range of from 12 to 40 units/gram. In some embodiments, the concentration is about 25 units/gram.

In some embodiments of any of the embodiments described herein, a concentration of lignin peroxidase in a composition in the kit which comprises the lignin peroxidase is in a range of from 8 to 250 units/gram. In some embodiments, the concentration is in a range of from 12 to 250 units/gram. In some embodiments, the concentration is in a range of from 25 to 250 units/gram.

In some embodiments of any of the embodiments described herein, a concentration of lignin peroxidase in a composition in the kit which comprises the lignin peroxidase is in a range of from 2.5 to 80 units/gram. In some embodiments, the concentration is in a range of from 2.5 to 40 units/gram. In some embodiments, the concentration is in a range of from 2.5 to 25 units/gram.

According to some embodiments of any of the embodiments described herein, the kit further comprises an oxidizing mediator (e.g., as described herein).

In some embodiments of any of the embodiments described herein, the oxidizing mediator is part of a composition in the kit which comprises the lignin peroxidase. In some embodiments, the lignin peroxidase and oxidizing mediator are both part of the first composition. In some embodiments, the lignin peroxidase and oxidizing mediator are both part of the second composition. In some embodiments, the lignin peroxidase and oxidizing mediator are both part of the third composition.

In some embodiments of any of the embodiments described herein, the oxidizing mediator is packaged separately from the composition in the kit which comprises lignin peroxidase. In some embodiments, the lignin peroxidase is a part of the first composition or third composition described herein, and the oxidizing mediator is a part of the second composition. In some embodiments, the lignin peroxidase a part of the second composition or third composition described herein and the oxidizing mediator is a part of the first composition.

In some embodiments of any of the embodiments described herein, a concentration of the oxidizing mediator in the composition in the kit which comprises the oxidizing mediator is in a range of from 0.06 µmole/gram to 600 µmole/gram. In some embodiments, the concentration is in a range of from 0.6 to 60 µmole/gram. In some embodiments, the concentration is in a range of from 2 to 20 µmole/gram. In some embodiments, the concentration is in a range of from 4 to 10 µmole/gram. In some embodiments, the concentration is about 6 µmole/gram.

In some embodiments of any of the embodiments described herein, a concentration of the oxidizing mediator in the composition in the kit which comprises the oxidizing mediator is in a range of from 0.6 µmole/gram to 600 µmole/gram. In some embodiments, the concentration is in a range of from 2 to 600 µmole/gram. In some embodiments, the concentration is in a range of from 6 to 600 µmole/gram.

In some embodiments of any of the embodiments described herein, a concentration of the oxidizing mediator in the composition in the kit which comprises the oxidizing mediator is in a range of from 0.06 µmole/gram to 60 µmole/gram. In some embodiments, the concentration is in a range of from 0.06 to 60 µmole/gram. In some embodiments, the concentration is in a range of from 0.06 to 6 µmole/gram.

In some embodiments of any of the embodiments described herein, a concentration of the oxidizing mediator in the composition in the kit which comprises the oxidizing mediator is in a range of from 0.06 µmole/gram to 600 µmole/gram, and a concentration of lignin peroxidase in a composition in the kit which comprises the lignin peroxidase is in a range of from 2.5 to 250 units/gram. In some embodiments, the oxidizing mediator concentration is in a range of from 0.06 to 60 µmole/gram. In some embodiments, the oxidizing mediator concentration is in a range of from 0.6 to 600 µmole/gram. In some embodiments, the oxidizing mediator concentration is in a range of from 0.6 to 60 µmole/gram. In some embodiments, the oxidizing mediator concentration is in a range of from 2 to 20 µmole/gram. In some embodiments, the oxidizing mediator concentration is in a range of from 4 to 10 µmole/gram. In some embodiments, the oxidizing mediator concentration is about 6 µmole/gram. In some embodiments, the oxidizing mediator is selected from the group consisting of veratryl alcohol, veratrole and 1,4-dimethoxybenzene. In some embodiments, the oxidizing mediator is veratryl alcohol. In some embodiments, the oxidizing mediator and the lignin peroxidase are comprised by the same composition.

In some embodiments of any of the embodiments described herein, a concentration of the oxidizing mediator in the composition in the kit which comprises the oxidizing mediator is in a range of from 0.06 µmole/gram to 600 µmole/gram, and a concentration of lignin peroxidase in a composition in the kit which comprises the lignin peroxidase is in a range of from 8 to 250 units/gram. In some embodiments, the oxidizing mediator concentration is in a range of from 0.06 to 60 µmole/gram. In some embodiments, the oxidizing mediator concentration is in a range of from 0.6 to 600 µmole/gram. In some embodiments, the oxidizing mediator concentration is in a range of from 0.6 to 60 µmole/gram. In some embodiments, the oxidizing mediator concentration is in a range of from 2 to 20 µmole/gram. In some embodiments, the oxidizing mediator concentration is in a range of from 4 to 10 µmole/gram. In some embodiments, the oxidizing mediator concentration is about 6 µmole/gram. In some embodiments, the oxidizing mediator is selected from the group consisting of veratryl alcohol, veratrole and 1,4-dimethoxybenzene. In some embodiments, the oxidizing mediator is veratryl alcohol. In some embodiments, the oxidizing mediator and the lignin peroxidase are comprised by the same composition.

In some embodiments of any of the embodiments described herein, a concentration of the oxidizing mediator in the composition in the kit which comprises the oxidizing mediator is in a range of from 0.06 µmole/gram to 600 µmole/gram, and a concentration of lignin peroxidase in a composition in the kit which comprises the lignin peroxidase is in a range of from 2.5 to 80 units/gram. In some embodiments, the oxidizing mediator concentration is in a range of from 0.06 to 60 µmole/gram. In some embodiments, the oxidizing mediator concentration is in a range of from 0.6 to 600 µmole/gram. In some embodiments, the oxidizing mediator concentration is in a range of from 0.6 to 60 µmole/gram. In some embodiments, the oxidizing mediator concentration is in a range of from 2 to 20 µmole/gram. In some embodiments, the oxidizing mediator concentration is in a range of from 4 to 10 µmole/gram. In some embodiments, the oxidizing mediator concentration is about 6 µmole/gram. In some embodiments, the oxidizing mediator is selected from the group consisting of veratryl alcohol, veratrole and 1,4-dimethoxybenzene. In some embodiments, the oxidizing mediator is veratryl alcohol. In some embodiments, the oxidizing mediator and the lignin peroxidase are comprised by the same composition.

In some embodiments of any of the embodiments described herein, a concentration of the oxidizing mediator in the composition in the kit which comprises the oxidizing mediator is in a range of from 0.06 µmole/gram to 600 µmole/gram, and a concentration of lignin peroxidase in a composition in the kit which comprises the lignin peroxidase is in a range of from 8 to 80 units/gram. In some embodiments, the oxidizing mediator concentration is in a range of from 0.06 to 60 µmole/gram. In some embodiments, the oxidizing mediator concentration is in a range of from 0.6 to 600 µmole/gram. In some embodiments, the oxidizing mediator concentration is in a range of from 0.6 to 60 µmole/gram. In some embodiments, the oxidizing mediator concentration is in a range of from 2 to 20 µmole/gram. In some embodiments, the oxidizing mediator concentration is in a range of from 4 to 10 µmole/gram. In some embodiments, the oxidizing mediator concentration is about 6 µmole/gram. In some embodiments, the oxidizing mediator is selected from the group consisting of veratryl alcohol, veratrole and 1,4-dimethoxybenzene. In some embodiments, the oxidizing mediator is veratryl alcohol. In some embodiments, the oxidizing mediator and the lignin peroxidase are comprised by the same composition.

In some embodiments of any of the embodiments described herein, a concentration of the oxidizing mediator in the composition in the kit which comprises the oxidizing mediator is in a range of from 0.06 µmole/gram to 600 µmole/gram, and a concentration of lignin peroxidase in a composition in the kit which comprises the lignin peroxidase is in a range of from 12 to 250 units/gram. In some embodiments, the oxidizing mediator concentration is in a range of from 0.06 to 60 µmole/gram. In some embodiments, the oxidizing mediator concentration is in a range of from 0.6 to 600 µmole/gram. In some embodiments, the oxidizing mediator concentration is in a range of from 0.6 to 60 µmole/gram. In some embodiments, the oxidizing mediator concentration is in a range of from 2 to 20 µmole/gram. In some embodiments, the oxidizing mediator concentration is in a range of from 4 to 10 µmole/gram. In some embodiments, the oxidizing mediator concentration is about 6 µmole/gram. In some embodiments, the oxidizing mediator is selected from the group consisting of veratryl alcohol, veratrole and 1,4-dimethoxybenzene. In some embodiments, the oxidizing mediator is veratryl alcohol. In some embodiments, the oxidizing mediator and the lignin peroxidase are comprised by the same composition.

In some embodiments of any of the embodiments described herein, a concentration of the oxidizing mediator in the composition in the kit which comprises the oxidizing mediator is in a range of from 0.06 µmole/gram to 600 µmole/gram, and a concentration of lignin peroxidase in a composition in the kit which comprises the lignin peroxidase is in a range of from 2.5 to 40 units/gram. In some embodiments, the oxidizing mediator concentration is in a range of from 0.06 to 60 µmole/gram. In some embodiments, the oxidizing mediator concentration is in a range of from 0.6 to 600 µmole/gram. In some embodiments, the oxidizing mediator concentration is in a range of from 0.6 to 60 µmole/gram. In some embodiments, the oxidizing mediator concentration is in a range of from 2 to 20 µmole/gram. In some embodiments, the oxidizing mediator concentration is in a range of from 4 to 10 µmole/gram. In some embodiments, the oxidizing mediator concentration is about 6 µmole/gram. In some embodiments, the oxidizing mediator is selected from the group consisting of veratryl alcohol, veratrole and 1,4-dimethoxybenzene. In some embodiments, the oxidizing mediator is veratryl alcohol. In some embodiments, the oxidizing mediator and the lignin peroxidase are comprised by the same composition.

In some embodiments of any of the embodiments described herein, a concentration of the oxidizing mediator in the composition in the kit which comprises the oxidizing mediator is in a range of from 0.06 µmole/gram to 600 µmole/gram, and a concentration of lignin peroxidase in a composition in the kit which comprises the lignin peroxidase is in a range of from 12 to 40 units/gram. In some embodiments, the oxidizing mediator concentration is in a range of from 0.06 to 60 µmole/gram. In some embodiments, the oxidizing mediator concentration is in a range of from 0.6 to 600 µmole/gram. In some embodiments, the oxidizing mediator concentration is in a range of from 0.6 to 60 µmole/gram. In some embodiments, the oxidizing mediator concentration is in a range of from 2 to 20 µmole/gram. In some embodiments, the oxidizing mediator concentration is in a range of from 4 to 10 µmole/gram. In some embodiments, the oxidizing mediator concentration is about 6 µmole/gram. In some embodiments, the oxidizing mediator is selected from the group consisting of veratryl alcohol, veratrole and 1,4-dimethoxybenzene. In some embodiments, the oxidizing mediator is veratryl alcohol. In some embodiments, the oxidizing mediator and the lignin peroxidase are comprised by the same composition.

In some embodiments of any of the embodiments described herein, a concentration of the oxidizing mediator in the composition in the kit which comprises the oxidizing mediator is in a range of from 0.06 µmole/gram to 600 µmole/gram, and a concentration of lignin peroxidase in a composition in the kit which comprises the lignin peroxidase is in a range of from 25 to 250 units/gram. In some embodiments, the oxidizing mediator concentration is in a range of from 0.06 to 60 µmole/gram. In some embodiments, the oxidizing mediator concentration is in a range of from 0.6 to 600 µmole/gram. In some embodiments, the oxidizing mediator concentration is in a range of from 0.6 to 60 µmole/gram. In some embodiments, the oxidizing mediator concentration is in a range of from 2 to 20 µmole/gram. In some embodiments, the oxidizing mediator concentration is in a range of from 4 to 10 µmole/gram. In some embodiments, the oxidizing mediator concentration is about 6 µmole/gram. In some embodiments, the oxidizing mediator is selected from the group consisting of veratryl alcohol, veratrole and 1,4-dimethoxybenzene. In some embodiments, the oxidizing mediator is veratryl alcohol. In some embodiments, the oxidizing mediator and the lignin peroxidase are comprised by the same composition.

In some embodiments of any of the embodiments described herein, a concentration of the oxidizing mediator in the composition in the kit which comprises the oxidizing mediator is in a range of from 0.06 µmole/gram to 600 µmole/gram, and a concentration of lignin peroxidase in a composition in the kit which comprises the lignin peroxidase is in a range of from 2.5 to 25 units/gram. In some embodiments, the oxidizing mediator concentration is in a range of from 0.06 to 60 µmole/gram. In some embodiments, the oxidizing mediator concentration is in a range of from 0.6 to 600 µmole/gram. In some embodiments, the oxidizing mediator concentration is in a range of from 0.6 to 60 µmole/gram. In some embodiments, the oxidizing mediator concentration is in a range of from 2 to 20 µmole/gram. In some embodiments, the oxidizing mediator concentration is in a range of from 4 to 10 µmole/gram. In some embodiments, the oxidizing mediator concentration is about 6 µmole/gram. In some embodiments, the oxidizing mediator is selected from the group consisting of veratryl alcohol, veratrole and 1,4-dimethoxybenzene. In some embodiments, the oxidizing mediator is veratryl alcohol. In some embodiments, the oxidizing mediator and the lignin peroxidase are comprised by the same composition.

In some embodiments of any of the embodiments described herein, a concentration of the hydrogen peroxide-producing enzyme (e.g., glucose oxidase) in a composition in any of the kits described herein (e.g., a first composition described herein) is in a range of from 0.25 to 2500 units/gram. In some embodiments, the concentration is in a range of from 2.5 to 250 units/gram. In some embodiments, the concentration is in a range of from 8 to 80 units/gram. In some embodiments, the concentration is in a range of from 12 to 40 units/gram. In some embodiments, the concentration is about 25 units/gram.

In some embodiments of any of the embodiments described herein, a concentration of the hydrogen peroxide-producing enzyme (e.g., glucose oxidase) in a composition in the kit (e.g., a first composition described herein) is in a range of from 2.5 to 2500 units/gram. In some embodiments, the concentration is in a range of from 8 to 2500 units/gram. In some embodiments, the concentration is in a range of from 25 to 2500 units/gram.

In some embodiments of any of the embodiments described herein, a concentration of the hydrogen peroxide-producing enzyme (e.g., glucose oxidase) in a composition in the kit (e.g., a first composition described herein) is in a range of from 0.25 to 250 units/gram. In some embodiments, the concentration is in a range of from 0.25 to 80 units/gram. In some embodiments, the concentration is in a range of from 0.25 to 25 units/gram.

In some embodiments of any of the embodiments described herein, a concentration of lignin peroxidase in a composition in the kit which comprises the lignin peroxidase is in a range of from 2.5 to 250 units/gram, and a concentration of the hydrogen peroxide-producing enzyme in a composition in the kit (e.g., a first composition described herein) is in a range of from 0.25 to 2500 units/gram. In some embodiments, the lignin peroxidase concentration is in a range of from 2.5 to 80 units/gram. In some embodiments, the lignin peroxidase concentration is in a range of from 8 to 250 units/gram. In some embodiments, the lignin peroxidase concentration is in a range of from 8 to 80 units/gram. In some embodiments, the lignin peroxidase concentration is in a range of from 12 to 40 units/gram. In some embodiments, the lignin peroxidase concentration is about 25 units/gram. In some embodiments, the hydrogen peroxide-producing enzyme and the lignin peroxidase are comprised by the same composition. In some embodiments, the hydrogen peroxide-producing enzyme is glucose oxidase.

In some embodiments of any of the embodiments described herein, a concentration of lignin peroxidase in a composition in the kit which comprises the lignin peroxidase is in a range of from 2.5 to 250 units/gram, and a concentration of the hydrogen peroxide-producing enzyme in a composition in the kit (e.g., a first composition described herein) is in a range of from 0.25 to 250 units/gram. In some embodiments, the lignin peroxidase concentration is in a range of from 2.5 to 80 units/gram. In some embodiments, the lignin peroxidase concentration is in a range of from 8 to 250 units/gram. In some embodiments, the lignin peroxidase concentration is in a range of from 8 to 80 units/gram. In some embodiments, the lignin peroxidase concentration is in a range of from 12 to 40 units/gram. In some embodiments, the lignin peroxidase concentration is about 25 units/gram. In some embodiments, the hydrogen peroxide-producing enzyme and the lignin peroxidase are comprised by the same composition. In some embodiments, the hydrogen peroxide-producing enzyme is glucose oxidase.

In some embodiments of any of the embodiments described herein, a concentration of lignin peroxidase in a composition in the kit which comprises the lignin peroxidase is in a range of from 2.5 to 250 units/gram, and a concentration of the hydrogen peroxide-producing enzyme in a composition in the kit (e.g., a first composition described herein) is in a range of from 2.5 to 250 units/gram. In some embodiments, the lignin peroxidase concentration is in a range of from 2.5 to 80 units/gram. In some embodiments, the lignin peroxidase concentration is in a range of from 8 to 250 units/gram. In some embodiments, the lignin peroxidase concentration is in a range of from 8 to 80 units/gram. In some embodiments, the lignin peroxidase concentration is in a range of from 12 to 40 units/gram. In some embodiments, the lignin peroxidase concentration is about 25 units/gram. In some embodiments, the hydrogen peroxide-producing enzyme and the lignin peroxidase are comprised by the same composition. In some embodiments, the hydrogen peroxide-producing enzyme is glucose oxidase.

In some embodiments of any of the embodiments described herein, a concentration of lignin peroxidase in a composition in the kit which comprises the lignin peroxidase is in a range of from 2.5 to 250 units/gram, and a concentration of the hydrogen peroxide-producing enzyme in a composition in the kit (e.g., a first composition described herein) is in a range of from 8 to 2500 units/gram. In some embodiments, the lignin peroxidase concentration is in a range of from 2.5 to 80 units/gram. In some embodiments, the lignin peroxidase concentration is in a range of from 8 to 250 units/gram. In some embodiments, the lignin peroxidase concentration is in a range of from 8 to 80 units/gram. In some embodiments, the lignin peroxidase concentration is in a range of from 12 to 40 units/gram. In some embodiments, the lignin peroxidase concentration is about 25 units/gram. In some embodiments, the hydrogen peroxide-producing enzyme and the lignin peroxidase are comprised by the same composition. In some embodiments, the hydrogen peroxide-producing enzyme is glucose oxidase.

In some embodiments of any of the embodiments described herein, a concentration of lignin peroxidase in a composition in the kit which comprises the lignin peroxidase is in a range of from 2.5 to 250 units/gram, and a concentration of the hydrogen peroxide-producing enzyme in a composition in the kit (e.g., a first composition described herein) is in a range of from 0.25 to 80 units/gram. In some embodiments, the lignin peroxidase concentration is in a range of from 2.5 to 80 units/gram. In some embodiments, the lignin peroxidase concentration is in a range of from 8 to 250 units/gram. In some embodiments, the lignin peroxidase concentration is in a range of from 8 to 80 units/gram. In some embodiments, the lignin peroxidase concentration is in a range of from 12 to 40 units/gram. In some embodiments, the lignin peroxidase concentration is about 25 units/gram. In some embodiments, the hydrogen peroxide-producing enzyme and the lignin peroxidase are comprised by the same composition. In some embodiments, the hydrogen peroxide-producing enzyme is glucose oxidase.

In some embodiments of any of the embodiments described herein, a concentration of lignin peroxidase in a composition in the kit which comprises the lignin peroxidase is in a range of from 2.5 to 250 units/gram, and a concentration of the hydrogen peroxide-producing enzyme in a composition in the kit (e.g., a first composition described herein) is in a range of from 8 to 80 units/gram. In some embodiments, the lignin peroxidase concentration is in a range of from 2.5 to 80 units/gram. In some embodiments, the lignin peroxidase concentration is in a range of from 8 to 250 units/gram. In some embodiments, the lignin peroxidase concentration is in a range of from 8 to 80 units/gram. In some embodiments, the lignin peroxidase concentration is in a range of from 12 to 40 units/gram. In some embodiments, the lignin peroxidase concentration is about 25 units/gram. In some embodiments, the hydrogen peroxide-producing enzyme and the lignin peroxidase are comprised by the same composition. In some embodiments, the hydrogen peroxide-producing enzyme is glucose oxidase.

In some embodiments of any of the embodiments described herein, a concentration of the substrate of the hydrogen peroxide-producing enzyme (e.g., glucose) in a composition in any of the kits described herein (e.g., a second composition described herein) is in a range of from 0.035 µmole/gram to 350 µmole/gram. In some embodiment, the concentration is in a range of from 0.35 to 35 µmole/gram. In some embodiment, the concentration is in a range of from 1 to 12 µmole/gram. In some embodiment, the concentration is in a range of from 2 to 7 µmole/gram. In some embodiment, the concentration is about 3.5 µmole/gram.

In some embodiments of any of the embodiments described herein, a concentration of the substrate of the hydrogen peroxide-producing enzyme (e.g., glucose) in a composition in the kit (e.g., a second composition described herein) is in a range of from 0.35 µmole/gram to 350 µmole/gram. In some embodiment, the concentration is in a range of from 1 to 350 µmole/gram. In some embodiment, the concentration is in a range of from 3.5 to 350 µmole/gram.

In some embodiments of any of the embodiments described herein, a concentration of the substrate of the hydrogen peroxide-producing enzyme (e.g., glucose) in a composition in the kit (e.g., a second composition described herein) is in a range of from 0.035 µmole/gram to 35 µmole/gram. In some embodiment, the concentration is in a range of from 0.035 to 12 µmole/gram. In some embodiment, the concentration is in a range of from 0.035 to 3.5 µmole/gram.

In some embodiments of any of the embodiments described herein, a concentration of the hydrogen peroxide-producing enzyme in a composition in any of the kits described herein (e.g., a first composition described herein) is in a range of from 0.25 to 2500 units/gram, and a concentration of the substrate of the hydrogen peroxide-producing enzyme in a composition in the kit (e.g., a second composition described herein) is in a range of from 0.035 µmole/gram to 350 µmole/gram. In some embodiments, the enzyme concentration is in a range of from 0.25 to 250 units/gram. In some embodiments, the enzyme concentration is in a range of from 2.5 to 2500 units/gram. In some embodiments, the enzyme concentration is in a range of from 2.5 to 250 units/gram. In some embodiments, the enzyme concentration is in a range of from 8 to 80 units/gram. In some embodiments, the enzyme concentration is in a range of from 12 to 40 units/gram. In some embodiments, the enzyme concentration is about 25 units/gram. In some embodiments, the enzyme is glucose oxidase and the substrate is glucose. In some embodiments, the hydrogen peroxide-producing enzyme (e.g., glucose oxidase) and the substrate (e.g., glucose) are comprised by separate compositions in the kit.

In some embodiments of any of the embodiments described herein, a concentration of the hydrogen peroxide-producing enzyme in a composition in any of the kits described herein (e.g., a first composition described herein) is in a range of from 0.25 to 2500 units/gram, and a concentration of the substrate of the hydrogen peroxide-producing enzyme in a composition in the kit (e.g., a second composition described herein) is in a range of from 0.35 µmole/gram to 350 µmole/gram. In some embodiments, the enzyme concentration is in a range of from 0.25 to 250 units/gram. In some embodiments, the enzyme concentration is in a range of from 2.5 to 2500 units/gram. In some embodiments, the enzyme concentration is in a range of from 2.5 to 250 units/gram. In some embodiments, the enzyme concentration is in a range of from 8 to 80 units/gram. In some embodiments, the enzyme concentration is in a range of from 12 to 40 units/gram. In some embodiments, the enzyme concentration is about 25 units/gram. In some embodiments, the enzyme is glucose oxidase and the substrate is glucose. In some embodiments, the hydrogen peroxide-producing enzyme (e.g., glucose oxidase) and the substrate (e.g., glucose) are comprised by separate compositions in the kit.

In some embodiments of any of the embodiments described herein, a concentration of the hydrogen peroxide-producing enzyme in a composition in any of the kits described herein (e.g., a first composition described herein) is in a range of from 0.25 to 2500 units/gram, and a concentration of the substrate of the hydrogen peroxide-producing enzyme in a composition in the kit (e.g., a second composition described herein) is in a range of from 0.035 µmole/gram to 35 µmole/gram. In some embodiments, the enzyme concentration is in a range of from 0.25 to 250 units/gram. In some embodiments, the enzyme concentration is in a range of from 2.5 to 2500 units/gram. In some embodiments, the enzyme concentration is in a range of from 2.5 to 250 units/gram. In some embodiments, the enzyme concentration is in a range of from 8 to 80 units/gram. In some embodiments, the enzyme concentration is in a range of from 12 to 40 units/gram. In some embodiments, the enzyme concentration is about 25 units/gram. In some embodiments, the enzyme is glucose oxidase and the substrate is glucose. In some embodiments, the hydrogen peroxide-producing enzyme (e.g., glucose oxidase) and the substrate (e.g., glucose) are comprised by separate compositions in the kit.

In some embodiments of any of the embodiments described herein, a concentration of the hydrogen peroxide-producing enzyme in a composition in any of the kits described herein (e.g., a first composition described herein) is in a range of from 0.25 to 2500 units/gram, and a concentration of the substrate of the hydrogen peroxide-producing enzyme in a composition in the kit (e.g., a second composition described herein) is in a range of from 0.35 µmole/gram to 35 µmole/gram. In some embodiments, the enzyme concentration is in a range of from 0.25 to 250 units/gram. In some embodiments, the enzyme concentration is in a range of from 2.5 to 2500 units/gram. In some embodiments, the enzyme concentration is in a range of from 2.5 to 250 units/gram. In some embodiments, the enzyme concentration is in a range of from 8 to 80 units/gram. In some embodiments, the enzyme concentration is in a range of from 12 to 40 units/gram. In some embodiments, the enzyme concentration is about 25 units/gram. In some embodiments, the enzyme is glucose oxidase and the substrate is glucose. In some embodiments, the hydrogen peroxide-producing enzyme (e.g., glucose oxidase) and the substrate (e.g., glucose) are comprised by separate compositions in the kit.

In some embodiments of any of the embodiments described herein, a concentration of the hydrogen peroxide-producing enzyme in a composition in any of the kits described herein (e.g., a first composition described herein) is in a range of from 0.25 to 2500 units/gram, and a concentration of the substrate of the hydrogen peroxide-producing enzyme in a composition in the kit (e.g., a second composition described herein) is in a range of from 1 µmole/gram to 350 µmole/gram. In some embodiments, the enzyme concentration is in a range of from 0.25 to 250 units/gram. In some embodiments, the enzyme concentration is in a range of from 2.5 to 2500 units/gram. In some embodiments, the enzyme concentration is in a range of from 2.5 to 250 units/gram. In some embodiments, the enzyme concentration is in a range of from 8 to 80 units/gram. In some embodiments, the enzyme concentration is in a range of from 12 to 40 units/gram. In some embodiments, the enzyme concentration is about 25 units/gram. In some embodiments, the enzyme is glucose oxidase and the substrate is glucose. In some embodiments, the hydrogen peroxide-producing enzyme (e.g., glucose oxidase) and the substrate (e.g., glucose) are comprised by separate compositions in the kit.

In some embodiments of any of the embodiments described herein, a concentration of the hydrogen peroxide-producing enzyme in a composition in any of the kits described herein (e.g., a first composition described herein) is in a range of from 0.25 to 2500 units/gram, and a concentration of the substrate of the hydrogen peroxide-producing enzyme in a composition in the kit (e.g., a second composition described herein) is in a range of from 0.035 µmole/gram to 12 µmole/gram. In some embodiments, the enzyme concentration is in a range of from 0.25 to 250 units/gram. In some embodiments, the enzyme concentration is in a range of from 2.5 to 2500 units/gram. In some embodiments, the enzyme concentration is in a range of from 2.5 to 250 units/gram. In some embodiments, the enzyme concentration is in a range of from 8 to 80 units/gram. In some embodiments, the enzyme concentration is in a range of from 12 to 40 units/gram. In some embodiments, the enzyme concentration is about 25 units/gram. In some embodiments, the enzyme is glucose oxidase and the substrate is glucose. In some embodiments, the hydrogen peroxide-producing enzyme (e.g., glucose oxidase) and the substrate (e.g., glucose) are comprised by separate compositions in the kit.

In some embodiments of any of the embodiments described herein, a concentration of the hydrogen peroxide-producing enzyme in a composition in any of the kits described herein (e.g., a first composition described herein) is in a range of from 0.25 to 2500 units/gram, and a concentration of the substrate of the hydrogen peroxide-producing enzyme in a composition in the kit (e.g., a second composition described herein) is in a range of from 1 µmole/gram to 12 µmole/gram. In some embodiments, the enzyme concentration is in a range of from 0.25 to 250 units/gram. In some embodiments, the enzyme concentration is in a range of from 2.5 to 2500 units/gram. In some embodiments, the enzyme concentration is in a range of from 2.5 to 250 units/gram. In some embodiments, the enzyme concentration is in a range of from 8 to 80 units/gram. In some embodiments, the enzyme concentration is in a range of from 12 to 40 units/gram. In some embodiments, the enzyme concentration is about 25 units/gram. In some embodiments, the enzyme is glucose oxidase and the substrate is glucose. In some embodiments, the hydrogen peroxide-producing enzyme (e.g., glucose oxidase) and the substrate (e.g., glucose) are comprised by separate compositions in the kit.

In some embodiments of any of the embodiments described herein, a concentration of the hydrogen peroxide-producing enzyme in a composition in any of the kits described herein (e.g., a first composition described herein) is in a range of from 0.25 to 2500 units/gram, and a concentration of the substrate of the hydrogen peroxide-producing enzyme in a composition in the kit (e.g., a second composition described herein) is in a range of from 3.5 µmole/gram to 350 µmole/gram. In some embodiments, the enzyme concentration is in a range of from 0.25 to 250 units/gram. In some embodiments, the enzyme concentration is in a range of from 2.5 to 2500 units/gram. In some embodiments, the enzyme concentration is in a range of from 2.5 to 250 units/gram. In some embodiments, the enzyme concentration is in a range of from 8 to 80 units/gram. In some embodiments, the enzyme concentration is in a range of from 12 to 40 units/gram. In some embodiments, the enzyme concentration is about 25 units/gram. In some embodiments, the enzyme is glucose oxidase and the substrate is glucose. In some embodiments, the hydrogen peroxide-producing enzyme (e.g., glucose oxidase) and the substrate (e.g., glucose) are comprised by separate compositions in the kit.

In some embodiments of any of the embodiments described herein, a concentration of the hydrogen peroxide-producing enzyme in a composition in any of the kits described herein (e.g., a first composition described herein) is in a range of from 0.25 to 2500 units/gram, and a concentration of the substrate of the hydrogen peroxide-producing enzyme in a composition in the kit (e.g., a second composition described herein) is in a range of from 0.035 µmole/gram to 3.5 µmole/gram. In some embodiments, the enzyme concentration is in a range of from 0.25 to 250 units/gram. In some embodiments, the enzyme concentration is in a range of from 2.5 to 2500 units/gram. In some embodiments, the enzyme concentration is in a range of from 2.5 to 250 units/gram. In some embodiments, the enzyme concentration is in a range of from 8 to 80 units/gram. In some embodiments, the enzyme concentration is in a range of from 12 to 40 units/gram. In some embodiments, the enzyme concentration is about 25 units/gram. In some embodiments, the enzyme is glucose oxidase and the substrate is glucose. In some embodiments, the hydrogen peroxide-producing enzyme (e.g., glucose oxidase) and the substrate (e.g., glucose) are comprised by separate compositions in the kit.

In some embodiments of any of the embodiments described herein, a concentration of the hydrogen peroxide-producing enzyme in a composition in any of the kits described herein (e.g., a first composition described herein) is in a range of from 0.25 to 2500 units/gram, and a concentration of the substrate of the hydrogen peroxide-producing enzyme in a composition in the kit (e.g., a second composition described herein) is in a range of from 2 µmole/gram to 7 µmole/gram. In some embodiments, the enzyme concentration is in a range of from 0.25 to 250 units/gram. In some embodiments, the enzyme concentration is in a range of from 2.5 to 2500 units/gram. In some embodiments, the enzyme concentration is in a range of from 2.5 to 250 units/gram. In some embodiments, the enzyme concentration is in a range of from 8 to 80 units/gram. In some embodiments, the enzyme concentration is in a range of from 12 to 40 units/gram. In some embodiments, the enzyme concentration is about 25 units/gram. In some embodiments, the enzyme is glucose oxidase and the substrate is glucose. In some embodiments, the hydrogen peroxide-producing enzyme (e.g., glucose oxidase) and the substrate (e.g., glucose) are comprised by separate compositions in the kit.

In some embodiments of any of the embodiments described herein, the first composition of the kit comprises glucose oxidase at a concentration in a range of from 2.5 to 250 units/gram (e.g., a glucose oxidase concentration described herein), and the second composition of the kit comprises D-glucose at a concentration in a range of from 0.35 µmole/gram to 35 µmole/gram (e.g., a glucose concentration described herein).

In some embodiments of any of the embodiments described herein, the first composition of the kit comprises glucose oxidase at a concentration in a range of from 2.5 to 250 units/gram (e.g., a glucose oxidase concentration described herein), and lignin peroxidase at a concentration of 2.5 to 250 units/gram (e.g., a lignin peroxidase concentration described herein); and the second composition of the kit comprises D-glucose at a concentration in a range of from 0.35 µmole/gram to 35 µmole/gram (e.g., a glucose concentration described herein).

The kits described herein may include additional compositions (e.g., cosmetic compositions), besides the compositions comprising one or more active ingredients as described herein (e.g., an agent which exhibits an activity in a presence of hydrogen peroxide, a lignin peroxidase, a hydrogen peroxide-producing enzyme, a substrate of hydrogen peroxide-producing enzyme and/or an oxidizing mediator).

In some embodiments of any of the embodiments described herein, the kit further comprises a wash composition (e.g., as described herein), such as a facial wash, for cleaning a topical body site prior to contact with a composition described herein.

In some embodiments of any of the embodiments described herein, the kit includes appropriate instructions for use and labels indicating approval by a regulatory agency for the indicated use, as described herein.

Formulation of Compositions:

According to some embodiments of any of the embodiments and any of the aspects of embodiments of the invention described herein, the active ingredient(s) described herein (e.g., an agent which exhibits an activity in a presence of hydrogen peroxide, a lignin peroxidase, a hydrogen peroxide-producing enzyme, a substrate of hydrogen peroxide-producing enzyme and/or an oxidizing mediator) may be used in a composition comprising the active ingredient(s) per se or in combination with additional chemical components such as physiologically suitable carriers and excipients. Compositions include a cosmetic or pharmaceutical composition described herein (which exhibit a cosmetic or pharmaceutical activity as described herein) and compositions within a kit (e.g., a first composition, a second composition, and/or a third composition, as described herein) which may be used to prepare a cosmetic or pharmaceutical composition described herein (although they may be inactive by themselves).

The purpose of a cosmetic or pharmaceutical composition comprising carriers and excipients is to facilitate administration of the active ingredient to an organism. In embodiments wherein an activity exhibited by the composition is cosmetic, as defined herein, the composition is also referred to herein as a "cosmetic composition". In embodiments wherein an activity exhibited by the composition is pharmaceutical, the composition is also referred to herein as a "pharmaceutical composition".

Hereinthroughout, the term "pharmaceutical" means that the composition or kit are for exhibiting a therapeutic effect when applied on a subject's bodily site as described herein.

Hereinafter, the phrase "suitable carrier" refers to a carrier or a diluent that does not cause significant irritation to an organism and does not abrogate the biological activity and properties of the active ingredient(s). In embodiments wherein an activity exhibited by the active ingredient(s) is cosmetic, such a carrier is also referred to herein as a "cosmetically or cosmeceutically acceptable carrier". In embodiments wherein an activity exhibited by the active ingredient(s) is pharmaceutical, such a carrier is also referred to herein as a "pharmaceutically acceptable carrier".

Herein the term "excipient" refers to an inert substance added to a composition to further facilitate administration of an active ingredient(s). Examples, without limitation, of excipients include calcium carbonate, calcium phosphate, various sugars and types of starch, cellulose derivatives, gelatin, vegetable oils and polyethylene glycols.

Compositions of the present invention may be manufactured by processes well known in the art, e.g., by means of conventional mixing, dissolving, granulating, dragee-making, levigating, emulsifying, encapsulating, entrapping or lyophilizing processes.

Compositions for use in accordance with some embodiments of the invention thus may be formulated in conventional manner using one or more suitable carriers comprising excipients and auxiliaries, which facilitate processing of the active ingredient(s) into preparations. Proper formulation is dependent upon the administration approach chosen.

Alternatively, the active ingredient(s) may be in a powder form for constitution with a suitable vehicle, e.g., sterile, pyrogen-free water based solution, before use.

Compositions according to some embodiments of any of the embodiments and any of the aspects described herein may be formulated in any of a variety of forms utilized by the cosmetic industry (e.g., for topical use), such as, for example, a mask, a serum, a lotion, a cream, a shampoo, a gel, and/or a toner. As will be apparent to the skilled person, suitability of a formulations will depend on the type of surface to be contacted with the active ingredient(s)—thus, for example, a shampoo formulation is suitable for contacting hair, a facial mask is suitable for contacting facial skin, and so forth.

Methods for preparing compositions having properties such as described herein are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

According to some embodiments of any of the embodiments of the invention, the cosmetic composition is formulated viscous enough to remain on the treated area, does not readily evaporate, and/or is not easily removed by rinsing with water.

As used herein the term "serum" refers to an aqueous solution which is formulated for topical application.

According to some embodiments of any of the embodiments of the invention, the serum is a thickened aqueous cosmetic solution. According to some embodiments of the invention, the serum is a clear to slight hazy aqueous solution.

According to some embodiments of any of the embodiments of the invention, the serum is formulated to remain on a topical body site and does not need to be removed by water, soap and/or cleansers.

According to some embodiments of any of the embodiments of the invention, upon topical application of the serum (e.g., to skin), the serum is absorbed rapidly, leaving a cosmetically elegant silky smooth feel.

According to some embodiments of any of the embodiments of the invention, the serum is incorporated within a mask (a cosmetic mask).

In some embodiments of any of the embodiments described herein, the serum comprises ingredients as presented in Table 2:

TABLE 2

Serum composition according to some embodiments

| Ingredient | Weight percentage range |
|---|---|
| Water | 75-100% |
| Active ingredient(s) | As described herein |
| Glycerin | 5-10% |
| Polyacrylate-13 | 0.1-1% |
| Dimethicone | 0.1-1% |
| Dicaprylyl carbonate | 0.1-1% |
| Cetyl alcohol | 0.1-1% |
| Stearyl alcohol | 0.1-1% |
| Phenoxyethanol | 0.1-1% |
| Portulaca oleracea | 0-1% |
| Polyisobutene | 0.1-1% |
| Butylene glycol | 0-1% |
| Pullulan | 0-0.1% |
| Polysorbate 20 | 0-0.1% |
| PEG-4 Laurate | 0-0.1% |
| PEG-4 Dilaurate | 0-0.1% |
| PEG-4 | 0-0.1% |
| Iodopropynyl butylcarbamate | 0-0.1% |

In some embodiments of any of the embodiments described herein, a composition as described herein (e.g., serum, lotion, cream) comprises a dermatologically acceptable emollient. Such compositions preferably contain from about 2% to about 50% of the emollient. As used herein, "emollient" refers to a material useful for the prevention or relief of dryness, as well as for the protection of skin. A wide variety of suitable emollients are known and may be used herein. See, e.g., Sagarin, Cosmetics, Science and Technology, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and an effective amount of active ingredient(s) described herein.

In some embodiments of any of the embodiments described herein, the cream or lotion comprises ingredients as presented in Table 3:

TABLE 3

Cream or lotion composition according to some embodiments

| Ingredient | Weight percentage range |
|---|---|
| Water | 50-75% |
| Active ingredient(s) | As described herein |
| Glycerin | 5-10% |
| Butyrospermum Parkii butter | 0-5% |
| Dimethicone | 1-5% |
| Dicaprylyl carbonate | 1-5% |
| Trehalose | 0-5% |
| Caprylic capric triglyceride | 0-1% |
| Cetyl alcohol | 0.1-1% |
| Jojoba ester | 0-1% |
| Stearyl alcohol | 0.1-1% |
| Polyacrylate-13 | 0.1-1% |
| Cetyl palmitate | 0-1% |
| Myristyl myristate | 0-1% |
| Phenoxyethanol | 0.1-1% |
| Polyisobutene | 0.1-1% |
| Pullulan | 0-1% |
| Polysorbate 20 | 0-0.1% |
| PEG- 4 laurate | 0-0.1% |
| PEG-4 dilaurate | 0-0.1% |
| PEG-4 | 0-0.1% |
| Iodopropynyl butylcarbamate | 0-0.1% |

In exemplary embodiments, the cream or lotion comprises ingredients as presented in Table 4:

TABLE 4

Cream or lotion composition according to exemplary embodiments

| Ingredient | Weight percentage range |
|---|---|
| Water | 75-100% |
| Active ingredient(s) | As described herein |
| Glycerin | 5-10% |
| Propylene glycol | 1-5% |
| Dicaprylyl carbonate | 0.1-1% |
| Dimethicone | 0.1-1% |
| Polyacrylate-13 | 0.1-1% |
| Cetyl alcohol | 0.1-1% |
| Paraffinum liquidum | 0.1-1% |
| Stearyl alcohol | 0.1-1% |
| Phenoxyethanol | 0.1-1% |
| Polyisobutene | 0.1-1% |
| Polysorbate 20 | 0-0.1% |
| PEG- 4 laurate | 0-0.1% |
| PEG-4 dilaurate | 0-0.1% |
| PEG-4 | 0-0.1% |
| Iodopropynyl butylcarbamate | 0-0.1% |
| Chlorphenesin | 0-1% |
| Caesalpinia spinosa gum | 0-1% |
| Citric acid | 0-0.1% |

As used herein the term "mask" refers to a cosmetic mask which comprises the active ingredient(s) as described herein and which is topically applied in order to maintain contact of the active ingredient(s) with a topical region, for example, in order to lighten the topical region.

Various types of cosmetic masks are known in the cosmetic industry. These include, but are not limited to a mask having a solid support, a rinse-off mask, a peeled-off mask, or a mask which hardens or polymerizes after a set period of time.

As used herein the phrase "rinse-off mask" refers to a cosmetic composition formulated in order to be topically applied in a relatively thick layer and left for a certain period of time, generally from a few minutes to several tens of minutes, and in order to be, at the end of this period of time, rinsed off with water or also simply wiped off.

Suitable masks and techniques for preparing masks with an active ingredient(s) such as described herein are described in International Patent Application Publication WO 2012/153336.

In some embodiments of any of the embodiments described herein, the form of the composition is determined, at least in part, by selecting a suitable carrier.

In some embodiments of any of the embodiments described herein, the carrier comprises an emulsion. Such carriers include, without limitation, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to some embodiments of any of the embodiments of the invention generally contain an effective amount of active ingredient(s) disclosed herein and oil. The active ingredient(s) (e.g., an agent which exhibits an activity in a presence of hydrogen peroxide, a lignin peroxidase, a hydrogen peroxide-producing enzyme, a substrate of hydrogen peroxide-producing enzyme and/or an oxidizing mediator) and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560, issued to Dickert, et al. Aug. 28, 1973; U.S. Pat. No. 4,421,769, issued to Dixon, et al., Dec. 20, 1983; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon topical application. Anti-foaming agents include high molecular weight silicones and other materials well known in the art for such use.

In some embodiments of any of the embodiments described herein, the emulsion is an oil-in-water emulsion, having a continuous aqueous phase and a hydrophobic, water-insoluble phase ("oil phase") dispersed therein. Examples of suitable carriers comprising oil-in-water emulsions are described in U.S. Pat. Nos. 5,073,371 and 5,073,372.

In some embodiments of any of the embodiments described herein, the oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent. The preferred structuring agents of the present invention are selected from the group consisting of stearic acid, palmitic acid, stearyl alcohol, cetyl alcohol, behenyl alcohol, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

A wide variety of anionic surfactants are also useful herein, as described, for example, in U.S. Pat. No. 3,929,678. In addition, amphoteric and zwitterionic surfactants are also useful herein.

In some embodiments of any of the embodiments described herein, the oil-in-water emulsion comprises from about 25% to about 98%, preferably from about 65% to about 95%, more preferably from about 70% to about 90% water by weight of the topical carrier.

In some embodiments of any of the embodiments described herein, the emulsion is a water-in-silicone emulsion. Water-in-silicone emulsions contain a continuous silicone phase and a dispersed aqueous phase. Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil.

The continuous silicone phase may contain one or more non-silicone oils. Concentrations of non-silicone oils in the continuous silicone phase are preferably minimized or avoided altogether so as to further enhance oxidative stability of the active ingredient(s) in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

Useful topical compositions according to some embodiments of any of the embodiments of the present invention comprise from about 30% to about 90%, more preferably from about 50% to about 85%, and most preferably from about 70% to about 80% of a dispersed aqueous phase. The term "dispersed phase" is well-known to one skilled in the art it implies that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous oil and/or silicone phase (e.g., as described herein). The aqueous phase can be water, or a combination of water and one or more water soluble or dispersible ingredients. Non-limiting examples of such optional ingredients include thickeners, acids, bases, salts, chelants, gums, water-soluble or dispersible alcohols and polyols, buffers, preservatives, sunscreening agents, colorings, and the like.

The topical compositions of some embodiments of the invention typically comprise from about 25% to about 90%, preferably from about 40% to about 80%, more preferably from about 60% to about 80%, water in the dispersed aqueous phase by weight of the composition.

The emulsions of some embodiments of the invention comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the oil and/or silicone phase. Known or conventional emulsifying agents can be used in the composition, provided that the selected emulsifying agent is chemically and physically compatible with essential components of the composition, and provides the desired dispersion characteristics. Suitable emulsifiers include emulsifiers known by those skilled in the art for use in topical personal care products.

Suitable emulsifiers include any of a wide variety of known cationic, anionic, zwitterionic, and amphoteric surfactants. See, McCutcheon's. Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al. issued to Dec. 20, 1983; and U.S. Pat. No. 3,755,560. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued to Sep. 29, 1992; U.S. Pat. No. 5,151,210 to Steuri et al., issued to Sep. 29, 1992; U.S. Pat. Nos. 5,120,532; 4,387,090; 3,155,591; 3,929,678; 3,959,461; McCutcheon's, Detergents & Emulsifiers (North American edition 1979) M.C. Publishing Co.; and Schwartz, et al., Surface Active Agents, Their chemistry and Technology, New York: Interscience Publishers, 1949.

Alternatively, other useful cationic emulsifiers include amino-amides. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl(myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Determination of an effective amount of active ingredient (s) is well within the capability of those skilled in the art, especially in light of the detailed disclosure provided herein.

For any preparation used in the methods of the invention, the therapeutically effective amount or dose can be estimated initially from in vitro assays. In addition, a dose can be formulated in ex vivo systems (e.g., ex vivo skin, hair and/or nail) or in animal models to achieve a desired concentration or titer. Such information can be used to more accurately determine useful doses in humans.

In order to enhance the percutaneous absorption of the active ingredients (e.g., lignin peroxidase, and/or oxidizing mediator), one or more of a number of agents can be added to the composition including, but not limited to, dimethylsulfoxide, dimethylacetamide, dimethylformamide, surfactants, azone, alcohol, acetone, propylene glycol, polyethylene glycol, and butylene glycol.

The compositions described herein may also include additional components which are added, for example, in order to enrich the compositions with fragrance and nutrition factors (e.g., skin or hair nutrition factors).

Such components are selected suitable for topical use on a human without inducing toxicity, incompatibility, instability, allergic response, and the like within the scope of sound medical judgment. In addition, such optional components are useful provided that they do not unacceptably alter the benefits of the active compounds of the invention.

The CTFA Cosmetic Ingredient Handbook, Second Edition (1992) describes a wide variety of non-limiting cosmetic ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and/or occlusive), skin soothing and/or healing agents (e.g., panthenol and derivatives (e.g., ethyl panthenol), aloe vera, pantothenic acid and its derivatives, allantoin, bisabolol, and dipotassium glycyffhizinate), skin treating agents, thickeners, and vitamins and derivatives thereof.

As compositions according to some embodiments described herein are for utilization in vivo, the composition is preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Materials:
Glucose oxidase (stabilizer-free) was obtained from Sigma-Aldrich; Lignin peroxidase isoenzyme H1 (from *P. chrysosporium*) was prepared as described in International Patent Application Publication WO2004/052275, with the following minor modifications: a spore solution with $7.5*10^4$ spores/ml was directly spiked to the growth medium; the growth medium further comprised yeast extract and nutrient broth; and aeration of the fermentor was 4 liters/minute with agitation of 150 rotations per minute (lignin peroxidases from of other white rot fungi are also contemplated for use in embodiments of the invention);

Veratryl alcohol was obtained from Fluka.

Cream Formulation:

Exemplary formulations were prepared in the form of two complementary creams: an enzyme cream comprising 25 units/gram LIP isoenzyme H1 fraction, 25 units/gram GOX and 0.10 weight percent veratryl alcohol (6 mmol/kg of cream), and the complementary activator cream comprised glucose (3.5 mmol/kg of cream).

For comparison, a complementary enzyme cream and activator cream were formulated for activation of LIP by non-enzymatically produced $H_2O_2$. This enzyme cream comprised the LIP isoenzyme H1 fraction (25 units/gram) and veratryl alcohol (6 mmol/kg of cream) without GOX, and the complementary activator cream comprised $H_2O_2$ (3.53 mmol/kg of cream).

Other ingredients (e.g., the carrier) in the creams were as described in Table 5 below.

TABLE 5

Non-active ingredients of exemplary creams

| Ingredient | Weight percentage | Trade names and other details |
|---|---|---|
| Glycerin | 8.0% | Superol ® V |
| Propylene glycol | 2.0% | |

TABLE 5-continued

Non-active ingredients of exemplary creams

| Ingredient | Weight percentage | Trade names and other details |
|---|---|---|
| Dimethicone | 1.0% | xiameter ® pmx-200 |
| Dicaprylyl carbonate | 1.0% | Cetiol ® CC |
| Paraffinum liquidum | 0.50% | Draekol ® 19 |
| Cetyl alcohol | 0.50% | Lanette ® C16 98-100MY |
| Stearyl alcohol | 0.50% | Lanette ® C18 98-100MY |
| Polyisobutene | 0.200-0.213% | 0.80-0.85% Sepiplus ™ 400 (25% polyisobutene, 5% polysorbate 20 and 70% polyacrylate 13) |
| Polysorbate 20 | 0.040-0.043% | |
| Polyacrylate 13 | 0.560-0.595% | |
| Phenoxyethanol | 0.50% | |
| Chlorphenesin | 0.30% | Elestab ® CPN |
| *Caesalpinia spinosa* gum | 0.30% | Solagum ™ Tara |
| Citric acid | 0.011-0.040% | Added as aqueous solution |
| Deionized water | To 100% | |

Visual Analogue Scale (VAS):

A visual analogue scale (VAS) is a method that is used to measure a characteristic or attitude that is believed to range across a continuum of values which cannot easily be directly measured. The VAS was presented as a horizontal line, anchored by word descriptors at each end, as described below. The ends of the scale were labeled by the values 0 (for most desirable outcomes) and 10 (for least desirable outcome). Statistical significance was determined by calculating p values according to repeated measures ANOVA. A VAS was used to evaluate each of the following variables:

Uniformity of pigmentation (anchored by the descriptors "uniform, even" and "uneven, blotchy, mottled");

Clarity (anchored by the descriptors "clear, even" and "dull, opaque");

Lightening/Brightening (anchored by the descriptors "light/bright appearance" and "dull, matte");

Skin tone (anchored by the descriptors "even, healthy skin color" and "uneven, discolored appearance");

Radiance (anchored by the descriptors "radiant, luminous appearance" and "dull, matte, sallow appearance"); and Overall appearance (anchored by the descriptors "healthy looking" and unhealthy looking").

Digital Photography:

Digital photography of the faces of treated subjects was performed using a VISTA®-CR facial imaging system, placed in an environment with stable and consistent ambient lighting. The system remained in the same location/orientation for different visits by each subject.

Example 1

Oxidation of Melanin by Lignin Peroxidase, Glucose Oxidase and Glucose in Cream Formulation In order to evaluate the ability of lignin peroxidase (LIP) to lighten skin upon activation by an enzymatic source of hydrogen peroxide, an enzyme cream comprising LIP, veratryl alcohol and GOX (glucose oxidase) and an activator cream comprising glucose were prepared as described hereinabove, and tested on solubilized melanin. The results were compared with those obtained with an enzyme cream comprising LIP and veratryl alcohol and an activator cream comprising hydrogen peroxide, prepared as described hereinabove.

0.3 gram of each enzyme cream was first mixed with melanin (140 µg/ml), resulting in a grayish black color. 0.3 gram of the complementary activator cream was then added.

As shown in FIG. 1, the color of each enzyme cream formulation changed from grayish black to beige immediately after addition of the activator cream.

These results indicate that LIP is efficiently activated by the $H_2O_2$ produced enzymatically by the GOX-glucose system, to a comparable degree as is obtained with the conventional non-enzymatic $H_2O_2$ activation system.

Example 2

Skin Lightening by Lignin Peroxidase, Glucose Oxidase and Glucose in Cream Formulation Upon Treatment for 21 Days The exemplary enzyme and activator creams described herein were tested for their ability to lighten skin in vivo.

Lignin peroxidase, glucose oxidase and glucose were administered to 10 female subjects (aged 23-65), of which 8 completed the study. Compositions were applied to facial skin according to the following regimen:

Morning

Step 1—ELURE™ facial wash

Step 2—cream comprising lignin peroxidase and glucose oxidase (as described in Materials and Methods section)

Step 3—activator cream comprising glucose (as described in Materials and Methods section)

Step 4—SPF 30 sunscreen (for reducing formation of new melanin)

Evening

Step 1—facial wash

Step 2—cream comprising lignin peroxidase and glucose oxidase

Step 3—activator cream comprising glucose

After the cream comprising lignin peroxidase and glucose oxidase was applied and absorbed by the skin, the activator cream was applied.

Skin color was measured using a Mexameter® skin colorimeter, which was used to evaluate melanin and erythema (hemoglobin) contributions to the skin color. The skin color was measured in various regions (forehead, right cheek, left cheek, and spots of interest). In each region skin color was measured at different points and the results were averaged. Skin color was assessed on day 0 (i.e., prior to treatment) and on days 7 and 21 of the treatment.

As shown in FIGS. 2A-9B, the treatment resulted in at least some reduction in melanin content, in all 8 subjects tested, and the reductions in melanin content were usually treatment duration-dependent (FIGS. 2A, 6A, 7A, 9A).

As further shown therein, the treatment did not have any consistent effect on erythema levels.

As shown in FIGS. 3A, 5A and 6A, the treatment resulted in reduction in melanin content of most spots on the skin.

In one subject (FIG. 9B), an increase of erythema of the cheeks on day 21 was observed, but judged to be caused by irritation unrelated to the treatment (irritation by toner used to remove smudged eye shadow).

These results indicate that treatment with lignin peroxidase, glucose oxidase and glucose is effective at lightening skin by decreasing melanin content, without causing significant irritation of the skin.

Example 3

Skin Lightening by Lignin Peroxidase, Glucose Oxidase and Glucose in Cream Formulation Upon Treatment for 8 Weeks The formulation and daily regimen described in Example 2 were tested on 28 female volunteer subjects (aged 33-50) with apparent but mild, diffuse hyperpigmentation including melasma, for a period of 8 weeks. Subjects fulfilling any of the following criteria were excluded: sensitive, hypersensitive, or with atopic skin; history of allergy to cosmetic products or skin cleansers; history of a disease/condition or concurrent illness that could interfere with the outcome of the study; pregnant, planning to be pregnant, or breast feeding; skin problems in the area for testing, including skin diseases, moles, acne, red spots, telangiectasis, etc; dermatologist treatments, or procedures with potential interference within the last 3 months; currently involved in, or participated in any clinical skin care study within the last 3 months; judged by a physician to be unsuitable for enrollment in this clinical trial.

The effect of the formulation was assessed by evaluating skin pigmentation at 0, 4, 6 and 8 weeks from the beginning of treatment, using the following techniques:

1) instrumental measurement using a Mexameter® skin colorimeter;
2) visual analogue scale (VAS) assessment by a dermatologist;
3) digital photography with VISTA®-CR facial imaging system; and
4) self-assessment by subjects.

As shown in FIGS. 10A and 10B, the formulation progressively lowered the melanin index in pigmented skin (FIG. 10A) and non-pigmented skin (FIG. 10B) throughout the 8 weeks of treatment (as determined using a Mexameter® skin colorimeter).

Furthermore, after 4 weeks, the melanin index in pigmented skin was lowered in 22 of the 28 subjects (78.6%), and the melanin index in non-pigmented skin was lowered in 20 of the 28 subjects (71.4%). After 6 and 8 weeks, the melanin index in each of pigmented and non-pigmented skin was lowered in 27 of the 28 subjects (96.4%).

A visual analogue scale (VAS) was used, as described in the Materials and Methods section, to evaluate uniformity of pigmentation, clarity, lightness/brightness, tone, radiance and overall appearance of treated skin, at various time points over the course of the treatment.

As shown in FIGS. 11-16, as well as in Tables 6 and 7, the formulation progressively enhanced the uniformity of pigmentation (FIG. 11), clarity (FIG. 12), lightness/brightness (FIG. 13), tone (FIG. 14), radiance (FIG. 15) and overall appearance (FIG. 16) of treated skin, over the course of 8 weeks of treatment.

The average degree of improvements at each time point shown in FIGS. 11-16 are presented in Table 6:

TABLE 6

Average improvement and statistical significance of skin appearance relative to beginning of treatment (n = 28)

| | Improvement (%) (p value) | | |
|---|---|---|---|
| | after 4 weeks | after 6 weeks | after 8 weeks |
| Uniformity of pigmentation | 1.26% (0.223) | 2.96% (0.106) | 5.47% (0.046) |
| Clarity | 4.00% (0.004) | 4.65% (0.033) | 8.59% (0.002) |
| Lightening/ Brightening | 9.28% (0.000) | 8.09% (0.001) | 11.52% (0.000) |
| Tone | 8.03% (0.000) | 6.13% (0.015) | 12.53% (0.000) |
| Radiance | 11.64% (0.000) | 12.15% (0.000) | 18.38% (0.000) |
| Overall Appearance | 14.25% (0.000) | 13.21% (0.000) | 21.57% (0.000) |

FIG. 17 shows the changes in facial complexion in individual subjects treated for 8 weeks with the formulation.

The percentages of the 28 subjects which showed significant improvement in clarity, lightening/brightening, skin tone, radiance and/or overall appearance of whole face complexion after 4, 6 and 8 weeks of treatment are presented in Table 7:

TABLE 7

Percentage of subjects showing improvement of skin appearance relative to beginning of treatment (n = 28)

| | after 4 weeks | after 6 weeks | after 8 weeks |
|---|---|---|---|
| Uniformity of pigmentation | 46.4% (13/28) | 60.7% (17/28) | 67.9% (19/28) |
| Clarity | 67.9% (19/28) | 64.3% (18/28) | 67.9% (19/28) |
| Lightening/ Brightening | 89.3% (25/28) | 78.6% (22/28) | 75.0% (21/28) |
| Tone | 78.6% (22/28) | 67.9% (19/28) | 82.1% (23/28) |
| Radiance | 92.9% (26/28) | 92.9% (26/28) | 96.4% (27/28) |
| Overall Appearance | 92.9% (26/28) | 82.1% (23/28) | 89.3% (25/28) |

As shown in Table 8, satisfaction of the subjects with the formulation progressively increased over the course of 8 weeks of treatment (as determined according to self-assessment by questionnaire).

TABLE 8

Responses of subjects to question "Overall, are you satisfied with the product you used?"

| | 0 weeks | | 4 weeks | | 6 weeks | | 8 weeks | |
|---|---|---|---|---|---|---|---|---|
| Response | n | % | n | % | n | % | n | % |
| Strongly disagree (1) | 0 | 0.0 | 0 | 0.0 | 0 | 0.0 | 0 | 0.0 |
| Disagree (2) | 0 | 0.0 | 1 | 3.6 | 0 | 0.0 | 1 | 3.6 |
| Fair (3) | 27 | 96.4 | 9 | 32.1 | 8 | 28.6 | 6 | 21.4 |
| Agree (4) | 1 | 3.6 | 18 | 64.3 | 16 | 57.1 | 18 | 64.3 |
| Strongly agree (5) | 0 | 0.0 | 0 | 0.0 | 4 | 14.3 | 3 | 10.7 |

Furthermore, as shown in Table 9, satisfaction of the subjects with the formulation was expressed over the course of 8 weeks of treatment with respect to every topic asked about in the questionnaire.

TABLE 9

Responses of subjects to specific questionnaire items (n = 28)

| Questionnaire Item | Response | 0 weeks n | 0 weeks % | 4 weeks n | 4 weeks % | 6 weeks n | 6 weeks % | 8 weeks n | 8 weeks % |
|---|---|---|---|---|---|---|---|---|---|
| Overall, have you felt improvement effect of skin brightness after application? | Strongly disagree (1) | 0 | 0.0 | 0 | 0.0 | 0 | 0.0 | 0 | 0.0 |
| | Disagree (2) | 0 | 0.0 | 0 | 0.0 | 0 | 0.0 | 1 | 3.6 |
| | Fair (3) | 26 | 92.9 | 11 | 39.3 | 4 | 14.3 | 3 | 10.7 |
| | Agree (4) | 2 | 7.1 | 15 | 53.6 | 23 | 82.1 | 22 | 78.6 |
| | Strongly agree (5) | 0 | 0.0 | 2 | 7.1 | 1 | 3.6 | 2 | 7.1 |
| Does the skin color on the pigmented area lighten? | Strongly disagree (1) | 0 | 0.0 | 0 | 0.0 | 0 | 0.0 | 0 | 0.0 |
| | Disagree (2) | 0 | 0.0 | 0 | 0.0 | 0 | 0.0 | 2 | 7.1 |
| | Fair (3) | 27 | 96.4 | 17 | 60.7 | 11 | 39.3 | 8 | 28.6 |
| | Agree (4) | 1 | 3.6 | 10 | 35.7 | 16 | 57.1 | 17 | 60.7 |
| | Strongly agree (5) | 0 | 0.0 | 1 | 3.6 | 1 | 3.6 | 1 | 3.6 |
| Do you feel the change of pigmented area? | Strongly disagree (1) | 0 | 0.0 | 0 | 0.0 | 0 | 0.0 | 0 | 0.0 |
| | Disagree (2) | 1 | 3.6 | 0 | 0.0 | 0 | 0.0 | 1 | 3.6 |
| | Fair (3) | 27 | 96.4 | 19 | 67.9 | 15 | 53.6 | 15 | 53.6 |
| | Agree (4) | 0 | 0.0 | 9 | 32.1 | 12 | 42.9 | 10 | 35.7 |
| | Strongly agree (5) | 0 | 0.0 | 0 | 0.0 | 1 | 3.6 | 2 | 7.1 |
| Does your skin felt smoother after application? | Strongly disagree (1) | 0 | 0.0 | 0 | 0.0 | 0 | 0.0 | 0 | 0.0 |
| | Disagree (2) | 0 | 0.0 | 0 | 0.0 | 0 | 0.0 | 1 | 3.6 |
| | Fair (3) | 23 | 82.1 | 10 | 35.7 | 8 | 28.6 | 6 | 21.4 |
| | Agree (4) | 5 | 17.9 | 18 | 64.3 | 18 | 64.3 | 19 | 67.9 |
| | Strongly agree (5) | 0 | 0.0 | 0 | 0.0 | 2 | 7.1 | 2 | 7.1 |
| Is this product more effective than the products you previously used? | Strongly disagree (1) | 0 | 0.0 | 0 | 0.0 | 0 | 0.0 | 0 | 0.0 |
| | Disagree (2) | 0 | 0.0 | 0 | 0.0 | 0 | 0.0 | 1 | 3.6 |
| | Fair (3) | 27 | 96.4 | 11 | 39.3 | 9 | 32.1 | 9 | 32.1 |
| | Agree (4) | 0 | 0.0 | 17 | 60.7 | 17 | 60.7 | 16 | 57.1 |
| | Strongly agree (5) | 1 | 3.6 | 0 | 0.0 | 2 | 7.1 | 2 | 7.1 |
| Would you recommend this product to others? | Strongly disagree (1) | 0 | 0.0 | 1 | 3.6 | 0 | 0.0 | 0 | 0.0 |
| | Disagree (2) | 0 | 0.0 | 1 | 3.6 | 0 | 0.0 | 1 | 3.6 |
| | Fair (3) | 27 | 96.4 | 9 | 32.1 | 10 | 35.7 | 8 | 28.6 |
| | Agree (4) | 0 | 0.0 | 16 | 57.1 | 16 | 57.1 | 14 | 50.0 |
| | Strongly agree (5) | 1 | 3.6 | 1 | 3.6 | 2 | 7.1 | 5 | 17.9 |
| Would you purchase this product if it is released? | Strongly disagree (1) | 0 | 0.0 | 2 | 7.1 | 0 | 0.0 | 0 | 0.0 |
| | Disagree (2) | 0 | 0.0 | 0 | 0.0 | 0 | 0.0 | 1 | 3.6 |
| | Fair (3) | 25 | 89.3 | 8 | 28.6 | 8 | 28.6 | 7 | 25.0 |
| | Agree (4) | 3 | 10.7 | 17 | 60.7 | 17 | 60.7 | 16 | 57.1 |
| | Strongly agree (5) | 0 | 0.0 | 1 | 3.6 | 3 | 10.7 | 4 | 14.3 |

As further determined by self-assessment, none of the 28 subjects reported any discomfort or allergic reaction while using the formulation.

These results confirm that treatment with lignin peroxidase, glucose oxidase and glucose is effective at lightening skin by decreasing melanin content, without causing significant irritation of the skin, and further indicate that the complexion of the treated skin continues to improve during the course of treatment.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A cosmetic composition for lightening skin, comprising:
   - a lignin peroxidase of a white rot fungus,
   - a hydrogen peroxide-producing enzyme comprising 1.25 to 125 units/gram glucose oxidase,
   - a substrate of said hydrogen peroxide-producing enzyme comprising 0.175 to 17.5 micromole/gram D-glucose, and
   - a cosmetically acceptable carrier comprising an emulsion.

2. The composition of claim 1, wherein the concentration of said lignin peroxidase is 1.25 to 125 units/gram.

3. The composition of claim 1, further comprising an oxidizing mediator.

4. The composition of claim 3, wherein the concentration of said oxidizing mediator is 0.03 to 300 micromole/gram.

5. The composition of claim 1, wherein said lignin peroxidase is isoenzyme H1 or a modified form of isoenzyme H2.

6. The composition of claim 1, wherein said lignin peroxidase is an extract of a *Phanerochaete chrysosporium* fungus.

7. An air-tight container containing the composition of claim 1.

8. A cosmetic method of lightening the skin and/or hair of a subject, comprising contacting the skin and/or hair of the subject with the composition of claim 1.

9. The method of claim 8, said composition is provided in a kit.

10. The composition of claim 1, wherein the concentration of said lignin peroxidase is 1.25 to 12.5 units/gram.

11. The composition of claim 3, wherein said oxidizing mediator is selected from the group consisting of veratryl alcohol, veratrole and 1,4-dimethoxybenzene.

* * * * *